(12) United States Patent
Lauerman

(10) Patent No.: US 8,685,932 B2
(45) Date of Patent: Apr. 1, 2014

(54) TARGETED TRANSFORMING GROWTH FACTOR-BETA-BOUND IGG FOR TREATMENT OF DISEASES

(75) Inventor: Tod Lauerman, San Diego, CA (US)

(73) Assignee: Option Pharmaceuticals, LLC, Vista, CA (US)

( * ) Notice: Subject to any disclaimer, the term of this patent is extended or adjusted under 35 U.S.C. 154(b) by 0 days.

(21) Appl. No.: 13/140,350

(22) PCT Filed: Dec. 14, 2009

(86) PCT No.: PCT/US2009/067945
§ 371 (c)(1),
(2), (4) Date: Aug. 23, 2011

(87) PCT Pub. No.: WO2010/077831
PCT Pub. Date: Jul. 8, 2010

(65) Prior Publication Data
US 2011/0305716 A1    Dec. 15, 2011

Related U.S. Application Data

(60) Provisional application No. 61/122,901, filed on Dec. 16, 2008.

(51) Int. Cl.
*A61K 38/16* (2006.01)
*A61K 38/17* (2006.01)
*A61K 38/18* (2006.01)
*C07K 14/00* (2006.01)
*C07K 14/495* (2006.01)
*C07K 16/00* (2006.01)
*C07K 16/46* (2006.01)

(52) U.S. Cl.
USPC ....... 514/21.2; 514/8.9; 435/69.7; 530/387.1; 530/350; 424/130.1

(58) Field of Classification Search
None
See application file for complete search history.

(56) References Cited

U.S. PATENT DOCUMENTS

| 5,998,598 | A | 12/1999 | Csaky et al. |
| 2003/0166163 | A1 | 9/2003 | Gillies |
| 2005/0276802 | A1 | 12/2005 | Adams et al. |
| 2006/0275211 | A1 | 12/2006 | Jakobovits et al. |
| 2008/0050375 | A1 | 2/2008 | Davies et al. |
| 2008/0286819 | A1 | 11/2008 | Ravetch et al. |

FOREIGN PATENT DOCUMENTS

| CN | 1435433 | 8/2003 |
| WO | WO 2006/116002 A2 * | 11/2006 |

OTHER PUBLICATIONS

Vukicevic et al. (1996, PNAS USA 93:9021-9026).*
Shen et al. (2004, Eur. J. Neurosci. 20:2031-2037).*
Massague (1987, Cell 49:437-8).*
Adams et al., Journal of Immunology (1991) 147:609-612.
Armour et al., Mol. Immunol. (2003) 40:585-593.
Bouchard et al., J. Exp. Med. (1995) 182:1717-1726.
Bruhns et al., Blood (2009) 113(16):3716-3725.
Calabresi et al., Neurology (1998) 51:289-292.
Caver et al., Journal of Clinical Investigation (1996) 98(11):2496-2506.
Curiel et al., PNAS USA (1991) 88:8850-8854.
Gordon et al., Nat. Rev. Immunol. (2005) 5(12):953-964.
Gordon, Nat. Rev. Immunol. (2003) 3:23-35.
Harada et al., Clin. Exp. Immunol. (2002) 128:204-212.
Highton et al., Clin. Exp. Immunol. (1995) 102:541-546.
International Search Report for PCT/US09/67945, mailed on Mar. 9, 2010 3 pages.
International Preliminary Report on Patentability for PCT/US09/67945, issued on Jun. 21, 2011, 10 pages.
Kaveri et al., New England Journal of Medicine (2008) 359(3):307-309.
Lewis and Pollard, Cancer Res. (2006) 66:605-612.
Maenaka et al., J. Biol. Chem. (2001) 276(48):44898-44904.
Nimmerjahn and Ravetch, Science (2005) 310:1510-1512.
Nimmerjahn et al., Immunity (2005) 23:41-51.
Parekh et al., Journal of Immunology (1994) 152:2456-2466.
Perkett et al., J. Clin. Invest. (1990) 1459-1464.
Richards et al., Mol. Cancer Ther. (2008) 7(8):2517-2527.
Rowley et al., Int. Immunol. (1998) 10(3):355-363.
Seitz et al., Arthritis & Rheumatism (1998) 41(11):2032-2038.
Sica et al., European Journal of Cancer (2006) 42:717-727.
Stach and Rowley, J. Exp. Med. (1993) 178:841-852.
Terrell et al., "Pathology of Recombinant Human Transforming Growth Factor-β1 in Rats and Rabbits" in International Review of Experimental Pathology, vol. 1 (1993) pp. 43-67.
Wahl et al., PNAS USA (1987) 84:5788-5792.
Wakefield et al., Journal of Clinical Investigation (1990) 86:1976-1984.
Zitterkopf et al., Viral Immunology (2003) 16(4):511-523.

* cited by examiner

*Primary Examiner* — Elizabeth C Kemmerer
(74) *Attorney, Agent, or Firm* — Morrison & Foerster LLP

(57) ABSTRACT

Provided are proteins and polynucleotides, complexes and compositions containing the proteins, and methods for their use in administration to subjects and for disease treatment. Among the provided proteins and complexes are complexes containing a TGF-beta associated with immunoglobulins (such as IgGs) or functional portions thereof including Fc portions, such as by non-covalent bonds. The provided complexes include those in which the immunoglobulin portion binds to inhibitory Fcγ receptors to a greater degree than to activating Fcγ receptors. The provided complexes further include those in which the immunoglobulin portion bind to activating Fcγ receptors to a greater degree than to inhibitory Fcγ receptors. The complexes and compositions can be used for administration to subjects, such as for increasing immunity or decreasing inflammation, such as for treating diseases including autoimmune diseases and cancer.

22 Claims, No Drawings

SEQUENCE LISTING

<160> NUMBER OF SEQ ID NOS: 10

<210> SEQ ID NO 1
<211> LENGTH: 339
<212> TYPE: DNA
<213> ORGANISM: Homo sapiens
<220> FEATURE:
<221> NAME/KEY: misc_feature
<222> LOCATION: (1)...(339)
<223> OTHER INFORMATION: TGF-beta 1 coding sequence

<400> SEQUENCE: 1

| | |
|---|---|
| gccctggaca ccaactattg cttcagctcc acggagaaga actgctgcgt gcggcagctg | 60 |
| tacattgact ccgcaagga cctcggctgg aagtggatcc acgagcccaa gggctacc | 118 |
| atg cca act tct gcc tcg ggc cct gcc cct aca ttt gga gcc tgg aca | 166 |
| cgc agt aca gca agg tcc tgg ccc tgt aca acc agc ata acc cgg gcg | 214 |
| cct cgg cgg cgc cgt gct gcg tgc cgc agg cgc tgg agc cgc tgc cca | 262 |
| tcg tgt act acg tgg gcc gca agc cca agg tgg agc agc tgt cca aca | 310 |
| tga tcgtgcgctc ctgcaagtgc agctga | 339 |

<210> SEQ ID NO 2
<211> LENGTH: 990
<212> TYPE: DNA
<213> ORGANISM: Homo sapiens
<220> FEATURE:
<221> NAME/KEY: misc_feature
<222> LOCATION: (1)...(990)
<223> OTHER INFORMATION: coding sequence of Fc region of IgG1

<400> SEQUENCE: 2

| | |
|---|---|
| gcaagcttca agggcccatc ggtcttcccc ctggcaccct cctccaagag cacctctggg | 60 |
| ggcacagcgg ccctgggctg cctggtcaag gactacttcc ccgaaccggt gacggtgtcg | 120 |
| tggaactcag gcgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagaa agttgagccc | 300 |
| aaatcttgtg acaaaactca cacatgccca ccgtgcccag cacctgaact cctggggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcgggagga gcagtacaac | 540 |
| agcacgtacc gtgtggtcag cgtcctcacc gtcctgcacc aggactggct gaatggcaag | 600 |
| gagtacaagt gcaaggtctc caacaaagcc ctcccagccc ccatcgagaa aaccatctcc | 660 |
| aaagccaaag gcagccccg agaaccacag gtgtacaccc tgcccccatc ccgggatgag | 720 |
| ctgaccaaga accaggtcag cctgacctgc ctggtcaaag gcttctatcc cagcgacatc | 780 |
| gccgtggagt gggagagcaa tgggcagccg gagaacaact acaagaccac gcctcccgtg | 840 |
| ctggactccg acggctcctt cttcctctac agcaagctca ccgtggacaa gagcaggtgg | 900 |
| cagcagggga acgtcttctc atgctccgtg atgcatgagg ctctgcacaa ccactacacg | 960 |
| cagaagagcc tctccctgtc tccgggtaaa | 990 |

<210> SEQ ID NO 3
<211> LENGTH: 978
<212> TYPE: DNA

<213> ORGANISM: Homo sapiens
<220> FEATURE:
<221> NAME/KEY: misc_feature
<222> LOCATION: (1)...(978)
<223> OTHER INFORMATION: coding region of Fc region of IgG2

<400> SEQUENCE: 3

| | | | | | |
|---|---|---|---|---|---|
| gcaagcttca | agggcccatc | ggtcttcccc | ctggcgccct | gctccaggag | cacctccgag | 60 |
| agcacagcgg | ccctgggctg | cctggtcaag | gactacttcc | ccgaaccggt | gacggtgtcg | 120 |
| tggaactcag | gcgctctgac | cagcggcgtg | cacaccttcc | cagctgtcct | acagtcctca | 180 |
| ggactctact | ccctcagcag | cgtggtgacc | gtgccctcca | gcaacttcgg | cacccagacc | 240 |
| tacacctgca | acgtagatca | caagcccagc | aacaccaagg | tggacaagac | agttgagcgc | 300 |
| aaatgttgtg | tcgagtgccc | accgtgccca | gcaccacctg | tggcaggacc | gtcagtcttc | 360 |
| ctcttcccc  | caaacccaa  | ggacaccctc | atgatctccc | ggacccctga | ggtcacgtgg | 420 |
| gtggtggtgg | acgtgagcca | cgaagacccc | gaggtccagt | tcaactggta | cgtggacggc | 480 |
| gtggaggtgc | ataatgccaa | gacaaagcca | cgggaggagc | agttcaacag | cacgttctgt | 540 |
| gtggtcagcg | tcctcaccgt | tgtgcaccag | gactggctga | acggcaagga | gtacaagtgc | 600 |
| aaggtctcca | acaaaggcct | cccagccccc | atcgagaaaa | ccatctccaa | aaccaaaggg | 660 |
| cagccccgag | aaccacaggt | gtacaccctg | cccccatccc | gggaggagat | gaccaagaac | 720 |
| caggtcagcc | tgacctgcct | ggtcaaaggc | ttctacccca | gcgacatcgc | cgtggagtgg | 780 |
| gagagcaatg | ggcagccgga | gaacaactac | aagaccacac | ctcccatgct | ggactccgac | 840 |
| ggctccttct | tcctctacag | caagctcacc | gtggacaaga | gcaggtggca | gcaggggaac | 900 |
| gtcttctcat | gctccgtgat | gcatgaggct | ctgcacaacc | actacacgca | gaagagcctc | 960 |
| tccctgtctc | cgggtaaa   | | | | | 978 |

<210> SEQ ID NO 4
<211> LENGTH: 753
<212> TYPE: DNA
<213> ORGANISM: Homo sapiens
<220> FEATURE:
<221> NAME/KEY: misc_feature
<222> LOCATION: (1)...(753)
<223> OTHER INFORMATION: coding region of Fc region of IgG3

<400> SEQUENCE: 4

| | | | | | |
|---|---|---|---|---|---|
| atcacaagcc | cagcaacacc | aaggtggaca | agagagttga | gctcaaaacc | ccacttggtg | 60 |
| acacaactca | cacatgccca | ccgtgcccag | cacctgaact | cctgggggga | ccgtcagtct | 120 |
| tcctcttccc | cccaaaaccc | aaggacaccc | tcatgatctc | ccggaccect | gaggtcacat | 180 |
| gcgtggtggt | ggacgtgagc | cacgaagacc | ctgaggtcaa | gttcaactgg | tacgtggatg | 240 |
| gcgtggaggt | gcataatgcc | aagacaaagc | cgcgggagga | gcagtacaac | agcacgtacc | 300 |
| gtgtggtcag | cgtcctcacc | gtcctgcacc | aggactggct | gaatggcaag | gagtacaagt | 360 |
| gcaaggtctc | caacaaagcc | ctcccagccc | ccatcgagaa | aaccatctcc | aaagccaaag | 420 |
| ggcagccccg | agaaccacag | gtgtacaccc | tgccecatc  | ccgggatgag | ctgaccaaga | 480 |
| accaggtcag | cctgacctgc | ctggtcaaag | gcttctatcc | cagcgacatc | gccgtggagt | 540 |
| gggagagcaa | tggggcagccg | gagaacaact | acaagaccac | gcctcccgtg | ctggactccg | 600 |
| acggctcctt | cttcctctac | agcaagctca | ccgtggacaa | gagcaggtgg | cagcagggga | 660 |
| acgtcttctc | atgctccgtg | atgcatgagg | ctctgcacaa | ccactacacg | cagaagagcc | 720 |
| tctccctgtc | tccgggtaaa | tgagtgcgac | ggc | | | 753 |

<210> SEQ ID NO 5
<211> LENGTH: 981
<212> TYPE: DNA
<213> ORGANISM: Homo sapiens
<220> FEATURE:
<221> NAME/KEY: misc_feature
<222> LOCATION: (1)...(981)
<223> OTHER INFORMATION: coding region of Fc region of IgG4

<400> SEQUENCE: 5

```
gcaagcttca agggcccatc ggtcttcccc ctggtgccct gctccaggag cacctccgag      60
agcacagccg ccctgggctg cctggtcaag gactacttcc ccgaaccggt gacggtgtcg     120
tggaactcat gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gggtcctcac cgtcctgcac caggactggc tgaacggtaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggaggacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctccgggtaa a                                               981
```

<210> SEQ ID NO 6
<211> LENGTH: 112
<212> TYPE: PRT
<213> ORGANISM: Homo sapiens
<220> FEATURE:
<221> NAME/KEY: misc_feature
<222> LOCATION: (1)...(112)
<223> OTHER INFORMATION: TgF-beta 1

<400> SEQUENCE: 6

```
Ala Leu Asp Thr Asn Tyr Cys Phe Ser Ser Thr Glu Lys Asn Cys Cys
  1               5                  10                  15
Val Arg Gln Leu Tyr Ile Asp Phe Arg Lys Asp Leu Gly Trp Lys Trp
             20                  25                  30
Ile His Glu Pro Lys Gly Tyr His Ala Asn Phe Cys Leu Gly Pro Cys
         35                  40                  45
Pro Tyr Ile Trp Ser Leu Asp Thr Gln Tyr Ser Lys Val Leu Ala Leu
     50                  55                  60
Tyr Asn Gln His Asn Pro Gly Ala Ser Ala Ala Pro Cys Cys Val Pro
 65                  70                  75                  80
Gln Ala Leu Glu Pro Leu Pro Ile Val Tyr Tyr Val Gly Arg Lys Pro
                 85                  90                  95
Lys Val Glu Gln Leu Ser Asn Met Ile Val Arg Ser Cys Lys Cys Ser
            100                 105                 110
```

<210> SEQ ID NO 7
<211> LENGTH: 330
<212> TYPE: PRT
<213> ORGANISM: Homo sapiens
<220> FEATURE:
<221> NAME/KEY: misc_feature
<222> LOCATION: (1)...(330)
<223> OTHER INFORMATION: Fc region of IgG1

<400> SEQUENCE: 7

```
Ala Ser Phe Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 8
<211> LENGTH: 326
<212> TYPE: PRT
<213> ORGANISM: Homo sapiens
<220> FEATURE:

```
<221> NAME/KEY: misc_feature
<222> LOCATION: (1)...(326)
<223> OTHER INFORMATION: Fc region of IgG2

<400> SEQUENCE: 8
```

| | | | | | | | | | | | | | | |
|---|---|---|---|---|---|---|---|---|---|---|---|---|---|---|
| Ala | Ser | Phe | Lys | Gly | Pro | Ser | Val | Phe | Pro | Leu | Ala | Pro | Cys | Ser | Arg |
| 1 | | | | 5 | | | | | 10 | | | | | 15 | |
| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Asn | Phe | Gly | Thr | Gln | Thr |
| 65 | | | | | 70 | | | | | 75 | | | | | 80 |
| Tyr | Thr | Cys | Asn | Val | Asp | His | Lys | Pro | Ser | Asn | Thr | Lys | Val | Asp | Lys |
| | | | | 85 | | | | | 90 | | | | | 95 | |
| Thr | Val | Glu | Arg | Lys | Cys | Cys | Val | Glu | Cys | Pro | Pro | Cys | Pro | Ala | Pro |
| | | | 100 | | | | | 105 | | | | | 110 | | |
| Pro | Val | Ala | Gly | Pro | Ser | Val | Phe | Leu | Phe | Pro | Pro | Lys | Pro | Lys | Asp |
| | | 115 | | | | | 120 | | | | | 125 | | | |
| Thr | Leu | Met | Ile | Ser | Arg | Thr | Pro | Glu | Val | Thr | Trp | Val | Val | Val | Asp |
| | 130 | | | | | 135 | | | | | 140 | | | | |
| Val | Ser | His | Glu | Asp | Pro | Glu | Val | Gln | Phe | Asn | Trp | Tyr | Val | Asp | Gly |
| 145 | | | | | 150 | | | | | 155 | | | | | 160 |
| Val | Glu | Val | His | Asn | Ala | Lys | Thr | Lys | Pro | Arg | Glu | Glu | Gln | Phe | Asn |
| | | | | 165 | | | | | 170 | | | | | 175 | |
| Ser | Thr | Phe | Cys | Val | Val | Ser | Val | Leu | Thr | Val | Val | His | Gln | Asp | Trp |
| | | | 180 | | | | | 185 | | | | | 190 | | |
| Leu | Asn | Gly | Lys | Glu | Tyr | Lys | Cys | Lys | Val | Ser | Asn | Lys | Gly | Leu | Pro |
| | | 195 | | | | | 200 | | | | | 205 | | | |
| Ala | Pro | Ile | Glu | Lys | Thr | Ile | Ser | Lys | Thr | Lys | Gly | Gln | Pro | Arg | Glu |
| 210 | | | | | 215 | | | | | 220 | | | | | |
| Pro | Gln | Val | Tyr | Thr | Leu | Pro | Pro | Ser | Arg | Glu | Glu | Met | Thr | Lys | Asn |
| 225 | | | | | 230 | | | | | 235 | | | | | 240 |
| Gln | Val | Ser | Leu | Thr | Cys | Leu | Val | Lys | Gly | Phe | Tyr | Pro | Ser | Asp | Ile |
| | | | | 245 | | | | | 250 | | | | | 255 | |
| Ala | Val | Glu | Trp | Glu | Ser | Asn | Gly | Gln | Pro | Glu | Asn | Asn | Tyr | Lys | Thr |
| | | | 260 | | | | | 265 | | | | | 270 | | |
| Thr | Pro | Pro | Met | Leu | Asp | Ser | Asp | Gly | Ser | Phe | Phe | Leu | Tyr | Ser | Lys |
| | | 275 | | | | | 280 | | | | | 285 | | | |
| Leu | Thr | Val | Asp | Lys | Ser | Arg | Trp | Gln | Gln | Gly | Asn | Val | Phe | Ser | Cys |
| | 290 | | | | | 295 | | | | | 300 | | | | |
| Ser | Val | Met | His | Glu | Ala | Leu | His | Asn | His | Tyr | Thr | Gln | Lys | Ser | Leu |
| 305 | | | | | 310 | | | | | 315 | | | | | 320 |
| Ser | Leu | Ser | Pro | Gly | Lys |
| | | | | 325 | |

```
<210> SEQ ID NO 9
<211> LENGTH: 246
<212> TYPE: PRT
<213> ORGANISM: Homo sapiens
<220> FEATURE:
<221> NAME/KEY: misc_feature
<222> LOCATION: (1)...(246)
<223> OTHER INFORMATION: Fc region of IgG3

<400> SEQUENCE: 9
```

His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 10
<211> LENGTH: 327
<212> TYPE: PRT
<213> ORGANISM: Homo sapiens
<220> FEATURE:
<221> NAME/KEY: misc_feature
<222> LOCATION: (1)...(327)
<223> OTHER INFORMATION: Fc region of IgG4

<400> SEQUENCE: 10

Ala Ser Phe Lys Gly Pro Ser Val Phe Pro Leu Val Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Cys Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro

-continued

```
              100                 105                 110
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Arg Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asp Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325
```

TARGETED TRANSFORMING GROWTH FACTOR-BETA-BOUND IGG FOR TREATMENT OF DISEASES

RELATED APPLICATION

This application is a U.S. National Phase Application of International Application No. PCT/US2009/067945 filed on Dec. 14, 2009, which claims priority to U.S. Provisional Patent Application Ser. No. 61/122,901 filed on Dec. 16, 2008, the contents of which are incorporated in their entirety by reference herein.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 655162000300Seqlist.txt | Jul. 15, 2011 | 17,831 bytes |

TECHNICAL FIELD

Provided are proteins, such as TGF-beta proteins, including targeted TGF-beta proteins, and immunoglobulin (Ig) proteins, and complexes of the proteins, such as TGF-beta-Ig complexes, including TGF-beta IgG complexes; compositions and combinations containing the proteins and complexes; processes for making such proteins and complexes; and methods for disease treatment, such as methods for treatment of cancer and autoimmune diseases, by administering such proteins, complexes, combinations, and compositions.

BACKGROUND

Transforming growth factor-beta (TGF-beta) belongs to a superfamily of structurally related regulatory proteins, which includes activin/inhibin and bone morphogenic proteins. Three isoforms of TGF-beta are produced in mammals: TGF-beta 1, TGF-beta 2, and TGF-beta 3. TGF-beta forms a homodimer, which typically is secreted as an inactive, latent complex, having two covalently linked propeptides (the latency-associated protein, or "LAP"), non-covalently bound to, and inactivating, the dimeric mature TGF-beta molecule. Activation of the latent complex in vivo occurs either through dissociation of the TGF-beta dimer from LAP (via proteases, nitric oxide, or other means), or through a conformational change in the latent complex caused by binding of LAP to either thrombospondin or $\alpha v \beta 6$ integrin. Active TGF-beta dimmers specifically bind to TGF-beta Receptor II (TGF-beta RII), and typically bind two TGF-beta RII molecules. Binding by the TGF-beta homodimer recruits two TGF-beta Receptor I (TGF-beta RI) molecules, forming a heteromeric complex. Downstream signaling is mediated by the bound TGF-beta RI, a serine-threonine kinase, which is phosphorylated upon complexation to the TGF-beta/TGF-beta RII complex. Activation of TGF-beta RI causes phosphorylation of Smad2 and Smad3 and induces their heterodimerization with Smad4. The activated Smad complex then translocates to the nucleus where it regulates gene transcription.

TGF-beta regulates a plurality of processes, including cell differentiation and proliferation, migration, motility, deposition of the extracellular matrix, cell death, and immunosuppression. TGF-beta signaling can increase the synthesis of matrix proteins, such as vitronectin, fibronectin, laminin, tenascin, proteoglycans, and collagens, enhance the expression of cell adhesion molecules such as integrins, and increase the synthesis of various protease inhibitors. It also can decrease the synthesis of matrix degrading proteases.

TGF-beta, a potent immunosuppressant molecule, has profound inhibitory effects on several major immune system cell types, including T-cells (both $CD4^+$ and $CD8^+$), B lymphocytes, monocytes, macrophages, dendritic cells, polymorphonuclear leukocyte. Additionally, TGF-beta is a powerful chemoattractant for a plurality of types of immune cells, including T-cells (both $CD4^+$ and $CD8^+$), monocytes, PMNs, neutrophils and mast cells.

Different cells of the immune system have been characterized according to their activating (e.g., pro-inflammatory) or inhibitory (e.g., immunosuppressive) effects. Monocyte-lineage cells (e.g., macrophages) can be classified into the M1 (activating, inflammatory) and M2 (inhibitory) phenotype based on function and on expression patterns of proteins including cytokines, chemokines, surface receptors, apoptosis-related genes, soluble carriers, enzymes, extracellular mediators, and DNA binding factors. For example, certain proteins are expressed in these different monocyte cell types with greater than 200-fold differences. Differentiation of M1 versus M2 macrophages is well established and has been verified and extensively characterized based on different cytokine secretion profiles following *E. coli* lipopolysaccharide (LPS) challenge. After LPS challenge in culture, M1 macrophages overproduce tumor necrosis factor-alpha (TNF-alpha) and interferon-gamma (IFN-γ), whereas M2 macrophages overproduce monocyte chemotactic protein-1 (MCP-1) and interleukin-10 (IL-10).

Fc receptors are cell surface receptors, expressed on various immune cell types, that specifically bind Fc regions of immunoglobulin molecules. The Fc region is an effector-function conferring portion of the immunoglobulin constant region. Fc receptors are generally categorized according to the class of Ig molecule they recognize. For example, Fc gamma receptors (FcγR) bind Fc portions of IgG molecules. Mammalian Fc gamma receptors are further classified into four classes (FcγRI (CD64), FcγRII (CD32), FcγRIII (CD16) and FcγRIV). The FcγRII class further includes the functionally distinct FcγRIIa and FcγRIIb sub-types. FcgRI has a high affinity for IgG Fc regions, can bind monomeric IgG at physiological concentrations of IgG, and has a restricted isotype specificity. FcγII and FcγIII receptors have low affinities for IgG Fc regions and typically only can bind multimeric IgG (for example, immune complexes and dimeric IgG) at physiological IgG concentrations.

Fc receptors, particularly Fc gamma receptors, can also be categorized into two functional classes: activating Fc receptors (including FcγRI, FcγRIIa, FcγRIII and FcγRIV) and inhibitory Fc receptors (including the sole naturally occurring inhibitory Fc receptor, FcγRIIb). Activating FcγRs are expressed on all myeloid cells, and their cross-linking results in sustained cellular responses. With the exception of T cells and NK cells, FcγRIIb is expressed in all cells of the immune system. When properly bound, FcγRIIb inhibits activation and proliferation of the cell in which it is expressed. Different cells of the immune system express different ratios of activating versus inhibitory FcγRs. For example, monocyte-lineage cells of the M1 (inflammatory) phenotype express overabundant amounts of activating FcγR, compared to the inhibitory FcγR. By contrast, M2-type monocyte-lineage cells display an overabundance in inhibitory FcγR expression compared to activating FcγRs (see Gordon, *Nat. Rev. Immonol.* 2005 December; 5(12):953-64).

Different FcγRs have varying affinities for particular subclasses of IgG molecules. For example, Nimmerjahn and Ravetch (*Science*, 310:1510-1512, 2005) reported that although all FcγRs can bind IgG immune complexes, individual Fcγ receptors display significantly different affinities for different IgG subclasses.

This report described the different affinities of particular IgG subclasses for functionally different Fcγ receptors as activating-to-inhibitory (A/I) ratios. The A/I ratio for each IgG subclass represented the affinity of the subclass for activating Fcγ receptors (either sFcγRIII or sFcγRIV) compared to its affinity for the inhibitory receptor (FcγRIIB).

The ratio, calculated based on affinities determined through in vitro binding to Fcγ receptors, accurately predicted the efficacy of particular IgG sub-classes to mediate immune function. For example, the ratio could predict the ability of specific isotypes of anti-tumor antibodies with identical CDRs (and thus, identical antigen specificity), to mediate immune effector responses. Differential efficiency of binding by various IgG subtypes to inhibitory and activating Fcγ receptors also has been described in humans (Armour, K L et al., *Mol Immunol*, 40:585-593, 2003; Bruhns, P. et al., *Blood* Nov. 18, 2008, Epub ahead of print).

Cancer is the second leading cause of death by disease in the United States, resulting in 1 of every 4 deaths. There is growing evidence that the microenvironments of tumors are overabundant in tumor-associated macrophages (TAMS) and myeloid-derived suppressor cells (MDSCs). These cells of myeloid origin and M2 phenotype, help to create an immunosuppressive environment that dampens anti-tumor immune responses.

Autoimmune diseases are responsible for a great deal of morbidity and mortality throughout the world, and have been described as the most prevalent group of diseases in the world. Autoimmune diseases are among the leading causes of death among young and middle aged women in the United States. Because these diseases tend to be chronic, they have a significant impact on medical utilization, direct and indirect economic costs, and quality of life. The prevalence of all autoimmune diseases has been estimated at over 5% of the US population, and most of its victims are women.

Rheumatoid arthritis (RA) is an inflammatory autoimmune disease caused by the attack by the immune system on the joints of an individual. RA is painful and often debilitating. RA affects women three times more often than men. RA affects more than 1% of the US population.

Current treatments include anti-inflammatory medication and anti-tumor necrosis factor-alpha therapies. Inflammatory macrophages (e.g., M1 phenotype macrophages) and B cells contribute to both inflammation and tissue destruction in RA.

Available proteins for treatment of cancer and autoimmune diseases are limited. For example, protein therapeutics with increased efficacy, half-life and specificity are needed. As an immunosuppressant and immune cell chemoattractant, TGF-beta is an attractive candidate for producing therapeutic effects on cells of the immune system. However, available TGF-beta proteins and their use in treating diseases are limited.

In particular, there is a need for TGF-beta proteins and complexes, including targeted TGF-beta proteins and complexes, with improved in vivo half-lives, and for TGF-beta proteins and complexes having specificity for particular cell types and specific effects on particular immune system and immune cell function. For example, TGF-beta proteins and complexes that do not have pleiotropic effects or have reduced pleiotropic effects are needed. Accordingly, it is among the objects of the invention to provide TGF-beta proteins, complexes (e.g., multimers, such as dimers), including proteins and complexes with high efficacy, specificity, availability and half-life, and combinations and compositions containing the TGF-beta proteins, and methods for treating diseases with the proteins and complexes.

SUMMARY

Provided herein are TGF beta proteins and complexes (e.g., multimers, dimers) containing the TGF-beta proteins, such as complexes containing TGF-beta proteins and immunoglobulins or portions thereof. The TGF-beta complexes can be targeted to particular cell types based on their affinities for receptors differentially expressed on different cells, such as immune cells. The provided proteins and complexes include those with long in vivo half lives, those with specificity to particular cell types, and those having no pleiotropic effects, or having reduced pleiotropic effects compared to free TGF-beta proteins. The provided proteins and complexes can be used to treat diseases. For example, in one embodiment, the provided proteins and complexes can be used in treatment of diseases associated with immunosuppression, such as cancer. In another embodiment, the provided proteins and compositions can be used for treating diseases associated with inflammation, such as autoimmune diseases, allergy and asthma.

Uses and methods of using the provided proteins and complexes for administration to subjects and treating diseases also are provided. Also provided are combinations and compositions, e.g., pharmaceutical compositions, containing the TGF-beta proteins and complexes, and methods for using the provided compositions.

Among the provided complexes are Transforming Growth Factor-beta-bound IgGs (TIGGs). The TIGG is typically an isolated or purified TIGG. Typically, the provided complex (e.g., the TIGG) contains an immunoglobulin (Ig) portion and a transforming growth factor-beta (TGF-beta) portion, which contain one or more Ig protein and one or more TGF-beta protein, respectively.

The Ig portion can contain one Ig protein, or a plurality of Ig proteins, which can be full length Ig molecules or functional regions thereof, and include wild-type and variant Ig proteins as described herein. The Ig protein can be any known Ig protein, including a full-length immunoglobulin (such as a human IgG1, IgG2, IgG3 or IgG4) or functional region thereof such as an Fc region or portion thereof, including the Ig proteins disclosed herein. Typically, the Ig protein is an IgG (in the case of a TIGG) or functional region thereof. The Ig proteins include proteins with an Fc region having at least at or about 80% sequence identity to the sequence of amino acids set forth in SEQ ID NO:7, SEQ ID NO:8, SEQ ID NO:9 or SEQ ID NO:10. In one aspect, the Ig protein is a portion of an Ig molecule, such as an Fc region having at least at or about 70%, at least at or about 75%, or at least at or about 80%, such as at least at or about or at or about 80, 81, 82, 83, 84, 85, 86, 87, 88, 89, 90, 91, 92, 93, 94, 95, 96, 97, 98, 99 or 100% sequence identity to the sequence of amino acids set forth in SEQ ID NO:7, SEQ ID NO:8, SEQ ID NO:9 or SEQ ID NO:10.

The TGF-beta portion contains one or more TGF-beta protein. In one example, the TGF-beta portion contains two TGF-beta proteins, that are monomers associated to form a dimer via covalent bond, such as an activated, mature, TGF-beta homodimer, for example, a 25 kDa TGF-beta homodimer or variant thereof. The TGF-beta protein can be any known TGF-beta, including TGF-beta 1, TGF-beta 2 and TGF-beta 3 and monomers thereof, and any of the TGF-beta proteins described herein, including variants that retain TGF-beta activity. In one embodiment, the TGF-beta protein has at least at or about 70%, at least at or about 75%, or at least at or about 80%, such as at least at or about or at or about 80, 81, 82, 83, 84, 85, 86, 87, 88, 89, 90, 91, 92, 93, 94, 95, 96, 97, 98, 99 or 100%, sequence identity to the sequence of amino acids set forth in SEQ ID NO:6.

The Ig portion and the TGF-beta portion of the complex (e.g., the TIGG) (e.g., the Ig protein(s) and the TGF-beta protein(s) thereof) are associated, typically by a non-covalent bond. In one example, the complex contains two Ig proteins associated with two TGF-beta proteins, such as the monomers of a TGF-beta dimer (homodimer or heterodimer). Typically, the Ig protein(s) and the TGF-beta protein(s) are associated directly, without an intermediate protein or peptide. For example, in one aspect, the complex (e.g., TIGG) does not contain a latent-associated protein. In one example, the complex contains a TGF-beta dimer where each monomer subunit of the TGF-beta dimer is non-covalently bound to an Ig protein of the Ig portion.

The complexes, such as the TIGGs typically have particular functional characteristics, such as specified binding affinities or relative binding affinities, for other molecules. In one embodiment, the TIGG, or the Ig portion thereof, contains at least a two-fold higher binding affinity, such as a 2, 3, 4, 5, 6, 7, 8, 9, 10, 11, 12, 13, 14, 15, 20, 25, 30, 35, 40, 45, 50, 55, 60, 65, 70, 75, 80, 85, 90 or more fold higher binding affinity, for one or more Fc receptor subset, such as Fc gamma receptor subset, compared to another subset, such as the other Fc gamma receptor subset or subsets. Among such subsets are the activating class of Fc receptors and the inhibitory class of Fc receptors, and particular classes of Fc receptors categorized by the Ig isotype or sub-type that they bind. Thus, when it is said that the complex or Ig portion has a higher affinity for one Fc gamma receptor subset than the other, this typically refers to the activating versus inhibitory subsets.

In one aspect, the TIGG is an activating TIGG (AcTIGG). Typically, the AcTIGG, and the Ig portion thereof, contains a higher binding affinity for inhibitory Fc gamma receptors compared to activating Fc gamma receptors. For example, in one embodiment, the Ig portion or AcTIGG has an activating-to-inhibitory ratio (A/I ratio) of less than at or about 1, less than at or about 0.5, less than at or about 0.4, less than at or about 0.3, less than at or about 0.2, less than at or about 0.1, less than at or about 0.05, less than at or about 0.01 or less than at or about 0.005, or at or about 0.5, 0.3, 0.2, 0.1, 0.05, 0.01 or 0.001, such as, for example, an A/I ratio of less than at or about 0.9, 0.8, 0.7, 0.6, and typically less than at or about 0.5, such as 0.4, 0.3, 0.2, 0.1, 0.09, 0.08, 0.07, 0.06, 0.05, 0.04, 0.03, 0.02, 0.01, 0.009, 0.005, or 0.001.

In one example, the Ig portion of the AcTIGG contains a human IgG4, a portion thereof (e.g., a functional region thereof) or a variant thereof. In another example, the Ig protein contains an Fc region having at least 80% sequence identity to the sequence of amino acids set forth in SEQ ID NO:10, or has at least 80% sequence identity to the sequence of amino acids set forth in SEQ ID NO:10.

In another aspect, the TIGG is an inhibitory TIGG (InTIGG). Typically the InTIGG (or Ig portion thereof) contains a higher binding affinity for activating Fc gamma receptors compared to activating Fc gamma receptors. For example, in one embodiment, the InTIGG or Ig portion thereof has an A/I ratio of greater than at or about 2, greater than at or about 5, greater than at or about 10, greater than at or about 15, greater than at or about 20, greater than at or about 25, greater than at or about 50, or at or about 2, 5, 10, 15, 20, 25, 50 or 70, or 90, such as at least at or about 2, 3, 4, 5, 6, 7, 8, 9, 10, 11, 12, 13, 14, 15, 16, 17, 18, 19, 20, 25, 30, 35, 40, 45, 50, 55, 60, 65, 70, 80 or 90 or greater. In one aspect, the InTIGG contains one or more of a human IgG1 or Fc portion thereof, a human IgG2 or Fc portion thereof, and a human IgG3 or Fc portion thereof, or a variant thereof.

In another example, the Ig protein contains an Fc region having at least 80% sequence identity to the sequence of amino acids set forth in any of SEQ ID NOs:7, 8 and 9, or is an Fc region having at least 80% sequence identity to the sequence of amino acids set forth in any of SEQ ID NOs:7, 8 and 9.

The complexes further typically have TGF-beta activity. In one embodiment, the TIGG has TGF-beta activity at a physiological pH. In another embodiment, the TGF-beta activity is at least substantially the same as the TGF-beta activity of a wild-type TGF-beta or other TGF-beta described herein, such as the TGF-beta activity of a TGF-beta protein having the amino acid sequence set forth in SEQ ID NO:6.

Also provided are mixtures of the TGF-beta containing complexes (e.g., TIGGs). The mixtures can include Ig portions of different isotypes and/or sub-types (including different variant Ig proteins, such as those mutated to optimize A/I ratios). In one example, the mixture contains a plurality of TIGGs, where the various Ig portions contain Immunoglobulins of a human gamma globulin, or IVIG mixture. The mixtures include mixtures of any of the provided complexes, in any desired combination. Typically, the mixture contains TIGGs having a particular relative affinity for activating versus inhibitory Fc receptors, such as a mixture of TIGGs with relatively high A/I ratios (InTIGG mixture) or a mixture of TIGGs with relatively low A/I ratios (AcTIGG mixture).

Also provided are vectors encoding the complexes, such as vectors encoding the any of the TIGGs. For example, in one embodiment, the vector contains a polynucleotide encoding a TGF-beta protein having at least at or about 80% sequence identity to the sequence of amino acids set forth in SEQ ID NO:6, and a polynucleotide encoding an Ig protein containing an Fc region having at least at or about 80% sequence identity to an amino acid sequence set forth in any of SEQ ID NO:7, SEQ ID NO:8, SEQ ID NO:9 and SEQ ID NO:10. The vectors include viral vectors.

Also provided are host cells containing the vectors, and processes for producing the complexes, such as the TIGG complexes, using the vectors. In one embodiment, the process is performed by culturing the host cell under conditions sufficient for the production of proteins encoded by the polynucleotides, and recovering the TIGG, the TGF-beta protein, and/or the Ig protein. Also provided are processes for producing the complexes including the TIGGs. In one embodiment, the process is performed by combining a TGF-beta protein and an Ig protein under conditions whereby they associate via a non-covalent bond and separating the TIGG from free TGF-beta and free Ig, thereby recovering the TIGG. In one aspect, the TGF-beta protein and Ig protein are incubated in a buffer having a pH of at least at or about 7, at or about 8, at or about 9, at or about 10, or at or about 11.

Also provided are pharmaceutical compositions containing the complexes, such as any of the TIGG complexes, and/or the mixtures, admixed with a pharmaceutically acceptable carrier.

The TIGGs, mixtures and compositions can be administered to a subject to treat, ameliorate, and/or prevent diseases and conditions and symptoms thereof, and in particular diseases that are associated with a cell type or cell types having a relatively higher expression level of one class of Fc receptors (e.g., inhibitory or activating FcγR) compared to another, such as diseases associated with immunosuppression and diseases associated with inflammation, such as cancer and autoimmunity. Provided are methods for administering the compositions, complexes (TIGGs) and mixtures to subjects to treat, ameliorate or prevent such diseases and uses of the compositions, mixtures and complexes in such therapies and in preparing medicaments for treating, ameliorating and/or preventing such diseases and conditions.

Among the diseases treated by the methods, uses and pharmaceutical compositions are those associated with immunosuppression, such as cancer.

In one aspect, the cancer is a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, or uterus.

Also among the diseases are those associated with heightened immune activity, such as inflammation, including autoimmunity, allergy, and asthma. Among the autoimmune diseases are Addison's Disease, autoimmune hemolytic anemia, autoimmune inner ear disease, autoimmune lymphoproliferative syndrome, autoimmune thrombocytopenic purpura, autoimmune hemolytic anemia, autoimmune hepatitis, autoimmune oophoritis, Behçet's disease, autoimmune bullous pemphigoid, autoimmune cardiomyopathy, Crohn's disease, autoimmune chronic fatigue syndrome, chronic obstructive pulmonary disease (COPD), including chronic bronchitis, emphysema and chronic asthmatic bronchitis, autoimmune dermatomyositis, autoimmune diabetes mellitus type-1, autoimmune epilepsy autoimmune, Kawasaki's disease, autoimmune glomerulonephritis, Grave's disease, Goodpasture's syndrome, Guillain-Barré syndrome, lupus nephritis, multiple sclerosis, myasthenia gravis, autoimmune myocarditis, autoimmune Parkinson diseases, pediatrics autoimmune neuropsychiatry disorders, autoimmune pemphigus/pemphigoid, autoimmune pernicious anemia, autoimmune polyarteritis nodosa, autoimmune polymyositis, autoimmune primary biliary cirrhosis, psoriasis, autoimmune rheumatic fever, rheumatoid arthritis, autoimmune sarcoidosis, scleroderma, Sjogren's syndrome, autoimmune thyroiditis, autoimmune ulcerative colitis, autoimmune uveitis, autoimmune vitiligo, Wegener's granulomatosis, and Wilson's disease.

For example, provided are methods for treating a subject by administering a therapeutically effective amount of the pharmaceutical composition to the subject. In one embodiment, the TIGG of the composition inhibits the growth, differentiation, proliferation, or survival of a cell in the subject. In one aspect, the cell expresses a relatively higher amount of activating FcγRs compared to inhibitory FcγR. In another aspect, it expresses a relatively higher amount of inhibitory FcγR compared to activating FcγRs.

Also provided are methods for reducing inflammation in a subject, comprising administering a therapeutically effective amount of the pharmaceutical composition to the subject, and uses of the provided compositions and complexes in reducing inflammation.

Also provided are methods for promoting an immune response in a subject, comprising administering a therapeutically effective amount of the pharmaceutical composition to the subject, and uses of the provided compositions in promoting an immune response. Also provided are methods for treating, preventing, or ameliorating a disease or condition associated with immunosuppression in a subject by administering a therapeutically effective amount of the pharmaceutical composition to the subject, whereby immunosuppression is reduced. In one embodiment, the disease or condition is cancer, cancer cell invasiveness or tumor metastasis.

Also provided are methods for inhibiting cancer cell invasiveness or tumor metastasis in a subject with cancer, by administering a therapeutically effective amount of the pharmaceutical composition to the subject, whereby cancer cell invasiveness or tumor metastasis is prevented or reduced.

Also provided are methods for preventing or reducing the chances of tumor recurrence in a subject following surgery for cancer by administering a therapeutically effective amount of the pharmaceutical composition to the subject, for example, whereby tumor recurrence is prevented or the chances of recurrence are reduced. Also provided are methods for treating, preventing, or ameliorating a disease or condition associated with inflammation in a subject, such as an autoimmune disease or condition, by administering a therapeutically effective amount of the pharmaceutical composition to the subject.

The pharmaceutical compositions can be administered by any route, such as subcutaneously, transdermally, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. In one embodiment, the pharmaceutical composition is administered by subcutaneous injection, intraperitoneal injection, or by intravenous injection. In another embodiment, the administration is intravenous or oral administration.

DETAILED DESCRIPTION

Outline

A. Definitions
B. TGF-beta proteins, complexes containing TGF-beta proteins, and methods of use
   i. TGF-beta
   ii. Immunoglobulins and Fc Receptors
   iii. Complexes, including TGF-beta—IgGs (TIGGs)
     a. Naturally occurring and purified TGF-beta—IgG complexes
     b. TGF-beta portions of the provided complexes
     c. Immunoglobulin portions of the complexes
     d. Association of the TGF-beta and Ig portions of the complex
     e. AcTIGGs
     f. InTIGGs
     g. Polynucleotides
   vi. Methods of producing the TIGG complexes
   vii. Methods for evaluating the TGF-beta containing complexes
     a. Binding affinities
     b. Activity
C. Therapeutic Applications
   i. Methods of using AcTIGGs
   ii. Methods of using InTIGGs
D. Pharmaceutical Compositions, dosing and administration
E. Gene Therapy
F. Transgenic Non-Human animals
G. Examples

A. DEFINITIONS

Unless defined otherwise, all technical and scientific terms used herein have the same meaning as is commonly understood by one of ordinary skill in the art to which this invention belongs. All patents, published patent applications, other publications and sequences from GenBank, and other databases referred to herein are incorporated by reference in their entirety. If a definition set forth in this section is contrary to, or otherwise inconsistent with, a definition set forth in patents, published patent applications and other publications and sequences from GenBank and other data bases that are herein incorporated by reference, the definition set forth in this section prevails over the definition that is incorporated herein by reference.

The practice of the provided embodiments will employ, unless otherwise indicated, conventional techniques of molecular biology and the like, which are within the skill of the art. Such techniques are explained fully in the literature. See e.g., *Molecular Cloning: A Laboratory Manual*, (J. Sambrook et al., Cold Spring Harbor Laboratory, Cold Spring Harbor, N.Y., 1989); Current Protocols in Molecular Biology (F. Ausubel et al. eds., 1987 and updated); *Essential Molecular Biology* (T. Brown ed., IRL Press 1991); *Gene Expression Technology* (Goeddel ed., Academic Press 1991); *Methods for Cloning and Analysis of Eukaryotic Genes* (A. Bothwell et al. eds., Bartlett Publ. 1990); *Gene Transfer and Expression* (M. Kriegler, Stockton Press 1990); *Recombinant DNA Methodology* (R. Wu et al. eds., Academic Press 1989); *PCR: A Practical Approach* (M. McPherson et al., IRL Press at Oxford University Press 1991); *Cell Culture for Biochemists* (R. Adams ed., Elsevier Science Publishers 1990); *Gene Transfer Vectors for Mammalian Cells* (J. Miller & M. Calos eds., 1987); *Mammalian Cell Biotechnology* (M. Butler ed., 1991); *Animal Cell Culture* (J. Pollard et al. eds., Humana Press 1990); *Culture of Animal Cells,* 2nd Ed. (R. Freshney et al. eds., Alan R. Liss 1987); *Flow Cytometry and Sorting* (M. Melamed et al. eds., Wiley-Liss 1990); the series *Methods in Enzymology* (Academic Press, Inc.); *Techniques in Immunocytochemistry,* (G. Bullock & P. Petrusz eds., Academic Press 1982, 1983, 1985, 1989); *Handbook of Experimental Immunology,* (D. Weir & C. Blackwell, eds.); *Cellular and Molecular Immunology* (A. Abbas et al., W.B. Saunders Co. 1991, 1994); *Current Protocols in Immunology* (J. Coligan et al. eds. 1991); the series *Annual Review of Immunology*; the series *Advances in Immunology; Oligonucleotide Synthesis* (M. Gait ed., 1984); and *Animal Cell Culture* (R. Freshney ed., IRL Press 1987).

As used herein, "a" or "an" means "at least one" or "one or more."

As used herein, "disease or disorder" refers to a pathological condition in an organism resulting from, e.g., infection or genetic defect, and characterized by identifiable symptoms. A disease or disorder associated with inflammation is any disease or disorder where inflammation is a cause (including a cause of increased severity) of the disease or the cause of a symptom of the disease, a prognostic marker (including marker of poor prognosis), a symptom, and effect, or a side-effect of treatment of the disease or disorder. Exemplary of diseases and disorders associated with inflammation are autoimmune diseases, allergy and asthma. A disease or disorder associated with immunosuppression is any disease or disorder where immunosuppression is a cause (including a cause of increased severity) of the disease or a cause of a symptom of the disease, a prognostic marker (including marker of poor prognosis), a symptom, and effect, or a side-effect of treatment of the disease or disorder, including diseases or disorders where the disease-causing cell type or pathogen evades the subject's immune system by directly or indirectly causing immunosuppression. Exemplary of immunosuppression-associated diseases are cancers.

As used herein, the term "autoimmune disease" refers, in part, any disorder in which loss of function or destruction of normal tissue arises from humoral or cellular immune responses to the body's own tissue constituents. Autoimmune diseases may be systemic, such as systemic lupus erythematosus, or organ specific, such as thyroiditis.

As used herein, the term "cancer" refers, in part, to any undesirable proliferation of cells, including malignant and non-malignant tumors, solid or fluid tumors, carcinomas, myelomas, sarcomas, leukemias, lymphomas, and other cancerous, neoplastic, or tumorigenic diseases.

As used herein, "Fc portion," and "Fc region" are well known terms in the art and generally refer synonymously to polypeptides containing the constant region of an immunoglobulin or structural or functional region thereof, such as one or more constant region domains of the immunoglobulin. In one example, the Fc region excludes the first constant region of the immunoglobulin. For example, the Fc region can contain the last two constant region Ig domains of IgA, IgD, or IgG or the last three constant region domains of IgE or IgM. The Fc region further can contain hinge regions. "Fc" can be used to refer to an isolated Fc region polypeptide, or to the Fc region in the context of an antibody, antibody fragment, or Fc fusion protein.

As used herein, "Fc gamma receptor," and "FcγR," refer synonymously to receptors that specifically bind to the Fc region of IgG molecules. The Fc gamma receptors can be naturally-occurring Fc receptors, which are expressed primarily in immune cells, or can be synthetically, e.g., recombinantly, produced Fc receptor polypeptides.

FcγRs can be broadly divided into two classes, namely the activating and inhibitory classes, depending on effects of binding to and signaling through the receptor. Activating FcγRs, include mammalian FcγRI, FcγRIIa, FcγRIII, and FcγRIV Inhibitory FcγRs include mammalian FcγRIIb.

As used herein, a physiological pH is a pH within a range of at or about 7.2 and at or about 8, and typically between at or about 7.4 and at or about 7.9, e.g., 7.2, 7.3, 7.4, 7.5, 7.6, 7.7, 7.8 or 7.9. The particular pH value can be specified.

As used herein, when a protein or portion is directly associated (e.g., bound) to another protein or portion, it is meant that the two proteins/portions associate without the presence of an intermediate, such as a linker or intermediate protein. For example, TGF-beta directly bound to an Ig protein does not contain an LAP intermediate.

As used herein, "activating-to-inhibitory ratio" and "A/I ratio" refer synonymously to a property of a protein, composition, or complex, which is calculated by determining the ratio of the binding affinity of that protein, composition or complex for an activating Fc receptor (for mammalian proteins, FcγRIII, FcγRIIa, and/or FcγRIV) to the affinity of the protein, composition or complex for the inhibitory Fc receptor (for mammalian proteins, FcγRIIB). The affinity for the respective receptors is determined using known experimental techniques (See, e.g., Nimmerjahn and Ravetch (*Science,* 310:1510-1512, 2005); Nimmerjahn et al. (*Immunity,* 23: 41-51 (2005); and Armour, K L et al., *Mol Immunol,* 40:585-593, 2003. For example, affinities ($K_A$) of proteins or complexes for FcγRs can be measured by surface plasmon resonance as described by Nimmerjahn and Ravetch (*Science,* 310:1510-1512, 2005) (see supplemental online materials)) or by other affinity-measuring techniques such as, but not limited to, those described herein and in references incorporated herein. The A/I ratio then is calculated by dividing the experimentally determined affinity for the activating receptor by the affinity for the inhibitory receptor.

"Individual" means any living organism, including humans and other mammals.

By "subject" is meant an organism to which the provided nucleic acid and amino acid molecules and complexes and compositions thereof can be administered. In one embodiment, the subject is a mammal or mammalian cell. Mammals include, but are not limited to, humans, and non-human animals, including farm animals, sport animals, rodents and pets.

As used herein, "Ig portion" refers to the part of the provided complexes (e.g., the TIGGs) that contain Immunoglobulin protein(s). The Ig portion can contain one or more Ig proteins, which typically are attached to the TGF-beta portion(s) of the complex. Typically, the association between the Ig portion and the TGF-beta portion is via non-covalent bond between the Ig protein(s) and TGF-beta protein(s).

As used herein "immunoglobulin protein" and "Ig protein" refer to whole immunoglobulin molecules and fragments thereof that retain at least part of the functional property of a whole Ig molecule, and in particular retain all or part of the Fc receptor binding affinity and specificity of the whole Ig molecule. For example, the Ig portions of the provided TIGG complexes contain Ig proteins that have all or part of the Fc receptor binding affinity of the corresponding full-length Ig molecules. The Ig proteins include naturally occurring and synthetic proteins, including variants and mimetics of naturally-occurring proteins.

As used herein, "TGF-beta portion" refers to the part of the provided complexes (e.g., the TIGGs) that contain TGF-beta protein(s). The TGF-beta portion can contain one or more TGF-beta proteins, which typically are attached to the Ig-portion(s) of the complex. Typically, the association between the Ig portion and the TGF-beta portion is via non-covalent bond between the Ig protein(s) and TGF-beta protein(s).

As used herein, "TGF-beta" can refer to any TGF-beta protein, including, but not limited to, TGF-beta 1, TGF-beta 2, and TGF-beta 3, including naturally occurring TGF-beta proteins and synthetic proteins, including variants and mimetics. In one provided embodiment, the TGF-beta (e.g., the TGF-beta portion of any of the provided complexes) is a TGF-beta 1, which is a polypeptide growth factor, such as the human TGF-beta 1. For example, in one aspect, the TGF-beta is the human TGF-beta 1 protein having monomers containing the sequence of amino acids set forth in SEQ ID NO:6. In another aspect, the TGF-beta is a TGF-beta protein having monomers containing at least at or about, or at or about, 70%, 75%, 80%, 85%, 90%, 95%, 96%, 97%, 98%, 99%, or 100% sequence identity with SEQ ID NO:6. In another aspect, the TGF-beta 1 includes monomers encoded by the sequence of nucleic acids set forth in SEQ ID NO:1. In another aspect, the TGF-beta includes monomers encoded by a sequence of nucleic acids having at least at or about, or at or about, 70%, 75%, 80%, 85%, 90%, 95%, 96%, 97%, 98%, 99%, or 100% sequence identity with SEQ ID NO:1.

As used herein, when a protein or complex or portion thereof has "TGF-beta activity," an in vivo or in vitro assay (that is known to measure the activity of TGF-beta) of that protein, complex or portion yields a positive result. For example, TGF-beta activity includes the ability to inhibit proliferation, growth, survival and/or differentiation of a cell type that is known to be inhibited by TGF-beta. The activity can be measured in an in vitro or in vivo assay, and can be expressed, for example, as a percentage of the readout of the assay for wild-type TGF-beta, such as TGF-beta dimers containing proteins of the amino acid sequence set forth in SEQ ID NO:6. Assays for measuring TGF-beta activity are well-known and include cell growth inhibition assays, soft agar assays and radioreceptor assays, and the cell-based PAI-1 promoter assay (wherein the (TGF-beta sensitive) promoter plasminogen activator inhibitor-1 is linked to the luciferase protein coding region and transfected into mink lung epithelial cells. Active TGF-beta is detected in solutions added to the cells in culture via luciferase activity expressed within cells (van Waarde, M A et al., *Anal Biochem* 247(1):45-51, 1997)). In one aspect provided herein, a protein, complex or portion contains at least at or about, or substantially the same, TGF-beta activity compared to a known protein, such as a wild-type TGF-beta. Such a determination is readily made through routine experimentation. An active TGF-beta protein exhibits TGF-beta activity, such as at or about the same, at least at or about the same, or substantially the same activity as a wild-type TGF-beta protein or as one of the TGF-beta proteins provided herein, such as TGF-beta proteins containing the sequence of amino acids set forth in SEQ ID NO:6.

As used herein, "Transforming Growth Factor-beta-bound IgG" and "TIGG" refer synonymously to complexes containing a TGF-beta portion and an Ig portion, containing TGF-beta protein(s) and Ig protein(s), respectively. The Ig protein(s) are IgG proteins, including full-length Ig molecules of the gamma isotype, and functional portions IgG molecules that retain all or part of the molecule's FcγR binding specificity, such as, but not limited to Fc portions of IgG molecules, and include naturally occurring and synthetic proteins, such as variants. Typically, the TGF-beta portion and the Ig portion are associated via a non-covalent bond. Typically, the TGF-beta portion is a dimer, such as a 25 kD mature TGF-beta dimer or variant thereof.

If it is desired to target receptors that bind to isotypes other than Fc-gamma receptors, any of the TIGGs provided herein can be modified by replacing the IgG portion with an Ig protein(s) of another isotype to create complexes provided herein of other isotypes. Similarly, IgG protein variants in the TIGG complex can include Fc portions of other isotype antibodies that have been modified to render them specific for one or more Fc gamma receptor.

An "Activating Transforming Growth Factor-beta-bound IgG" (or "AcTIGG") is a TIGG complex having a higher binding affinity and/or specificity for inhibitory FcγRs compared to activating FcγRs, and thus having a relatively low A/I ratio that is less than at or about 1, such as less than at or about 0.9, 0.8, 0.7, 0.6, and typically less than at or about 0.5, such as 0.4, 0.3, 0.2, 0.1, 0.09, 0.08, 0.07, 0.06, 0.05, 0.04, 0.03, 0.02, 0.01, 0.009, 0.005, or 0.001. Thus exemplary of the AcTIGG are TIGG complexes where the Ig portion has a relatively low A/I ratio, such as Ig portions containing all or a functional part of human IgG4 or mouse IgG1 or a functional variant thereof. AcTIGGs can be used to treat subjects, for example, to reduce tumor burden or metastasis, treat cancer and to promote an immune response in a subject.

An "Inhibiting Transforming Growth Factor-beta-bound IgG" (or "InTIGG") is a TIGG complex having a higher binding affinity and/or specificity for activating FcγRs compared with inhibitory FcγRs and thus having a high A/I ratio that is at least at or about 2, such as at or about 2, 3, 4, 5, 6, 7, 8, 9, 10, 11, 12, 13, 14, 15, 16, 17, 18, 19, 20, 25, 30, 35, 40, 45, 50, 55, 60, 65, 70, 80 or 90 or greater. Thus, exemplary of the InTIGGs are complexes where the Ig portion contains all or a functional part of an IgG having a relatively high A/I ratio, such as, but not limited to, human IgG1, IgG2, IgG3, or any combination of the three, or total human gamma globulin (available commercially as "IVIG") and mouse IgG2a and IgG2b, and functional portions and variants thereof.

As used herein, when it is generally stated that a polypeptide or nucleic acid molecule or region thereof contains or has "identity" or "homology," per se (without specifying a particular percent identity), to another polypeptide or nucleic acid molecule or region thereof, the two molecules and/or regions share at least at or about 40%, and typically at least at or about 50%, 60% or 70% sequence identity, such as at least at or about 60%, 65%, 70%, 75%, 80%, 85%, 90%, 95%, 96%, 97%, 98%, 99% or 100% sequence identity. The precise percentage of identity can be specified.

Sequence "identity" has an art-recognized meaning. The percentage of sequence identity between two nucleic acid or polypeptide molecules and/or regions can be calculated using well-known and published techniques, such as those described below. In general, for determination of the percentage sequence identity, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carrillo et al. (1988) *SIAM J Applied Math* 48:1073). For sequence identity, the number of conserved amino acids or nucleotides is determined by standard alignment algorithms programs, and can be used with default gap penalties established by each supplier. Substantially homologous nucleic acid molecules specifically hybridize typically at moderate stringency or at high stringency all along the length of the nucleic acid of interest.

The term "identity," when associated with a particular number, represents a comparison between the sequences of a first and a second polypeptide or polynucleotide or regions thereof. As used herein, the term at least "90% identical to" refers to percent identities from 90 to 99.99 of one nucleotide or amino acid sequence to the other. Identity of 90% or more is indicative of the fact that, assuming for exemplification purposes, the full length of a first and second polypeptide, each 100 amino acids in length, are compared, no more than 10% (i.e., 10 out of 100) of the amino acids in the first polypeptide differs from that of the second polypeptide. Similar comparisons can be made between first and second polynucleotides. Such differences among the first and second sequences can be represented as point mutations randomly distributed over the entire length of a polypeptide or they can be clustered in one or more locations of varying length up to the maximum allowable, e.g., 10/100 amino acid difference (approximately 90% identity). Differences are defined as nucleotide or amino acid residue substitutions, insertions, additions or deletions. At the level of homologies or identities above about 85-90%, the result should be independent of the program and gap parameters set; such high levels of identity can be assessed readily, often by manual alignment without relying on software.

Sequence identity can be measured along the full length of a polynucleotide or polypeptide or along a region of the molecule. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptides, the term "identity" is well known to skilled artisans (Carrillo, H. & Lipman, D., *SIAM J Applied Math* 48:1073 (1988)). Sequence identity compared along the full length of two polynucleotides or polypeptides refers to the percentage of identical nucleotide or amino acid residues along the full-length of the molecule. For example, if a polypeptide A has 100 amino acids and polypeptide B has 95 amino acids, which are identical to amino acids 1-95 of polypeptide A, then polypeptide B has 95% identity when sequence identity is compared along the full length of a polypeptide A compared to full length of polypeptide B. Alternatively, sequence identity between polypeptide A and polypeptide B can be compared along a region, such as a 20 amino acid analogous region, of each polypeptide. In this case, if polypeptide A and B have 20 identical amino acids along that region, the sequence identity for the regions would be 100%. Alternatively, sequence identity can be compared along the length of a molecule, compared to a region of another molecule. As discussed below, and known to those of skill in the art, various programs and methods for assessing identity are known to those of skill in the art. High levels of identity, such as 90% or 95% identity, readily can be determined without software.

Whether any two nucleic acid or polypeptide molecules have sequences that contain, or contain at least, a certain percent (e.g., 60%, 70%, 80%, 85%, 90%, 95%, 96%, 97%, 98% or 99%) sequence identity can be determined using known computer algorithms such as the "FASTA" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Altschul, S. F., et al., *J Molec Biol* 215: 403 (1990); *Guide to Huge Computers*, Martin J. Bishop, ed., Academic Press, San Diego, 1994, and Carrillo et al. (1988) *SIAM J Applied Math* 48:1073). For example, the BLAST function of the National Center for Biotechnology Information database can be used to determine identity.

Other commercially or publicly available programs include DNAStar "MegAlign" program (Madison, Wis.) and the University of Wisconsin Genetics Computer Group (UWG) "Gap" program (Madison Wis.)). The extent of sequence identity (homology) and complementarity may be determined using any computer program and associated parameters, including those described herein, such as BLAST 2.2.2. or FASTA version 3.0t78, with the default parameters. It is understood that for the purposes of determining sequence identity among DNA and RNA sequences thymidine nucleotide is equivalent to (represents identity with) a uracil nucleotide. Percent identity further can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *Atlas Of Protein Sequence And Structure*, National Biomedical Research Foundation, pp.

353-358 (1979); (2) a penalty of 3.0 for each gap and an additional 0.10 penalty for each symbol in each gap; and (3) no penalty for end gaps.

Throughout this disclosure, various provided aspects are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

The terms "nucleic acid" and "nucleic acid sequence" refer to oligonucleotides, nucleotides, polynucleotides, and fragments of any of these, including DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin. The term encompasses nucleic acids, i.e., oligonucleotides, containing known analogues of natural nucleotides, naturally occurring nucleic acids, synthetic nucleic acids, and recombinant nucleic acids.

"Recombinant," as applied to a polynucleotide, means that the polynucleotide is the product of various combinations of cloning, restriction and/or ligation steps, and other procedures that result in a construct that is distinct from a polynucleotide found in nature.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266: 19867-19870 (1991)) can be inserted immediately 5' of the start codon and may enhance expression. The desirability of (or need for) such modification may be empirically determined.

In one aspect, the term "transformation" refers to the transfer of a nucleic acid sequence into the genome of a host cell, resulting in genetically stable inheritance. A "host cell" is a cell that has been transformed, or is capable of transformation, by an exogenous nucleic acid molecule. Host cells containing the transformed nucleic acid sequences are referred to as "transgenic" cells, and organisms comprising transgenic cells are referred to as "transgenic organisms". The terms "transformed", "transduced", "transgenic", and "recombinant" refer to a host cell or organism into which a heterologous nucleic acid molecule has been introduced. The nucleic acid molecule can be stably integrated into the genome generally known in the art and are disclosed in Sambrook and Russell, infra. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available (see, e.g., the various references cited below). In one aspect, a vector comprises both the polynucleotide encoding the agonist monomer and the polynucleotide encoding the antagonist monomer.

A "recombinant viral vector" refers to a viral vector comprising one or more heterologous genes or sequences. Since many viral vectors exhibit size-constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation) (see, e.g., the references and illustrations below). Modified viral vectors in which a polynucleotide to be delivered is carried on the outside of the viral particle have also been described (see, e.g., Curiel, D T, et al. *PNAS* 88: 8850-8854, 1991).

Viral "packaging" as used herein refers to a series of intracellular events that result in the synthesis and assembly of a viral vector. Packaging typically involves the replication of the "pro-viral genome", or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" genes, found in many viral genomes, are genes encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain genes encoding the missing functions which can be supplied in trans). For example, such packaging genes can be stably integrated into a replicon of the packaging cell line or they can be introduced by transfection with a "packaging plasmid" or helper virus carrying genes encoding the missing functions.

The term "overexpression" refers to the level of expression in transgenic cells or organisms that exceeds levels of expression in normal or untransformed cells or organisms.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance.

Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in vitro systems designed to test or use such activities.

As used herein, "production by recombinant means" refers to production methods that use recombinant nucleic acid methods that rely on well-known methods of molecular biology for expressing proteins encoded by cloned nucleic acids.

As used herein, "substantially identical" to a product means sufficiently similar so that the property of interest is sufficiently unchanged so that the substantially identical product can be used in place of the product.

As used herein, "equivalent," when referring to two sequences of nucleic acids means that the two sequences in question encode the same sequence of amino acids or equivalent proteins. It also encompasses those that hybridize under conditions of moderate, preferably high stringency, whereby the encoded protein retains desired properties.

As used herein, when "equivalent" is used in referring to two proteins or peptides, it means that the two proteins or peptides have substantially the same amino acid sequence with only conservative amino acid substitutions that do not substantially alter one or more activities or functions of the protein or peptide.

When "equivalent" refers to a property, the property does not need to be present to the same extent [e.g., two peptides can exhibit different rates of the same type of enzymatic activity], but the activities are preferably substantially the same. "Complementary," when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows: 1) high stringency: 0.1×SSPE, 0.1% SDS, 65° C.; 2) medium stringency: 0.2× SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

The terms "polypeptide," "peptide," and "protein" are used interchangeably to refer to polymers of amino acids of any length. These terms also include proteins that are post-translationally modified through reactions that include glycosylation, acetylation and phosphorylation.

As used herein, a "fragment thereof" "region thereof" and "portion thereof" refer to fragments, regions and portions that substantially retain at least one function of the full length polypeptide.

The terms "mimetic", peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif, including, but not limited to, Fc portion or region thereof that specifically binds to an Fc receptor).

Peptide mimetics include recombinantly and chemically modified peptides, and non-peptide agents. Knowing the binding and structural features of the provided TIGG complexes and proteins thereof, one of skill in the art can design peptidomimetics having equivalent, or substantially equivalent, structure and/or function, such as, for example, the same, about the same, or greater binding affinity, or and A/I that is the same, about the same, or greater, or the same, about the same, or lower, compared to a given molecule or complex, such as compared to a native IgG molecule. The mimetics include those entirely composed of synthetic, non-natural analogues of amino acids, and chimeric molecules composed of natural peptide amino acids and non-natural analogs of amino acids. The mimetics further include polypeptide incorporating conservative amino acid substitutions, as long as such substitutions also do not substantially alter the mimetic's structure and/or activity.

The polypeptides and peptides provided herein, and polypeptides and peptides used in the provided complexes, compositions, combinations and methods, can contain "mimetic" ("peptidomimetic") forms.

As used herein, a variant of a polypeptide (protein) or polynucleotide (namely a parent polypeptide or polynucleotide) is a protein or polynucleotide that contains one or more alterations in the amino acid or nucleic acid sequence, respectively, compared to the amino acid sequence of the parent polypeptide or the nucleic acid sequence of the parent polynucleotide. Alterations in sequences include substitutions, including conservative substitutions, deletions, additions and insertions, compared to the sequence of the polypeptide or polynucleotide of interest. A "conservative" amino acid substitution is a substitution of an amino acid having similar structural or chemical property compared to the corresponding amino acid in the parent polypeptide. Non-conservative amino acid substitutions are those where the charge, hydrophobicity and/or bulk of the amino acid is substantially altered. Typically, a variant polypeptide has at least 75% sequence identity, and preferably at least 80%, 85%, 90%, 95%, or 95% sequence identity sequence identity, to the basic sequence. There may be at least 80%, for example at least 85%, 90% or 95%, amino acid identity over a stretch of 40 or more, for example 60, 80, 100 or more, contiguous amino acids ("hard homology").

Variants of polypeptides may be generated by conventional techniques, including either random or site-directed mutagenesis of DNA encoding the polypeptide. The resultant DNA fragments are then cloned into suitable expression hosts such as *E. coli* or mammalian cells using conventional technology and clones that retain the desired activity are detected. The term "variant" also includes naturally occurring allelic variants. For example, TGF-beta 1, TGF-beta 2 and TGF-beta 3 are all variants for the purposes of this application, in that their amino acid sequences are greater than 85% identical.

The variants and mimetics can be described in terms of the degree of amino acid or nucleotide sequence identity compared to the parent polypeptide or polynucleotide. For example, variants include polypeptides and polynucleotides with at least at or about 50%, 60%, and typically at least at or about 70%, 80%, 90%, 91%, 92%, 93%, 94%, 95%, 96%, 97%, 98%, 99% or more sequence identity to the parent polypeptide or polynucleotide. Typically, the variants further retain a substantial amount of one or more structural or functional properties of the parent polypeptide or polynucleotide, or compared to another reference polypeptide or polynucleotide such as a wild-type protein or polynucleotide (e.g., a wild-type IgG or TGF-beta protein). The particular property can be specified, along with the desired similarity to the parent or other protein. For example, the TGF-beta-Ig complexes (e.g., TIGG) and portions thereof include variants (e.g., variants having a particular sequence identity to a parent molecule) that have a substantially similar, greater, or lower binding affinity for a particular FcR, or similar or greater or lesser A/I ratio compared to the parent molecule or complex, or compared to a different molecule or complex, such as a wild-type protein (e.g., a wild-type IgG molecule).

For members of a class of variants defined as having a particular percent identity or at least a particular percent identity, routine experimentation can be used to determine that the variant is within the scope of the provided embodiment, i.e., that the member of the class has a particular function or structure, e.g., binding affinity, for example, that the structure and/or function is not substantially altered compared to the parent polypeptide or polynucleotide or other molecule.

In another embodiment, the variant polypeptides include polypeptides sharing a specified sequence identity with parent polypeptides, and also having at least at or about a particular A/I ratio, or less than at or about a particular A/I ratio. For example, in one embodiment, the AcTIGGs include variants having A/I ratios less than 1, such as less than at or about 0.9, 0.8, 0.7, 0.6, and typically less than at or about 0.5, such as 0.4, 0.3, 0.2, 0.1, 0.09, 0.08, 0.07, 0.06, 0.05, 0.04, 0.03, 0.02, 0.01, 0.009, 0.005, or 0.001. In another embodiment, the InTIGGs include variants having A/I ratios at least at or about 2, such as at or about 2, 3, 4, 5, 6, 7, 8, 9, 10, 11, 12, 13, 14, 15, 16, 17, 18, 19, 20, 25, 30, 35, 40, 45, 50, 55, 60, 65, 70, 80 or 90 or greater.

"Derivative" refers to a polypeptide or polynucleotide that has been derived from a parent polynucleotide or polypeptide the basic sequence by modification, for example by conjugation or complexing with other chemical or protein moieties or by post-translational modification techniques as would be understood in the art. Such derivatives include amino acid deletions and/or additions to polypeptides or variants thereof wherein said derivatives retain activity of the basic protein.

Other derivatives include modification to side chains, incorporation of unnatural amino acids and/or their derivatives during peptide, polypeptide or protein synthesis and the use of crosslinking agents.

As used herein, a "composition" refers to any mixture of two or more products or compounds. It may be a solution, a suspension, liquid, powder, a paste, aqueous, non-aqueous or any combination thereof.

"Therapeutic composition" is defined as comprising AcTIGG or InTIGG and a pharmaceutically acceptable carrier.

As used herein, "potency" is a measure of the relative amount of a composition required to produce a specific effect; the more potent the composition, the smaller the amount required to produce the effect.

As used herein, a "combination" refers to any association between two or among more items.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. See e.g., *Remington: The Science and Practice of Pharmacy* 20th Ed. (Lippincott, Williams & Wilkins 2003). Except insofar as any conventional media or agent is incompatible with the active compound, such use in the compositions is contemplated.

The term "therapeutically effective amount" as used herein, means that amount of InTIGG or AcTIGG that elicits the biological or medicinal response in a tissue system, animal or human that is being sought by a researcher, veterinarian, medical doctor or other clinician, which includes alleviation of one or more symptoms of the disease or disorder being treated, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

The total dose required for each treatment can be administered by multiple doses or in a single dose. The pharmaceutical composition can be administered alone or in conjunction with other pharmaceuticals directed to the pathology, or directed to other symptoms of the pathology.

B. TGF-BETA PROTEINS, COMPLEXES CONTAINING TGF-BETA PROTEINS, AND METHODS OF USE

Cancer is a deadly disease that affects millions of individuals worldwide. The effectiveness of current treatments vary according to tumor type, the stage at which the tumor is treated, age and health of the patient, and many other parameters. It is known, however, that many if not most cancers are accompanied by tumor specific immune suppression. For example, there is growing evidence that the microenvironment of tumors are overabundant in tumor-associated macrophages (TAMs) and myeloid-derived suppressor cells (MDSCs). These cells of myeloid origin and M2 phenotype, help to create an immunosuppressive environment that dampens anti-tumor immune responses.

Autoimmune diseases are debilitating and sometimes deadly diseases which affect millions of individuals worldwide. The effectiveness of current treatments vary according to disease type, the stage at which the disease is treated, age and health of the patient, and other parameters Immune-mediated inflammation and tissue destruction are the hallmarks of autoimmune diseases, including rheumatoid arthritis. For example, inflammatory macrophages (e.g., M1 phenotype macrophages) and B cells contribute to both inflammation and tissue destruction in RA.

Methods and compositions are needed to target autoimmune and inflammatory diseases and cancer. In particular, therapies are needed that have specificity for particular cell types associated with a particular disease. Because of their immunosuppressive and chemotactic properties, TGF-beta proteins are attractive candidates for use in protein therapeutics where modulation of immune cells is desired. For example, the plurality of inflammatory immune cell types associated with inflammatory and autoimmune diseases ((e.g., M1 phenotype macrophages, B-lymphocytes, T-lymphocytes and other inflammatory cells) are suppressed by TGF-beta. Similarly, immune cells that promote immunosuppression in tumors (e.g., tumor-associated macrophages (TAMs) and myeloid-derived suppressor cells (MDSCs), both of myeloid origin and M2 phenotype), can be suppressed by TGF-beta.

Available TGF-beta proteins, however, are limited. For example, available TGF-beta proteins can have low potency and activity, and can have relatively short half-lives in vivo. Further, available TGF-beta proteins have pleiotropic effects on a plurality of immune system cells. TGF-beta proteins that can specifically target particular cell types and thereby mediate particular effects on cancer and autoimmunity are needed.

The provided TGF-beta proteins and complexes overcome these limitations. Among the provided proteins and complexes are targeted proteins and complexes (e.g., dimers and multimers), for example, TGF-beta proteins complexed (e.g., non-covalently bound) to other proteins, such as immunoglobulin molecules and portions thereof. The provided proteins and complexes can suppress immune cells expressing receptors for TGF-beta.

Cells targeted for suppression by the provided proteins include, but are not limited to, immune cells in a subject that are drawn to the site of the administered (e.g., injected) protein or complex, via the natural chemotactic properties of TGF-beta. Alternatively, the targeted cells are cells that encounter the proteins or complexes in vivo in the lymph or circulatory system, such as cells expressing Fcγ receptors, for example, particular ratios of activating versus inhibitory FcγR. These immune cells may include B cells, monocytes, PMNs, mast cells, and neutrophils, among others. The provided TGF-beta containing complexes can be targeted to particular immune cell types. For example, in one embodiment, the immunoglobulin portion of the TGF-beta complex targets the TGF-beta to particular cell types based on the relative affinities of the Fc portion of the Ig for particular Fc receptors, such as the relative affinity for activating versus inhibitory Fc receptors (A/I ratio). For example, in one aspect, the complexes (e.g., AcTIGG complexes) target and suppress immune cells that express a relatively higher amount (or express only or predominantly) activating FcγRs. In another aspect, the complexes (e.g., InTIGG complexes) target and suppress immune cells that express a relatively higher amount (or express only or predominantly) inhibitory FcγRs. In one aspect, the provided proteins and complexes are injectable therapeutic protein complexes.

Also provided are polynucleotides encoding the proteins and complexes, such polynucleotides encoding the TIGG complexes and the TGF-beta and Ig portions of the TIGGs. In one aspect, the polynucleotides are contained within an expression vector, including, but not limited to, viral vectors. In one aspect, the vector is contained within a host cell. Also provided are host cells containing the vectors and methods for producing the TIGGs, the TGF-beta and immunoglobulin or portion thereof, by culturing host cells containing the expression vectors under conditions sufficient for the production of the TGF-beta-bound immunoglobulin, and recovering the TGF-beta-bound immunoglobulin.

Also provided are compositions (e.g., pharmaceutical compositions) and combinations containing the proteins and complexes, and therapeutic formulations of the complexes. The pharmaceutical compositions include, but are not limited to, compositions containing TGF-beta-bound immunoglobulin and a pharmaceutically acceptable carrier, and compositions containing a vector with a polynucleotide that encodes a TGF-beta-bound immunoglobulin in admixture with a pharmaceutically acceptable carrier.

The proteins, complexes, compositions and combinations can be used in treating and diagnosing various therapeutic indications. For example, the provided complexes and compositions can be used to treat diseases, such as autoimmune diseases, inflammatory diseases, and cancers. Also provided are methods for producing the proteins and complexes, and methods for their use, for example, in disease treatment and diagnosis. For example, provided are methods for treating cancer or autoimmune disease in a subject, comprising administering a therapeutically effective amount of the provided pharmaceutical composition to a subject. The provided pharmaceutical compositions can be used to treat cancer or autoimmune diseases, either in vitro or in vivo.

i. TGF-Beta

TGF-beta proteins are members of a superfamily of structurally similar regulatory proteins, including, but not limited to, the mammalian TGF-beta 1, 2, and 3, and active/inhibin and bone morphogenic proteins. Mature TGF-beta typically exists as a homodimer, such as the dimeric mature TGF-beta molecule, containing two covalently associated TGF-beta molecules. TGF-beta proteins further include latent TGF-beta complexes, such as complexes containing latency-associated proteins (LAP). For example, the latent complexes include the naturally occurring inactive complex containing two covalently linked latency-associated proteins (LAP) non-covalently linked to the dimeric mature TGF-beta molecule, which can be activated by dissociation of the LAP or by conformational changes in the complex, such as by binding of LAP to either thrombospondin or $\alpha v\beta 6$ integrin.

Active TGF-beta dimmers can specifically bind to TGF-beta Receptor II (TGF-beta RII), and typically bind two TGF-beta RII molecules. Binding by the TGF-beta homodimer recruits two TGF-beta Receptor I (TGF-beta RI) molecules, forming a heteromeric complex. Downstream signaling is mediated by the bound TGF-beta RI, a serine-threonine kinase, which is phosphorylated upon complexation to the TGF-beta/TGF-beta RII complex. Activation of TGF-beta RI causes phosphorylation of Smad2 and Smad3 and induces their heterodimerization with Smad4. The activated Smad complex then translocates to the nucleus where it regulates gene transcription.

TGF-beta regulates a plurality of processes, including cell differentiation and proliferation, migration, motility, deposition of the extracellular matrix, cell death, and immunosuppression. TGF-beta signaling can increase the synthesis of matrix proteins, such as vitronectin, fibronectin, laminin, tenascin, proteoglycans, and collagens, enhance the expression of cell adhesion molecules such as integrins, and increase the synthesis of various protease inhibitors. It also can decrease the synthesis of matrix degrading proteases.

Active TGF-beta proteins have immunosuppressive activities, for example, having inhibitory effects on several major immune system cell types, including T-cells (both $CD4^+$ and $CD8^+$), B lymphocytes, monocytes, macrophages, dendritic cells, polymorphonuclear leukocyte. Additionally, active TGF-beta can be a powerful chemoattractant for a plurality of types of immune cells, including T-cells (both $CD4^+$ and $CD8^+$), monocytes, PMNs, neutrophils and mast cells.

ii. Immunoglobulins and Fc Receptors

In one embodiment, the provided TGF-beta complexes (e.g., dimers and multimers) have Ig portions that contain Immunoglobulin (Ig) molecules (Ig proteins), including, but not limited to, IgG molecules, and portions of Ig molecules, such as Fc regions of IgG molecules. In one aspect, the Ig in the complex targets the complex to a particular cell type, such as a cell type expressing a relatively higher ratio of activating or inhibitory Fc receptors.

Variable regions of Ig molecules (and in particular, complementary-determining regions (CDRs) contribute to antigen specificity and binding. Ig constant regions, on the other hand, are less variable among different immunoglobulin (Ig) molecules and serve other functions, including antibody effector functions. Natural full length Ig molecules contain between three and four constant region Ig domains.

The constant region of a full-length immunoglobulin includes an Fc region, which typically includes the constant region domains, excluding the first constant region domain. Immunoglobulins of a particular isotype (classes: IgG, IgM, IgA, IgE, IgD and sub-classes thereof) can be characterized by particular effector functions and constant regions having similar basic structures/sequences. Human Ig classes and subclasses include IgG (including IgG1, IgG2, IgG3, IgG4), IgM, IgA (including IgA1, IgA2), IgE and IgD.

Fc receptors are cell surface receptors, expressed on various immune cell types, that specifically bind Fc regions of immunoglobulin molecules. Fc receptors are generally categorized according to the class of Ig molecule they recognize. For example, Fc gamma receptors (Fc$\gamma$R) bind Fc portions of IgG molecules. Mammalian Fc gamma receptors are further classified into four classes (Fc$\gamma$RI (CD64), Fc$\gamma$RII (CD32), Fc$\gamma$RIII (CD16) and Fc$\gamma$RIV). The Fc$\gamma$RII class further includes the functionally distinct Fc$\gamma$RIIa and Fc$\gamma$RIIb subtypes. FcgRI has a high affinity for IgG Fc regions, can bind monomeric IgG at physiological concentrations of IgG, and has a restricted isotype specificity. Fc$\gamma$II and Fc$\gamma$III receptors have low affinities for IgG Fc regions and typically only can bind multimeric IgG (for example, immune complexes and dimeric IgG) at physiological IgG concentrations.

Fc receptors, particularly Fc gamma receptors, can also be categorized into two functional classes: activating Fc receptors (including Fc$\gamma$RI, Fc$\gamma$RIIa, Fc$\gamma$RIII and Fc$\gamma$RIV) and inhibitory Fc receptors (including the sole naturally occurring inhibitory Fc receptor, Fc$\gamma$RIIb). Activating Fc$\gamma$Rs are expressed on all myeloid cells, and their cross-linking results in sustained cellular responses. With the exception of T cells and NK cells, Fc$\gamma$RIIb is expressed in all cells of the immune system. When properly bound, Fc$\gamma$RIIb inhibits activation and proliferation of the cell in which it is expressed.

Different cells of the immune system express different ratios of activating versus inhibitory Fc$\gamma$Rs. Skewing the balance between activating and inhibiting Fc$\gamma$Rs has been correlated with the pathophysiology of autoimmune diseases in patients (Wijngaarden et al., *Arthrit. & Rheum.* 50(12):3878-3887, 2004) and antitumor immune response in animal models (Dhodapkar, K. M., *PNAS* 102:941-951, 2005). In the former study, rheumatoid arthritis patients were found to have an increased ratio of activating Fc$\gamma$Rs relative to healthy patients, whereas the latter study showed that blocking the inhibitory Fc$\gamma$R on dendritic cells increased antitumor immune responses.

The M1 (activating, inflammatory) and M2 (inhibitory) classes of monocyte-lineage cells (e.g., macrophages) are based on function and on expression patterns of proteins including cytokines, chemokines, surface receptors, apoptosis-related genes, soluble carriers, enzymes, extracellular mediators, and DNA binding factors. For example, M1 macrophages express 212 times more CXCL11 chemokine as inhibitory macrophages (M2), whereas inhibitory macrophage express 38 times more CCL13 than activating macrophages (Martinez, F O et al, *J Immunol* 177:7303-7311, 2006). M1 macrophages express and secrete greater than 50-fold more CXCL11, CCL19, CXCL10, and CXCL9 compared to M2. CCL13, CCL18, and CCL23 expression is more than 10-fold higher in M2 macrophages compared to M1. Among membrane proteins, over 100-fold more CCR7 receptor is expressed in M1 vs M2, and mannose receptor C type 1 is expressed 43 times more in M2 vs M1 macrophages. Differentiation of M1 versus M2 macrophages is well established and has been verified and extensively characterized based on different cytokine secretion profiles following *E. coli* lipopolysaccharide (LPS) challenge. After LPS challenge in culture, M1 macrophages overproduce tumor necrosis factor-alpha (TNF-alpha) and interferon-gamma (IFN-$\gamma$), whereas M2 macrophages overproduce monocyte chemotactic protein-1 (MCP-1) and interleukin-10 (IL-10) (See, for example, Stout, R D, et al., *J Immunol* 175:342-349, 2005).

While different immune cell types have varying relative expression levels of activating versus inhibitory Fc receptors, different FcγRs also have varying affinities for particular subclasses of IgG molecules. For example, Nimmerjahn and Ravetch (*Science,* 310:1510-1512, 2005) reported that although all FcγRs can bind IgG immune complexes, individual Fcγ receptors display significantly different affinities for different IgG subclasses. This report described the different affinities of particular IgG subclasses for functionally different Fcγ receptors as activating-to-inhibitory (A/I) ratios (ratio of the affinity of each IgG subclass for activating Fcγ receptors (sFcγRIII or sFcγRIV) compared to its affinity for the inhibitory receptor FcγRIIB). The ratio, calculated based on affinities determined through in vitro binding to Fcγ receptors, accurately predicted the efficacy of particular IgG subclasses to mediate immune function. For example, the ratio could predict the ability of specific isotypes of anti-tumor antibodies with identical CDRs (and thus, identical antigen specificity), to mediate immune effector responses.

Differential efficiency of binding by various IgG subtypes to inhibitory and activating Fcγ receptors also has been described in humans (Armour, K L et al., *Mol Immunol,* 40:585-593, 2003; Bruhns, P. et al., *Blood* Nov. 18, 2008, Epub ahead of print).

Other reports have verified that efficacy of antibody function can be attributed to differential binding by FcγR to activating and inhibiting receptors. Using site-directed mutagenesis of the IgG Fc region of anti-tumor antibodies, three groups (Lazar, G A et al., *PNAS,* 103(11):4005-4010; Richards, J O et al., *Mol Cancer Ther,* 7(8):2517-2527; Stavenhagen, J B et al., *Cancer Res,* 67(18):8882-8890) showed that mutants having increased binding affinity for activating FcγR receptors, and/or decreased binding affinity for inhibitory FcγR, improved the efficacy of anti-tumor antibodies.

Differential efficiency of binding by various IgG subtypes to inhibitory and activating Fcγ receptors has been described in humans (Armour, K L et al., *Mol Immunol,* 40:585-593, 2003; Bruhns, P. et al., *Blood* Nov. 18, 2008, Epub ahead of print). Using the affinity data from these reports, the approximate A/I ratio for natural (wild-type) human IgG subtypes interacting with human FcγRs is as follows: IgG1, ~15-20; IgG2, ~5-8; IgG3 ~10; and IgG4 ~0.1-0.3. IgG1, IgG2, and IgG3 have higher relative affinities to activating FcγRs, whereas IgG4 has a higher relative affinity to inhibitory FcγRs. The approximate normal distribution of IgG subtype percent concentrations in human blood and in intravenous immunoglobulin (IVIG) in humans and given to patients is 60% IgG1, 30% IgG2, 6% IgG3, and 4% IgG4.

In one embodiment, the A/I ratio of the Fc or Ig (e.g., IgG) portion of the provided complexes can be specified. For example, provided are complexes with Ig molecules or portions thereof having an A/I ratio that is between at or about 90 and at or about 0.001, and can be greater than 90 or less than 0.001, and typically is between at or about 80 and at or about 0.001 or between at or about 70 and at or about 0.001, for example, at or about 0.001, 0.002, 0.005, 0.01, 0.02, 0.03, 0.04, 0.05, 0.06, 0.07, 0.08, 0.09, 0.1, 0.2, 0.3, 0.5, 0.6, 0.7, 0.8, 0.9, 1, 2, 3, 4, 5, 6, 7, 8, 9, 10, 11, 12, 13, 14, 15, 20, 25, 30, 35, 40, 45, 50, 55, 60, 65, 70, 80 or 90. In one aspect, for example, when the complex is an InTIGG, the A/I ratio is greater than at or about 2, 3, 4, or 5, and typically greater than at or about 8, for example, at or about or greater than at or about 8, 9, 10, 11, 12, 13, 14, 15, 20, 25, 30, 35, 40, 45, 50, 55, 60, 65, 70, 80 or 90, or more. In another aspect, for example, when the complex is an AcTIGG, the A/I ratio is less than at or about 1, e.g., at or about or less than at or about 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, or less.

iii. Complexes, Including TGF-Beta—IgGs (TIGGs)

Among the provided proteins and complexes are TGF-beta-IgGs (TIGGs), which are proteins and complexes containing a TGF-beta portion (containing one or more TGF-beta protein, such as a TGF-beta dimer) associated with an Ig portion (containing one or more Ig protein). For example, the provided TIGGs include those containing one, or more than one, IgG molecule bound to a TGF-beta, for example, to a TGF-beta dimer. The TGF-beta protein(s) typically are associated with the Ig protein(s) via non-covalent bond. The Ig proteins include full-length immunoglobulins, such as IgG, and functional regions and portions of full-length Ig molecules, such as constant regions and Fc regions and functional portions thereof. The provided compositions include isolated TIGGs, such as, but not limited to, isolated multimer complexes in which the 25 kD dimeric protein TGF-beta 1 is noncovalently bound to an immunoglobulin G protein or to two immunoglobulin G proteins.

The TIGGs can be used to target cells of the immune system, such or treating cancer and autoimmunity. The TIGGs include, but are not limited to activating TIGGs (AcTIGGs) and inhibiting TIGGs (InTIGGs), which target for suppression cells expressing higher relative amounts of inhibitory and activating FcγRs, respectively. Thus, the TIGGs typically are defined in part by functional properties, such as their ability to bind and target particular cell types, e.g., by binding to particular FcγRs.

Accordingly, the binding affinity of the TIGG for other molecules, typically for Fc receptors, can be specified. The affinity can be measured using well known methods, such as those described herein (see, e.g., subsection vii below), and expressed using well-known units of affinity (e.g., $K_a$, $K_d$, $K_D$). Typically, the affinity is specified by expressing a ratio or percentage of the affinity of the TIGG for the molecule, compared to the affinity of another Ig protein or complex for that molecule (e.g., for a particular Fc receptor), or compared to the affinity of the TIGG for another molecule (e.g., for a different type of Fc receptor, as in an activating-to-inhibitory (A/I) ratio). For example, the TIGGs include AcTIGGs, having A/I ratios less than at or about 1, such as less than at or about 0.9, 0.8, 0.7, 0.6, and typically less than at or about 0.5, such as 0.4, 0.3, 0.2, 0.1, 0.09, 0.08, 0.07, 0.06, 0.05, 0.04, 0.03, 0.02, 0.01, 0.009, 0.005, or 0.001. The TIGGs further include InTIGGs, having A/I ratios at least at or about 2, such as at or about 2, 3, 4, 5, 6, 7, 8, 9, 10, 11, 12, 13, 14, 15, 16, 17, 18, 19, 20, 25, 30, 35, 40, 45, 50, 55, 60, 65, 70, 80 or 90 or greater.

a. Naturally Occurring and Purified TGF-Beta—IgG Complexes

Naturally-occurring TGF-beta bound IgG in vivo has been reported. For example, complexes containing TGF-beta and IgG were isolated from the MRL/lpr mouse model of systemic lupus erythematosis (Caver, T E, et al., ibid) and the B16 melanoma mouse model (Harada et al., ibid). Further, IgG fractions, isolated from two SLE patients during active disease, were consistent with TGF-beta-bound IgG.

Most reports of naturally occurring TGF-beta-bound IgG have suggested that the association of the two proteins occurs through a latency associated protein (LAP) intermediate. The latent, inactive form of TGF-beta contains two LAP molecules non-covalently bound to and inactivating the dimeric, mature TGF-beta. The various suggestions that IgG bound TGF-beta complex contained LAP were based on the detection of LAP and inactive properties of the complexes. One study reported that TGF-beta bound IgG, isolated from mouse plasma, remained inactive unless incubated at acidic pH (Stach and Rowley, ibid). Other studies, however, have reported TGF-beta-LAP-IgG complexes with TGF-beta in an active conformation. Another study detected LAP produced by the same B-cells that actively produced TGF-beta-bound IgG (Rowley, D A and Stach, R M, Int Immunol, 10(3):355-363, 1998). Another report (Caver et al., ibid) concluded that naturally occurring TGF-beta IgG complexes must contain LAP, based on unsuccessful attempts at binding recombinant or plasma derived TGF-beta (both devoid of LAP) to purified mouse IgG.

Dimeric TGF-beta bound to soluble IgG without an intermediary binding protein (e.g., TGF-beta latency associated protein (LAP)), has not been reported. Bouchard and colleagues did report binding of free TGF-beta dimer to the non-CDR portion of an IgG molecule immobilized on a column (Bouchard et al., *J Exp Med*, 182:1717-1726, 1995). In this report, TGF-beta purified from porcine platelets was incubated at 4° C. for 18 hours with insoluble rabbit IgG immobilized on a Sepharose column. Based on elution of TGF-beta from the sepharose column after washing, it was determined that the free TGF-beta had associated with the IgG. Others, however, were unable to extend this study to bind TGF-beta to IgG in a soluble format (Caver et al. (ibid)).

Purified, naturally occurring IgG-bound TGF-beta had suppressive activity in vitro on cytolytic T lymphocyte function (Stach, R M and Rowley, D A, *J Exp Med*, 178:841-852, 1993), B lymphocyte function (Bouchard et al., *J Exp Med*, 182:1717-1726, 1995), polymorphonuclear leukocytes (PMN) function (Caver, T E, et al., *J Clin Invest*, 98(11):2496-2506, 1996), and antigen presenting cell (APC) function (Harada et al., *Clin Exp Immunol*, 128:204-212, 2002). The inhibition of cytolytic T lymphocyte responses by IgG-bound TGF-beta was dependent on the presence of macrophages with functional Fc receptors (Stach, R M and Rowley, D A, *J Exp Med*, 178:841-852, 1993). IgG-bound TGF-beta was approximately 500 times more potent in suppression of PMN function than recombinant TGF-beta (Caver, T E, et al., *J Clin Invest*, 98(11):2496-2506, 1996).

The provided protein complexes include TGF-beta proteins associated with IgG molecules or portions thereof (e.g., portions containing the Fc region of an IgG molecule), for example, via non-covalent bond. Because different Ig molecules and Fc regions thereof have varying affinities for activating and inhibitory Fc receptors, the complexes are useful, for example, for targeting the TGF-beta proteins to particular cells and tissues.

b. TGF-Beta Portions of the Provided Complexes

The provided TIGG complexes contain TGF-beta portions, which contain one or more TGF-beta protein, such as one or two or more TGF-beta proteins, for example, a dimer. The TGF-beta proteins include naturally occurring TGF-beta, and synthetic TGF-beta proteins, including variants, fragments, and mimetics retaining TGF-beta activity. The TGF-beta portion contains one or more TGF-beta protein or TGF-related protein, such as TGF-beta variants, including variants retaining at least at or about or at or about 50%, 60%, 70%, 80%, 90%, 95%, 96%, 97%, 98%, 99%, 100% or greater than at or about 100% of the level of activation of the TGF-beta cascade compared to a wild-type TGF-beta homodimer, such as the TGF-beta homodimer containing monomers encoded by the polynucleotide of SEQ ID NO:1. Methods for measuring activation of the TGF-beta cascade are well known.

Methods for assaying the activity of TGF-beta in a sample are well known. Exemplary methods include assays for cell growth and/or viability (e.g., apoptosis assays) of cells sensitive to TGF-beta treatment. For example, growth of the mink lung epithelial cell line (ATCC® Number CCL-64), which is generally accepted for use in such assays, is inhibited by TGF-beta concentrations down to the picogram (pg)/ml range (see Meager, A., *J. Immunol. Methods*, 141:1-14 (1991)).

Methods to assay cell growth and viability are well know. Assays for TGF-beta activity can be used, for example, to measure activity of TGF-beta protein samples for preparation of the provided complexes.

In some examples, a TGF-beta activity assay is used to assess the integrity and/or purity of the TIGG complexes, for example, by measuring the presence and/or relative amount of free TGF-beta (which binds to TGF-beta receptors to inhibit growth or viability) compared to the presence or amount of intact TIGG complexes (not binding to TGF-beta receptors), and by assessing the ability of such complexes to dissociate into free TGF-beta and immunoglobulin, e.g., upon treatment with acid.

The TGF-beta proteins of the provided TIGGs include, but are not limited to, the three known TGF-beta isoforms produced in mammals, TGF-beta 1, TGF-beta 2, TGF-beta 3. The TGF-beta proteins include monomers, and typically are dimers. For example, the TGF-beta portion of the TIGGs include, but are not limited to, TGF-beta homodimers, such as the dimeric mature TGF-beta molecule, containing two covalently associated TGF-beta molecules.

In one embodiment, the TGF-beta protein is a TGF-beta 1, which is a polypeptide growth factor, including, but not limited to, human TGF-beta 1. For example, in one aspect, the TGF-beta is the human TGF-beta 1 protein having the sequence of amino acids set forth in SEQ ID NO:6, or a TGF-beta 1 dimer, where each monomer of the dimer contains the sequence of amino acids set forth in SEQ ID NO:6. In another aspect, the TGF-beta is a TGF-beta protein having at least at or about 70%, 75%, 80%, 85%, 90%, 95%, 96%, 97%, 98%, 99%, or 100% sequence identity with SEQ ID NO:6, or having at or about 70%, 75%, 80%, 85%, 90%, 95%, 96%, 97%, 98%, 99%, or 100% sequence identity with SEQ ID NO:6. In another aspect, the TGF-beta is a TGF-beta dimer, where each monomer of the dimer is a protein having at least at or about 70%, 75%, 80%, 85%, 90%, 95%, 96%, 97%, 98%, 99%, or 100% sequence identity with SEQ ID NO:6, or having at or about 70%, 75%, 80%, 85%, 90%, 95%, 96%, 97%, 98%, 99%, or 100% sequence identity with SEQ ID NO:6.

In another aspect, the TGF-beta is a TGF-beta 1 encoded by the sequence of nucleic acids set forth in SEQ ID NO:1. In another aspect, the TGF-beta is a TGF-beta 1 dimer, where each monomer is encoded by the sequence of nucleic acids set forth in SEQ ID NO:1. In another aspect, the TGF-beta is a protein encoded by a sequence of nucleic acids having at least at or about 70%, 75%, 80%, 85%, 90%, 95%, 96%, 97%, 98%, 99%, or 100% sequence identity, or at or about 70%, 75%, 80%, 85%, 90%, 95%, 96%, 97%, 98%, 99%, or 100% sequence identity, with SEQ ID NO:1. In another aspect, the TGF-beta is a dimer, where each monomer of the dimer is a protein encoded by a sequence of nucleic acids having at least at or about 70%, 75%, 80%, 85%, 90%, 95%, 96%, 97%, 98%, 99%, or 100% sequence identity, or at or about 70%, 75%, 80%, 85%, 90%, 95%, 96%, 97%, 98%, 99%, or 100% sequence identity, with SEQ ID NO:1. In one example, the two monomers of the TGF-beta dimer are associated via a covalent bond, e.g., a disulfide bond. For example, exemplary of the TGF-beta proteins are TGF-beta dimers comprising two monomers bound by a covalent disulfide bond, each monomer of the dimer having at or about 80% or higher sequence identity to the amino acid sequence of SEQ ID NO:6.

In one aspect, the TGF-beta protein (e.g., each monomer of the TGF-beta dimer), is encoded by a polynucleotide comprising a sequence having at least at or about, or at or about, 70%, 75%, 80%, 85%, 90%, 95%, 96%, 97%, 98%, 99%, or 100% sequence identity to SEQ ID NO:1, such as polynucleotide sequences containing one or more amino acid substitutions, deletions, insertions or additions, compared to SEQ ID NO:1, where the TGF-beta portion of the TIGG retains essentially the same binding and activation profile as a wild-type TGF-beta monomer, such as essentially the same binding and activation profile as the polypeptide of SEQ ID NO:6. In a further aspect, the TGF-beta portion of AcTIGG and InTIGG contains an amino acid sequence having 70%, 75%, 80%, 85%, 90%, 95%, 96%, 97%, 98%, 99%, or 100% sequence identity to SEQ ID NO:6, wherein the amino acid sequence comprises one or more amino acid substitutions, deletions, or additions relative to SEQ ID NO:6.

In another aspect, the TGF-beta protein (e.g., each monomer of a TGF-beta dimer in the TGF-beta portion), contains one or more amino acid substitutions, deletions, insertions or additions relative to SEQ ID NO:6, where the TGF-beta portion of the TIGG retains essentially the same binding and activation profile as a wild-type TGF-beta monomer, such as the TGF-beta monomer of SEQ ID NO:6.

For example, in one aspect, the TGF-beta portion of the TIGG (e.g., the AcTIGG or InTIGG) retains at least 50%, 60%, 70%, 80%, 90%, 95%, 96%, 97%, 98%, 99% or 100% of the binding affinity to a mammalian TGF-beta type II Receptor in comparison to a wild-type TGF-beta monomer.

In another aspect, the TGF-beta portion of AcTIGG and InTIGG retains at least 50%, 60%, 70%, 80%, 90%, 95%, 96%, 97%, 98%, 99%, or 100% of the activation of the TGF-beta cascade in comparison to a recombinant TGF-beta homodimer.

In another aspect, the TIGG (e.g., AcTIGG or InTIGG) has a similar activation of the TGF-beta cascade in comparison to wild-type TGF-beta. In one example, the activation retains at least at or about or at or about 50%, 60%, 70%, 80%, 90%, 95%, 96%, 97%, 98%, 99%, 100% or greater than at or about 100% of the level of activation shown by a wild-type TGF-beta homodimer, such as the TGF-beta homodimer containing monomers encoded by the polynucleotide of SEQ ID NO:1.

c. Immunoglobulin Portions of the Complexes

The TGF-beta protein(s) in the TGF-beta portions of the TIGGs are associated with protein(s) of Immunoglobulin (Ig) portions. The Ig portions contain one or more Ig protein, such as one or two or more Ig molecule, chain or fragment thereof. The Ig proteins include Ig molecules, and chains and functional portions (e.g., fragments) thereof. For example, in one aspect, the Ig portion contains a full-length immunoglobulin. In another aspect, the Ig portion contains one or more chains of the full-length immunoglobulin (typically an IgG molecule), such as heavy chains. In another aspect, the Ig portion contains a functional portion of a full-length immunoglobulin or chain, such as a constant region or Fc region thereof (typically an Fc-gamma region). The constant region or Fc region thereof contains all or part of the binding affinity to one or more Fc receptors, compared to the corresponding full-length Ig molecule. In one embodiment, the Ig portion contains one Ig protein, which can be a full-length Ig molecule or a region thereof. In another embodiment, the Ig portion contains more than one, e.g., 2 or more, Ig proteins, each of which is a full-length Ig molecule or region thereof. In one example, the Ig portion contains two Ig proteins, each of which is associated with one monomer of the TGF-beta dimer in the TIGG complex. The Ig proteins can be human Ig proteins, or any mammalian Ig proteins, such as mouse or rat Ig proteins. For use in human subjects, it typically is desired that the Ig proteins are human Ig proteins.

In one aspect, the Ig portion of the TIGG is or contains a full-length immunoglobulin G molecule, containing two heavy chains and two light chains, the two heavy chains being covalently bound to one another via disulfide bonds, and each of the two light chains covalently attached to one of the heavy chains. In another aspect, the Ig portion of the TIGG is less than the full length IgG molecule, such as a portion of the IgG molecule that retains all or part of the binding specificity for one or more of the Fc receptors bound by the constant region of the IgG molecule. The Ig proteins of the Ig portions include natural Ig molecules (and regions thereof) and synthetically produced, e.g., artificial, Ig molecules and portions, such as variant Ig proteins that vary in amino acid sequence compared to a wild-type Ig protein or any of the Ig proteins disclosed herein, and have particular desired functional characteristics, such as binding affinities for particular Fc receptors.

The Ig proteins of the Ig portions can be of any isotype and/or sub-class, and typically is of the IgG isotype. The Ig portion of a single complex, e.g., a single TIGG, can contain more than one distinct isotype/sub-type. Also provided are mixtures of TIGGs, which can contain multiple different Ig isotypes and sub-types. The IgG proteins thereof include, but are not limited to, human IgG1, human IgG2, human IgG3, human IgG4, mouse IgG1, and mouse IgG2a, and functional portions of such IgG molecules, including Fc portions, and variants thereof, such as those having substantially the same, or improved binding affinities/specificities as described herein.

For example, the Ig proteins include, but are not limited to, proteins containing the sequence of amino acids (e.g., proteins having an Fc region containing the sequence of amino acids) set forth in any of: SEQ ID NO:7, SEQ ID NO:8, SEQ ID NO:9, and SEQ ID NO:10, and Ig proteins containing Fc regions encoded by the nucleotide sequence set forth in any of: SEQ ID NO:2, SEQ ID NO:3, SEQ ID NO:4, and SEQ ID NO:5, and the Ig proteins having the amino acid sequences set forth in Table 1 and Table 2, and variants thereof, such as those having one or more addition, deletion, substitution or insertion, and having have desired functional characteristics as described herein. For example, the Ig proteins include proteins with amino acid sequences (and those with Fc regions having amino acid sequences) containing at least at or about, or at or about, 70%, 75%, 80%, 85%, 90%, 95%, 96%, 97%, 98%, 99%, or 100% sequence identity to any of SEQ ID NO:7, SEQ ID NO:8, SEQ ID NO:9, and SEQ ID NO:10, and variants encoded by nucleotide sequences containing at least at or about, or at or about, 70%, 75%, 80%, 85%, 90%, 95%, 96%, 97%, 98%, 99%, or 100% sequence identity to any of SEQ ID NO:2, SEQ ID NO:3, SEQ ID NO:4 and SEQ ID NO:5, such as those having one or more nucleic acid insertion, deletion, addition or substitution, and Ig proteins with amino acid sequences containing at least at or about, or at or about, 70%, 75%, 80%, 85%, 90%, 95%, 96%, 97%, 98%, 99%, or 100% sequence identity to any of the Ig proteins set forth in Tables 1 and 2.

The Ig portions, including the Ig portions containing variant Ig proteins, have a desired functional property, typically at or about specified binding affinity or ratio of binding affinities, or at least at or about a specified binding affinity or ratio of binding affinities, to one or more Fc receptors or Fc receptor classes. The binding affinity can be specified as a percentage of the binding affinity of a known (e.g., wild-type) Ig molecule or region thereof, or can be specified as a ratio of the binding affinity for a particular type of Fc receptor compared to another type, such as with an A/I ratio.

For example, in one aspect, the Ig portion of the TIGG contains an Ig protein that is a variant of a known Ig molecule, such as those having any of the amino acid sequences described herein, that retains all or part of the binding specificity of the parent Ig protein for one or more of the Fc receptors bound by the constant region of the IgG molecule, such as at least at or about 50%, 60%, 70%, 80%, 90%, 95%, 96%, 97%, 98%, 99% or 100% of the binding affinity of the parent Ig protein, constant region, or Fc region, for example, to a mammalian FcγR. For example, the Ig portions include those having a particular sequence identity to any of SEQ ID NOs: 7-10, and having at least at or about 50%, 60%, 70%, 80%, 90%, 95%, 96%, 97%, 98%, 99% or 100% of the binding affinity of those Ig proteins for a specified FcγR.

In another aspect, the Ig portion of the TIGG contains an Ig portion that has at least at or about, or less than at or about, a specified A/I ratio. For example, the TIGGs include AcTIGGs, having A/I ratios less than 1, such as less than at or about 0.9, 0.8, 0.7, 0.6, and typically less than at or about 0.5, such as 0.4, 0.3, 0.2, 0.1, 0.09, 0.08, 0.07, 0.06, 0.05, 0.04, 0.03, 0.02, 0.01, 0.009, 0.005, or 0.001, or less. The TIGGs further include InTIGGs, having A/I ratios at least at or about 2, such as at or about 2, 3, 4, 5, 6, 7, 8, 9, 10, 11, 12, 13, 14, 15, 16, 17, 18, 19, 20, 25, 30, 35, 40, 45, 50, 55, 60, 65, 70, 80 or 90 or greater.

In certain aspects, the derivative, variant or fragment thereof retains at least 50%, 60%, 70%, 80%, 90%, 95%, 96%, 97%, 98%, 99% or 100% of the binding affinity of the full-length Ig, constant region, or Fc region to a mammalian FcγR.

The particular isotype(s) and sub-type(s) in the TGF-beta containing complexes can be chosen based on a number of factors, for example, the type of cell or tissue to which targeting of the TIGG is desired. Typically, the targeting of the TIGG complex depends on the isotype of the Ig portion, such as the sub-class of IgG or portion thereof in the complex. For example, in one aspect, the TGF-beta complex contains an IgG or portion thereof having a greater binding affinity for activating Fc receptors. In this aspect, the complex typically is targeted to cells that express activating FcγRs, such as cells expressing predominantly activating FcγRs, cells expressing a greater amount of activating versus inhibitory FcγRs, or cells expressing only activating FcγRs. In another aspect, the TGF-beta complex contains an IgG or portion thereof with a greater binding affinity for inhibitory Fc receptors. In this aspect, the TGF-beta complex is targeted to cells expressing inhibitory FcγRs, such as cells expressing predominantly inhibitory FcγRs, cells expressing more inhibitory than activating FcγRs, or cells expressing only inhibitory FcγRs.

Variants

The Ig portions of the provided TIGGs further include Ig proteins that are variants of known proteins (e.g., wild-type Ig molecules and any of the proteins described herein) that retain all or part of the function of the parent proteins, and/or contain improved function compared to the parent. For example, the Ig proteins include site directed mutants of IgG molecules and portions (e.g., Fc portions) thereof, that are designed to more specifically interact with either activating FcγRs or inhibitory FcγRs, compared to conventional Ig molecules.

The variants can be made by mutating residues in Ig molecules using known techniques, and include, for example, any of the mutants described by Armour, K L et al., (*Mol Immunol*, 40:585-593, 2003). In one example, a known IgG protein or Fc region thereof is mutated in order to decrease or increase the A/I ratio of the protein, for example, to generate an AcTIGG or InTIGG respectively. In one embodiment, an AcTIGG is produced by mutating residues in a human IgG4 or Fc portion thereof (such as proteins containing an amino acid sequence set forth in SEQ ID NO:10), for example, to generate Ig proteins containing decreased A/I ratios compared to the parent molecule. In another embodiment, an InTIGG is produced by mutating residues in a human IgG1, IgG2 or IgG3 or Fc portion thereof (such as the proteins containing an amino acid sequence set forth in SEQ ID NOs: 7-9, respectively), for example, to generate Ig proteins containing decreased A/I ratios compared to the parent molecule. It typically is desired that the variant contains at least at or about 70%, 80%, 90%, 91%, 92%, 93%, 94%, 95%, 96%, 97%, 98%, 99%, or 100% sequence identity compared to the parent Ig molecule, and contains a similar or improved A/I ratio as described herein for particular uses.

Multiple Ig Sub-Types and TIGG Mixtures

In one embodiment, the Ig portion contains one Ig subtype. In another embodiment it contains multiple sub-types. In another embodiment, provided is a TIGG mixture, containing a plurality of different TIGGs, having different Ig classes and/or sub-types. In one aspect of this embodiment, the TIGG mixture includes a mixture of two, three or all four naturally occurring human immunoglobulin G subtypes in the Ig portions of the plurality of TIGGs in the mixture. Such mixtures include those made by combining the mixture of Ig molecules contained in the commercially available well-known human gamma globulin used for intravenous injection in humans or similar mixture. This composition can be used, for example, in treatment of autoimmune disease. In another aspect, the TIGG mixture composition contains, as the Ig portions of the TIGGs, any one or more of purified human IgG1, human IgG2 or IgG3. Exemplary of such a composition is an InTIGGs composition for treating autoimmune disease. In another aspect, the TIGG composition contains, as the Ig portions of the TIGGs, the Fc region (Fc fragment) or functional region thereof, of any one or more of human IgG1, IgG2, or IgG3 Exemplary of such a composition is an InTIGGs composition for treating autoimmune disease.

In another aspect, the TIGG composition contains, as the Ig portions of the TIGGs, the Ig portions of human gamma globulin (available commercially as IVIG). In another aspect, the Ig portion of the TIGG is purified human IgG4, or a functional portion thereof, such as an Fc portion thereof. Exemplary of such TIGGs are AcTIGGs, which can be used for example, to treat cancer.

d. Association of the TGF-Beta and Ig Portions of the Complex

The TGF-beta portion (for example, the 25 kDa TGF-beta dimer), associates with the Ig portion (e.g., the IgG molecule or Fc portion thereof) in the provided complexes.

Typically, the association is via an interaction (typically a direct interaction) of the TGF portion with the constant region of the Ig molecule(s) in the Ig portion, such as via interaction with the Fc portion. In another aspect, the TGF-beta portion can associate with the Ig portion through the variable region of the Ig, such as by interacting with one or more CDR of the variable region. Various methods for association of proteins in complexes are well known and can be used to associate the TGF-beta portion with the Ig portion in the provided complexes. Typically, however, the TGF-beta portion of the provided complexes, for example, the TIGG (e.g., AcTIGG or InTIGG) is associated with the Ig portion via a bond, and typically via a non-covalent bond.

Methods for forming the complexes are described herein. Alternatively, the two molecules can be associated via another well-known method or interaction, such as via a linker, such as a peptide linker.

e. AcTIGGs

The provided TIGGs and TIGG-containing compositions include AcTIGGs (Activating TGF-beta IgGs), which have a higher binding affinity and/or specificity for inhibitory FcγRs compared to activating FcγRs. In other words, the AcTIGGs have relatively low A/I ratios. For example, the AcTIGGs have A/I ratios of less than 1, such as less than at or about 0.9, 0.8, 0.7, 0.6, and typically less than at or about 0.5, such as 0.4, 0.3, 0.2, 0.1, 0.09, 0.08, 0.07, 0.06, 0.05, 0.04, 0.03, 0.02, 0.01, 0.009, 0.005, or 0.001, or less. In one example, the AcTIGG has a substantially higher affinity for a mammalian inhibitory Fcγ receptor than the mammalian activating Fcγ receptors.

Thus, the AcTIGGs can be used to target and suppress immune cells having higher expression levels of inhibitory FcγRs than activating FcγRs, such as cells expressing only inhibitory FcγRs, cells expressing predominantly inhibitory FcγRs, and cells expressing more inhibitory FcγRs than activating FcγRs. The AcTIGGs can be used in both in vivo and in vitro methods, such as methods for treating diseases as provided herein. For example, the in vivo activities of the AcTIGG include, but are not limited to, ameliorating cancer formation, growth, and metastases.

The AcTIGGs include, but are not limited to, complexes containing TGF-beta (e.g., TGF-beta dimers) associated (e.g., non-covalently bound) to one or more IgG4 (e.g., human IgG4) or functional fragments thereof, such as Fc portions and constant region portions, or variant thereof.

In one embodiment, the AcTIGG contains an Ig portion having Ig protein(s) containing the sequence of amino acids set forth in SEQ ID NO:10, and/or Ig protein(s) encoded by a nucleic acid having the nucleotide sequence set forth in SEQ ID NO:5.

In other embodiments, the Ig portion of the AcTIGG contains an Ig protein having one or more amino acid additions, deletions, insertions or substitutions compared to SEQ ID NO:10, or compared to a wild-type human IgG4 or Fc region thereof, but retaining all or part of the functional characteristics of such a protein, typically the binding affinity for Fc receptors.

In one aspect, the immunoglobulin protein of the AcTIGG Ig portion is encoded by a polynucleotide having the sequence of nucleic acids set forth in SEQ ID NO:5. In another aspect, the Ig protein of the AcTIGG Ig portion is encoded by a polynucleotide containing a sequence of nucleic acids having at least at or about, or at or about, 70%, 75%, 80%, 85%, 90%, 95%, 96%, 97%, 98%, 99%, or 100% sequence identity to SEQ ID NO:5. In one example, the Ig protein is encoded by a polynucleotide sequence containing one or more nucleic acid substitutions, additions, deletions or insertions compared to SEQ ID NO:5, where the Ig portion of the TIGG retains essentially the same binding and functional profile as a wild-type human IgG4 or Fc portion thereof or essentially the same binding and functional profile as a protein having the amino acid sequence set forth in SEQ ID NO:10.

In another aspect, the Ig portion of the TIGG (e.g., AcTIGG) has a sequence of amino acids set forth in SEQ ID NO:10, or a sequence of amino acids having at least at or about, or at or about, 70%, 75%, 80%, 85%, 90%, 95%, 96%, 97%, 98%, 99%, or 100% sequence identity to SEQ ID NO:10, such as a protein containing one or more amino acid deletions, insertions, additions or substitutions compared to SEQ ID NO:10 that retains essentially the same binding and functional profile as a wild-type human IgG4 or Fc portion thereof.

In one embodiment, the Ig protein of the AcTIGG, including any of the variants described above, has at least at or about 50%, 60%, 70%, 80%, 90%, 95%, 96%, 97%, 98%, 99% or 100% of the binding affinity for a mammalian FcγRIIb compared to a wild-type IgG4 (e.g., human IgG4) or Fc portion thereof (e.g., SEQ ID NO:10), and/or has (e.g., while displaying) less than at or about 50%, 60%, 70%, 80%, 90%, 95%, 96%, 97%, 98%, 99% or 100% of the binding affinity for the mammalian FcγRIIa, FcγRIII, and/or FcγRIV compared to a wild-type IgG4 (e.g., human IgG4) or Fc portion thereof (e.g., SEQ ID NO:10).

In one embodiment, the AcTIGG complexes contain Ig portions made by mutagenesis of nucleic acids encoding immunoglobulin proteins (e.g., naturally occurring Ig molecules and fragments thereof, such as those having amino acid sequences as set forth in Table 1). For example, AcTIGG variants having the desired specificity can be prepared using routine mutagenesis methods for mutating Ig portions. Residues to mutate can be identified by systematically mutating residues to different residues, and identifying those that have the desired reduction in activating Fcγ receptor binding and increased suppressive Fcγ receptor binding. Alternatively or additionally, mutations may be based upon predicted or known 3-D structures of one or more IgG proteins, including predicted effects of various mutations (see, e.g., Mittl, P. R., et al., *Protein Sci* (1996) 5:1261-1271 and Hinck, A. P., et al., *Biochemistry* (1996) 35(26):8517-8534).

Such predictions can be made by those of skill in the art of computational chemistry. Hence, for any selected protein, the mutations need to reduce or eliminate activating Fcγ receptor binding affinity of AcTIGG but retain or augment inhibitory Fcγ binding affinity can be determined empirically.

Exemplary immunoglobulin proteins and nucleic acid sequences that can be mutated for use in the compositions and methods described herein, include, but are not limited to, the sequences described in Table 1.

In this embodiment, after generating TIGGs containing mutagenized Ig portions, AcTIGGs are selected from the mutants based on desired binding properties or functional activities. For example, an AcTIGG generated from mutagenesis of an IgG4, fragment or variant thereof, typically has at least at or about 50%, 60%, 70%, 80%, 90%, 95%, 96%, 97%, 98%, 99% or 100% of the binding affinity for a mammalian FcγRIIb compared to a wild-type IgG4 (e.g., human IgG4) or Fc portion thereof (e.g., SEQ ID NO:10), and/or has (e.g., while displaying) less than at or about 50%, 60%, 70%, 80%, 90%, 95%, 96%, 97%, 98%, 99% or 100% of the binding affinity for the mammalian FcγRIIa, FcγRIII, and/or FcγRIV compared to a wild-type IgG4 (e.g., human IgG4) or Fc portion thereof (e.g., SEQ ID NO:10).

Evaluating the binding affinity of an AcTIGG to a mammalian activating and inhibitory Fcγ receptor is readily performed by one of ordinary skill in the art.

Typical methods include a variety of kinetic and thermodynamic assays, including optical detection as BIAcore and RIfS, equilibrium titration and stopped-flow fluorescence. In one aspect, binding affinities are determined using the assays set out in the examples.

Evaluating the activity of AcTIGGs also may be carried out by well-known methods. For example, suppression of particular immune cells by AcTIGG complexes can be ascertained by determining, for example, the types and amounts of cytokines macrophages produce after treatment with AcTIGG and then activation by LPS as described herein. Other assays for measuring immune cell suppression are well-known to those of skill in the art, and may be employed.

TABLE 1

Ig Proteins for use in TIGGs

| GenBank gi No. | Accession No. | DESCRIPTION | SPECIES |
|---|---|---|---|
| 184747 | AAC82527 | immunoglobulin G1, Fc region | Homo sapiens |
| 184758 | AAB59393 | immunoglobulin G2, Fc region | Homo sapiens |
| 577056 | CAA27268 | immunoglobulin G3, Fc region | Homo sapiens |
| 184759 | AAB59394 | immunoglobulin G4, Fc region | Homo sapiens |
| 109133449 | XP_001097387 | immunoglobulin G4, Fc region | Macaca mulatta |
| 109085083 | XP_001100439 | immunoglobulin G1, constant region heavy chain | Macaca mulatta |
| 109133460 | XP_001099592 | immunoglobulin G2, constant region, heavy chain | Macaca mulatta |
| 114655149 | XP_522970 | immunoglobulin G1, Fc region | Pan troglodytes | f. InTIGGs

The provided TIGGs and TIGG-containing compositions further include InTIGGs (Inhibiting TGF-beta IgG), which have a higher binding affinity and/or specificity for activating FcγRs compared to inhibitory FcγRs. In other words, the InTIGGs have relatively high A/I ratios. For example, the InTIGGs have A/I ratios at least at or about 2, such as at or about 2, 3, 4, 5, 6, 7, 8, 9, 10, 11, 12, 13, 14, 15, 16, 17, 18, 19, 20, 25, 30, 35, 40, 45, 50, 55, 60, 65, 70, 80 or 90 or greater. In one example, the InTIGG has a substantially higher affinity for mammalian activating FcγRs compared to mammalian inhibitory FcγR.

Thus, the InTIGGs can be used to target and suppress immune cells having higher expression levels of activating FcγRs than inhibitory FcγRs, such as cells expressing only activating FcγRs, cells expressing predominantly activating FcγRs, and cells expressing more activating FcγRs than inhibitory FcγRs. The InTIGGs include, but are not limited to, complexes containing TGF-beta (e.g., TGF-beta dimers) associated (e.g., non-covalently bound) to one or more human IgG1, human IgG2, human IgG3, or functional fragments, such as Fc portions and constant region portions and variants thereof. The InTIGGs can be used in both in vivo and in vitro methods, such as methods for treating diseases as provided herein, and for inhibiting inflammation in a subject. For example, the in vivo activities of the AcTIGG include, but are not limited to, ameliorating autoimmune disease and autoimmune symptoms, and preventing recurrence of autoimmunity.

The InTIGGs include, but are not limited to, complexes containing TGF-beta (e.g., TGF-beta dimers) associated (e.g., non-covalently bound) to one or more IgG1, IgG2, IgG3 (e.g., human IgG1, 2, or 3) or functional fragments thereof, such as Fc portions and constant region portions, or variant thereof. In one embodiment, the AcTIGG contains an Ig portion having Ig protein(s) containing the sequence of amino acids set forth in any of SEQ ID NO:7, 8 and 9, and/or Ig protein(s) encoded by a nucleic acid having the nucleotide sequence set forth in any of SEQ ID NOs: 2, 3 and 4.

In other embodiments, the Ig portion of the InTIGG contains an Ig protein having one or more amino acid additions, deletions, insertions or substitutions compared to any of SEQ ID NOs: 7, 8 and 9, or compared to a wild-type human IgG1, IgG2 or IgG3, or Fc region thereof, but retaining all or part of the functional characteristics of such a protein, typically the binding affinity for Fc receptors.

In one aspect, the immunoglobulin protein of the InTIGG Ig portion is encoded by a polynucleotide having the sequence of nucleic acids set forth in any of SEQ ID NOs: 2-4. In another aspect, the Ig protein of the InTIGG Ig portion is encoded by a polynucleotide containing a sequence of nucleic acids having at least at or about, or at or about, 70%, 75%, 80%, 85%, 90%, 95%, 96%, 97%, 98%, 99%, or 100% sequence identity to any of SEQ ID NOs: 2, 3 or 4. In one example, the Ig protein is encoded by a polynucleotide sequence containing one or more nucleic acid substitutions, additions, deletions or insertions compared to SEQ ID NO:2, SEQ ID NO:3 or SEQ ID NO:4, where the Ig portion of the TIGG retains essentially the same binding and functional profile as a wild-type human IgG1, IgG2, or IgG3, or Fc portion thereof or a protein encoded by SEQ ID NO:2, 3, or 4.

In another aspect, the Ig portion of the InTIGG has a sequence of amino acids set forth in SEQ ID NO:7, 8 or 9, or a sequence of amino acids having at least at or about, or at or about, 70%, 75%, 80%, 85%, 90%, 95%, 96%, 97%, 98%, 99%, or 100% sequence identity to SEQ ID NO:7, 8, or 9, such as a protein containing one or more amino acid deletions, insertions, additions or substitutions compared to SEQ ID NO:7, 8 or 9 that retains essentially the same binding and functional profile as a wild-type human IgG1, IgG2 or IgG3 or Fc portion thereof, or binding and functional property of the protein having the amino acid sequence of SEQ ID NO:7, 8, or 9.

In one embodiment, the Ig protein of the AcTIGG, including any of the variants described above, has at least at or about 50%, 60%, 70%, 80%, 90%, 95%, 96%, 97%, 98%, 99% or 100% of the binding affinity for a mammalian FcγRIIb compared to a wild-type IgG4 (e.g., human IgG4) or Fc portion thereof (e.g., SEQ ID NO:10), and/or has (e.g., while displaying) less than at or about 50%, 60%, 70%, 80%, 90%, 95%, 96%, 97%, 98%, 99% or 100% of the binding affinity for the mammalian FcγRIIa, FcγRIII, and/or FcγRIV compared to a wild-type IgG4 (e.g., human IgG4) or Fc portion thereof (e.g., SEQ ID NO:10).

In one embodiment, the InTIGG contains Ig portions having Ig proteins produced by mutagenesis of nucleic acids encoding Ig proteins (e.g., naturally occurring Ig proteins and fragments thereof, such as those having the amino acid sequences set forth in Table 2). For example, InTIGG variants having the desired specificity can be prepared using routine mutagenesis methods, e.g., for mutating Ig portions of the TIGGS. Residues in the Ig molecules to mutate can be identified by systematically mutating residues to different residues, and identifying those that have the desired reduction in inhibitory Fcγ receptor binding and increased activating Fcγ receptor binding. Alternatively or additionally, mutations may be based upon predicted or known 3-D structures of one or more IgG proteins, including predicted effects of various mutations (see, e.g., Mittl, P. R., et al., *Protein Sci* (1996) 5:1261-1271 and Hinck, A. P., et al., *Biochemistry* (1996) 35(26):8517-8534).

Such predictions can be made by those of skill in the art of computational chemistry. Hence, for any selected protein, the mutations need to reduce or eliminate inhibitory Fcγ receptor binding affinity of InTIGG but retain or augment activating Fcγ binding affinity can be determined empirically.

Exemplary immunoglobulin proteins and nucleic acid sequences that can be mutated for use in the compositions and methods described herein, include, but are not limited to, the sequences described in Table 2.

In this embodiment, after generating TIGGs containing the mutagenized Ig molecules or portions thereof, InTIGGs are selected from among the mutants based on desired binding properties or functional activities. For example, an InTIGG generated by mutagenesis of a human IgG1, IgG2 or IgG3 or fragment or variant thereof typically retains at least 50%, 60%, 70%, 80%, 90%, 95%, 96%, 97%, 98%, 99% or 100% of the binding affinity of the IgG1, IgG2 or IgG3 or fragment or variant for the mammalian FcγRIIa, FcγRIII, and/or FcγRIV.

The InTIGG typically further displays less than 50%, 60%, 70%, 80%, 90%, 95%, 96%, 97%, 98%, 99% or 100% binding affinity to the mammalian FcγRIIb in comparison to a wild-type IgG4 IgG1, IgG2 or IgG3.

Binding affinities can be evaluated by methods well known in the art. For example, ascertaining the binding affinity of an InTIGG to a mammalian activating and suppressive Fcγ receptor is readily performed by one of ordinary skill in the art. Typical methods include a variety of kinetic and thermodynamic assays, including optical detection as BIAcore and RIfS, equilibrium titration and stopped-flow fluorescence. In one aspect, binding affinities are determined using the assays set out in the examples.

The InTIGG further typically has higher, typically substantially higher, affinity for mammalian activating Fcγ receptors than mammalian inhibitory Fcγ receptors. Evaluating the activity of InTIGGs can also be carried out by well-known methods. Suppression of certain immune cells by InTIGG may be ascertained by determining by, for example, the types and amounts of cytokines macrophages produce after treatment with AcTIGG and then activation by LPS. Other assays are well-known to those of skill in the art, and may be employed.

TABLE 2

Ig Proteins for use in TIGGs

| GenBank gi No. | Accession No. | DESCRIPTION | SPECIES |
| --- | --- | --- | --- |
| 184747 | AAC82527 | immunoglobulin G1, Fc region | Homo sapiens |
| 184758 | AAB59393 | immunoglobulin G2, Fc region | Homo sapiens |
| 577056 | CAA27268 | immunoglobulin G3, Fc region | Homo sapiens |
| 184759 | AAB59394 | immunoglobulin G4, Fc region | Homo sapiens |
| 109133449 | XP_001097387 | immunoglobulin G4, Fc region | Macaca mulatta |
| 109085083 | XP_001100439 | immunoglobulin G1, constant region heavy chain | Macaca mulatta |
| 109133460 | XP_001099592 | immunoglobulin G2, constant region heavy chain | Macaca mulatta |
| 114655149 | XP_522970 | immunoglobulin G1, Fc region | Pan troglodytes | g. Polynucleotides

Also provided are nucleic acids, e.g., polynucleotides, encoding the TIGGs and proteins and portions thereof. The polynucleotides include any polynucleotide encoding a TGF-beta protein described herein, such as polynucleotides encoding a TGF-beta protein having the sequence of amino acids set forth in SEQ ID NO:6, e.g., polynucleotides having the nucleotide sequence set forth in SEQ ID NO:1, and polynucleotides containing one or more nucleotide addition, deletion, insertion or substitution compared to such a polynucleotide, but still encoding a polypeptide having one or more functional properties of such a protein, for example, retaining all or a substantial portion of the TGF-beta activity compared to the protein or compared to wild-type TGF-beta. For example, the polynucleotides include those having at least at or about 70, 75, 80, 85, 90, 91, 92, 93, 94, 95, 96, 97, 98, 99 or 100% sequence identity to SEQ ID NO:1, and polynucleotides encoding a polypeptide having an amino acid sequence with at least at or about 70, 75, 80, 85, 90, 91, 92, 93, 94, 95, 96, 97, 98, 99 or 100% sequence identity with the amino acid sequence set forth in SEQ ID NO:6.

The provided polynucleotides further include polynucleotides encoding any of the Ig proteins and variants described herein, such as polynucleotides encoding an Ig protein having the sequence of amino acids set forth in any of: SEQ ID NO:7, SEQ ID NO:8, SEQ ID NO:9, and SEQ ID NO:10, and polynucleotides having the nucleotide sequence set forth in any of: SEQ ID NO:2 (coding sequence of Fc region of human IgG1), SEQ ID NO:3 (coding region of Fc region of human IgG2), SEQ ID NO:4 (coding region of Fc region of human IgG3), polynucleotides of Tables 1, and 2.

The Ig polynucleotides further include variants of these polynucleotides, such as those having one or more addition, deletion, substitution or insertion, and having have desired functional characteristics as described herein. For example, the Ig polynucleotides include those encoding proteins with amino acid sequences containing at least at or about, or at or about, 70%, 75%, 80%, 85%, 90%, 95%, 96%, 97%, 98%, 99%, or 100% sequence identity to any of SEQ ID NO:7 (encoded by SEQ ID NO:2), SEQ ID NO:8 (encoded by SEQ ID NO:3), SEQ ID NO:9 (encoded by SEQ ID NO:4), and SEQ ID NO:10 (encoded by SEQ ID NO:5), and polynucleotides having sequences containing at least at or about, or at or about, 70%, 75%, 80%, 85%, 90%, 95%, 96%, 97%, 98%, 99%, or 100% sequence identity to any of SEQ ID NO:2, SEQ ID NO:3, SEQ ID NO:4 and SEQ ID NO:5 (coding region of Fc region of human IgG4), such as those having one or more nucleic acid insertion, deletion, addition or substitution As described above, the Ig proteins encoded by the polynucleotides typically have one or more desired functional properties, such as those having the specified A/I ratios and/or binding affinities specified herein. For example, in one embodiment the polynucleotides encode Ig proteins having at least at or about, or less than at or about, a specified A/I ratio. For example, the TIGGs include AcTIGGs, having A/I ratios less than 1, such as less than at or about 0.9, 0.8, 0.7, 0.6, and typically less than at or about 0.5, such as 0.4, 0.3, 0.2, 0.1, 0.09, 0.08, 0.07, 0.06, 0.05, 0.04, 0.03, 0.02, 0.01, 0.009, 0.005, or 0.001. The TIGGs further include InTIGGs, having A/I ratios at least at or about 2, such as at or about 2, 3, 4, 5, 6, 7, 8, 9, 10, 11, 12, 13, 14, 15, 16, 17, 18, 19, 20, 25, 30, 35, 40, 45, 50, 55, 60, 65, 70, 80 or 90 or greater.

In certain aspects, the polynucleotides encode Ig protein variants or fragments thereof that retain at least 50%, 60%, 70%, 80%, 90%, 95%, 96%, 97%, 98%, 99% or 100% of the binding affinity of the full-length Ig, constant region, or Fc region to a mammalian FcγR.

The nucleic acids used to practice the provided embodiments can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) *J. Am. Chem. Soc.* 105:661; Belousov (1997) *Nucleic Acids Res.* 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; U.S. Pat. No. 4,458,066. Alternatively, nucleic acids can be obtained from commercial sources.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *Molecular Cloning: A Laboratory Manual* (2nd ed.), Vols. 1-3, Cold Spring Harbor Laboratory, (1989); *Current Protocols in Molecular Biology*, Ausubel, ed. John Wiley & Sons, Inc., New York (1997); *Laboratory Techniques in Biochemistry and Molecular Biology: Hybridization with Nucleic Acid Probes, Part I. Theory and Nucleic Acid Preparation*, Tijssen, ed. Elsevier, N.Y. (1993).

Another useful means of obtaining and manipulating nucleic acids used to practice the provided methods is to clone from genomic samples, and, if desired, screen and re-clone inserts isolated or amplified from, e.g., genomic clones or cDNA clones.

Sources of nucleic acid used in the provided include genomic or cDNA libraries contained in, e.g., mammalian artificial chromosomes (MACS), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

In practicing the provided embodiments, provided nucleic acids can be reproduced by amplification. Amplification can also be used to clone or modify the provided nucleic acids. Thus, provided are amplification primer sequence pairs for amplifying the provided nucleic acids. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., *PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) *Proc. Natl. Acad. Sci. USA* 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

vi. Methods of Producing the TIGG Complexes

Typically, the TIGG complexes are made by combining and incubating TGF-beta protein(s) with Ig protein(s) under conditions whereby they associate, typically via non-covalent bonds. Methods for stable, non-covalent binding of certain types of molecules, particularly small molecules, to immunoglobulin (Ig) are well known. For example, a systematic study was undertaken to determine the optimized parameters for chlorambucil binding to rabbit immunoglobulin G (Blakeslee, D. and Kennedy, J. C., *Cancer Res.* 34:882-885, 1974). Parameters such as temperature, time of reaction, molar concentrations and stoichiometry, ionic strength and pH were analyzed. Researchers found that conditions which favor non-covalent attachment of chlorambucil to IgG include: low ionic strength (down to 0 mM NaCl), high pH (up to 11.5), increased time (up to 30 minute reaction time), and higher temperature of reaction (up to 37° C.).

On the other hand, IgG in solution is known to aggregate spontaneously over time, and this aggregation is via the Fc region. A highly alkaline environment disaggregates IgG into monomers, and this may allow otherwise masked binding sites available for binding.

In one embodiment, the methods include combining TGF-beta protein and Ig (e.g., IgG), such as recombinant IgG, under conditions whereby they associate, such as by non-covalent bond. Incubation and binding typically is followed by purification, such as by any well-known protein purification methods including chromatography.

The proteins can be combined under different buffer and temperature conditions and should be combined under conditions whereby the Ig and TGF-beta portions associate via non-covalent bond. Optimal conditions can be determined based on experimentation, for example as described in Example 1. For example, among the buffers for use in combining the TGF-beta and Ig portions are PBS (phosphate buffered saline) and 0.1M Tris pH 7.4. These buffers can further include glycerol, such as 10% glycerol. Also among the suitable buffers are buffers with higher pH values, such as 0.5 M PBS supplemented with NaOH to a pH of 11.

In one particular embodiment, the buffer is a relatively low-hydrophobicity and/or non-polarizing buffer (such as a buffer containing no or little NaCl concentration (e.g., less than at or about 0.15 mM NaCl), e.g., 0.1M Tris pH 7.4.). In one aspect, the buffer does not contain glycerol. In another embodiment, the buffer is an alkaline buffer, such as a buffer with a pH of at least at or about 7, and typically at least at or about 8, 9, 10, 11, or 12, such as PBS (or 0.5×PBS) at a pH of 11.

In one aspect, such a buffer is made by diluting PBS with NaOH or other base to a pH of 11, where the buffer contains 0.5×PBS (0.075 mM NaCl). In one example, the TGF-beta protein is suspended in 4 mM HCL, and added to Ig solution in PBS, and the solution diluted in PBS, such as PBS or 0.5×PBS having an alkaline pH, such as a pH of at least at or about 7, and typically at least at or about 8, 9, 10, 11, or 12.

Typical incubation temperatures include room temperature (e.g., at or about 25° C.) and higher temperatures, such as 42° C. The time of incubation (binding) also can vary, and can include 1, 2, 3, 4, 5, 6, 7, 8, 9, 10, 15, 20, 25, 30, or 60 minutes, or 2, 3, 4, 5, 6, 7, 8, 9, 10, 15, 16, 17, 18, 19, 20, 21, 22, 23, or 24 hours or more.

In one example, human InTIGG is produced as follows: Total human gamma globulin (available commercially as human "IVIG") is resuspended to a final concentration of 10 mg/ml, for example, in PBS or water. Transforming growth factor-beta is resuspended in 4 mM hydrochloric acid to a final concentration of 100 ng/ml. The TGF-beta solution is added to the IVIG solution at a molar concentration of at least 10:1 IgG to TGF-beta and mixed. To this mixture, an equal volume of PBS (titrated to pH 11 with sodium hydroxide) is added, mixed, and incubated at room temperature for 5 minutes. This solution is then adjusted to pH 7.4 and purified by chromatography.

In one example, human AcTIGG is produced as follows: Human IgG4 is resuspended to a final concentration of 10 mg/ml, for example, in PBS or water. Transforming growth factor-beta is resuspended in 4 mM hydrochloric acid to a final concentration of 100 ng/ml. The TGF-beta solution is added to the IgG4 solution at a molar concentration of at least 10:1 IgG to TGF-beta and mixed. To this mixture, an equal volume of PBS (titrated to pH 11 with sodium hydroxide) is added, mixed, and incubated at room temperature for 5 minutes. This solution is then adjusted to pH 7.4 and purified by chromatography.

In some examples, the TIGG is purified by polyethylene glycol (PEG) precipitation, such as by incubating with PEG, such as PEG8000 (e.g., 8%), centrifuging and washing the pellet in one or more washes; one such procedure is described in Example 3, below. In another example, the TIGG is purified by adding the TIGG to a column, such as a Sepharose G-50 spin column, or a Superdex 200 HR 10/30 (Vt: 24 ml), 1.0 ml/min (76 cm/h) column, which can be equilibrated with 0.05 M sodium phosphate, 0.15 M NaCl, pH 7.0.

The proteins eluting from the column can be monitored to determine binding of the TGF-beta and Ig portions, such as by size determination, for example, using free TGF-beta and/or TIGG complexes as a control. In one example, the presence of protein in the fractions eluted from the column is measured by determining the absorbance of the fractions at 280 nm and/or by analyzing the fractions for TGF-beta presence by ELISA. Such methods are well-known in the art.

Also among the provided complexes and proteins are those containing TGF-beta and IgG portions that are prepared by other known methods for associating two proteins, such as by covalent bonds, and/or using peptide linkers to link the TGF-beta and Ig portions (e.g., by generating nucleic acid vectors encoding the peptide linkers and the proteins), using methods known in the art, such as methods for making fusion proteins containing an Ig and a TGF-beta portion.

vii. Methods for Evaluating the TGF-Beta Containing Complexes

As noted, in one embodiment, the TIGGs are used to target cells of the immune system, such or treating cancer and autoimmunity, and include TIGGs that target for suppression cells expressing higher and lower relative levels of inhibitory and activating FcγRs. Thus, the TIGGs (and portions thereof) typically are defined in part by functional properties, such as their ability to bind and target particular cell types, e.g., by binding to particular FcγRs, and their TGF-beta activity.

Methods are provided for evaluating properties of the provided proteins and complexes, e.g., the TIGGs and portions thereof. The methods include evaluation of properties, e.g., binding affinities and activity, in vitro, and in vivo methods to assess targeting of cell types and in vivo effects of the TIGGs.

a. Binding Affinities

Binding affinity of the TIGG and portions thereof for other molecules, typically for Fc receptors and/or TGF-beta receptors can be specified, and can be determined using well-known methods. The affinity can be measured using well known methods and expressed using well-known units of affinity (e.g., $K_a$, $K_d$, $K_D$). Typically, the affinity is specified by expressing a ratio or percentage of the affinity of the TIGG for the molecule, compared to the affinity of another Ig protein or complex for that molecule (e.g., for a particular Fc receptor), or compared to the affinity of the TIGG for another molecule (e.g., another class of Fc receptor), such as in an A/I ratio.

A/I ratios specify the relative affinity of the Ig proteins and TIGGs for activating versus inhibitory Fc receptors. The A/I ratio of the TIGG is calculated by determining the ratio of the binding affinity of that protein or complex for an activating Fc receptor (either FcγRIII or FcγRIV) to the affinity of the protein or complex for the inhibitory Fc receptor FcγRIIB. The affinity for the respective receptors can be determined using a number of well known experimental techniques, including in vitro assays for measuring protein affinities (See, e.g., Nimmerjahn and Ravetch (*Science*, 310:1510-1512, 2005); Nimmerjahn et al. (*Immunity*, 23: 41-51 (2005); and Armour, K L et al., (*Mol Immunol*, 40:585-593, 2003)), The A/I ratio then is calculated by dividing the affinity for the activating receptor by the affinity for the inhibitory receptor (See, e.g., Nimmerjahn and Ravetch (*Science*, 310:1510-1512, 2005); and Nimmerjahn et al. (*Immunity*, 23: 41-51 (2005)). Thus, the A/I of a molecule, which can be expressed as a fraction or a number (e.g., 1/2, 1:2, or 0.5; or 2/1; 2:1 or 2), is a ratio of the affinity of the molecule for activating Fcγ receptors (sFcγRIII or sFcγRIV) compared to its affinity for the inhibitory receptor FcγRIIB).

Affinities of proteins or complexes (e.g., Ig proteins) for Fc receptors can be determined using well-known experimental techniques, such as those described, for example, by: Nimmerjahn and Ravetch (*Science*, 310:1510-1512, 2005); Nimmerjahn et al. (*Immunity*, 23: 41-51 (2005); and Armour, K L et al., *Mol Immunol*, 40:585-593, 2003. For example, affinities ($K_A$) of proteins or complexes for FcγRs can be measured by a variety of kinetic and thermodynamic assays, including optical detection as BIAcore and RIfS, equilibrium titration and stopped-flow fluorescence. In one aspect, binding affinities are determined using the assays set out in the examples. In one aspect, the affinities are determined by surface plasmon resonance as described by Nimmerjahn and Ravetch (*Science*, 310:1510-1512, 2005) (see supplemental online materials). Briefly, a Biacore sensor system is used to assay the interaction of soluble FcγRs with the proteins by immobilizing the proteins at high and low densities to flow cells of CMS sensor chips (Biacore) by standard amine coupling. Soluble Fcγ-receptors are injected at different concentrations through flow cells at room temperature in HBS-EP running buffer (10 mM Hepes, pH 7.4, 150 mM NaCl, 3.4 mM EDTA, and 0.005% surfactant P20) at a flow rate of 30 µl/min Soluble Fc-receptors are injected for 3 minutes and dissociation of bound molecules is observed for 10 minutes. Background binding to control flow cells is subtracted automatically. Control experiments can be performed to exclude mass transport limitations. Affinity constants are derived from sensorgram data using simultaneous fitting to the association and dissociation phases and global fitting to all curves in the set. Alternatively, soluble Fc-receptors can be immobilized to sensor chips. Affinities can also be measured by flow cytometry, for example, as described by Armour, K L et al., *Mol Immunol*, 40:585-593, 2003, and by other known techniques for measuring binding affinities of proteins. Affinities can be measured for any of the Fc receptors and variants of Fc receptors, including, but not limited to, activating Fc receptors (including FcγRI, FcγRIIa, FcγRIII and FcγRIV) and inhibitory Fc receptors (e.g., sole naturally occurring inhibitory Fc receptor, FcγRIIb).

b. Activity

Also provided are methods for evaluating other properties of the complexes and proteins, e.g., the TIGGs and proteins thereof, such as measuring activities and in vitro and in vivo effects. For example, the TGF-beta activity of a TIGG, or TGF-beta portion or protein thereof, can be measured using a number of well-known techniques, including in vivo and in vitro assays, such as soft agar assays, ability to inhibit proliferation, survival, growth and/or differentiation of a TGF-beta receptor-expressing cells and/or cells known to be inhibited by TGF-beta (in vivo or in vitro), and radioreceptor assays and assays for measuring the production of various cytokines and/or chemokines by cells incubated with the TIGG (for example, as compared to cells incubated with wild-type TGF-beta). Assays for measuring activity further include assays for assessing the ability of a TIGG or portion to target a particular cell type and/or to treat a disease or condition and/or associated symptom.

In one embodiment, the TIGGs and/or portions thereof are evaluated by incubating the complexes in vitro with one or more cell types, or administering the TIGGs to a subject, e.g., non-human animal or human, and monitoring the effects on the cells, such as whether the TIGGs alter the ratio of cell types expressing activating versus inhibitory Fc receptors. While FcγR are expressed in most immune cell types, and altering the relative number of cells in vivo expressing activating and inhibitory FcγRs would affect many of these immune cell phenotypes, assay of the efficacy of the TIGGs can be assessed by evaluating specific cell types and/or readouts of the functions of such cell types. In one example, a TIGG that alters this ratio is most effectively assayed by evaluating the expression pattern of monocytes, such as macrophages. In one aspect, the macrophages are isolated from animals treated by the test material. In another aspect, the monocytes are assayed following treatment with the product in vitro.

It is well known that activating and inhibitory macrophages secrete differential amounts of different cytokines and chemokines. For example, monocyte-lineage cells (e.g., macrophages) can be classified into the M1 (activating, inflammatory) and M2 (inhibitory) phenotype based on function and on expression patterns of proteins including cytokines, chemokines, surface receptors, apoptosis-related genes, soluble carriers, enzymes, extracellular mediators, and DNA binding factors. For example, M1 macrophages express 212 times more CXCL11 chemokine as inhibitory macrophages (M2), whereas inhibitory macrophage express 38 times more CCL13 than activating macrophages (Martinez, F O et al, *J Immunol* 177:7303-7311, 2006). M1 macrophages express and secrete greater than 50-fold more CXCL11, CCL19, CXCL10, and CXCL9 compared to M2. CCL13, CCL18, and CCL23 expression is more than 10-fold higher in M2 macrophages compared to M1. Among membrane proteins, over 100-fold more CCR7 receptor is expressed in M1 vs M2, and mannose receptor C type 1 is expressed 43 times more in M2 vs M1 macrophages. Differentiation of M1 versus M2 macrophages is well established and has been verified and extensively characterized based on different cytokine secretion profiles following *E. coli* lipopolysaccharide (LPS) challenge. After LPS challenge in culture, M1 macrophages overproduce tumor necrosis factor-alpha (TNF-alpha) and interferon-gamma (IFN-γ), whereas M2 macrophages overproduce monocyte chemotactic protein-1 (MCP-1) and interleukin-10 (IL-10). Secretion of cytokines and chemokines, the surface expression and activity of various cell surface receptors, can be evaluated using well-known techniques, such as ELISA, ELISPOT, Immunofluorescence, western blot, RT-PCR, flow cytometry, and other techniques that are known to the skilled artisan. Specific examples of methods for evaluating TIGGs are described in the Examples below.

For example, provided are methods for evaluating InTIGG, when incubated with purified or enriched macrophages before being activated with *E. coli* LPS, will alter the phenotype of the cultured macrophages. In one aspect, the InTigg treated macrophages will produce 5%, 10%, 15%, 20%, 25% or more MCP1 protein in culture compared to untreated, similarly cultured and activated macrophages. In another aspect, the InTigg treated macrophages will produce 5%, 10%, 15%, 20%, 25% or more of IL-10 protein in culture compared to untreated, similarly cultured and activated macrophages.

AcTigg, when incubated with purified or enriched macrophages before being activated with *E. coli* LPS, will alter the phenotype of the cultured macrophages. In one aspect, the AcTigg treated macrophages will produce 5%, 10%, 15%, 20%, 25% or more TNF-alpha protein in culture compared to untreated, similarly cultured and activated macrophages. In another aspect, the AcTigg treated macrophages will produce 5%, 10%, 15%, 20%, 25% or more of IFN-γ protein in culture compared to untreated, similarly cultured and activated macrophages.

Also provided are methods for evaluating the in vivo effects of the complexes, e.g., the TIGGs. For example, to evaluate whether an InTIGG will ameliorate an autoimmune disease in vivo, a mouse model of rheumatoid arthritis can be used. In this example, the mouse analog of the human immunoglobulin portion is used. It is known that among mouse immunoglobulin subtypes, mouse IgG2a displays the highest A/I ratio (Nimmerjahn F and Ravetch, J V, 2005, ibid) of the naturally occurring mouse IgG subtypes. In one example, mice are injected three times a week for two weeks with 50 nanograms TGF-beta-bound mouse IgG2a three days after arthritis inflammation commences. Articular swelling is compared to that in mice treated with phosphate buffered saline.

To determine whether AcTIGG ameliorates tumor growth and metastases in vivo, a mouse model of metastatic melanoma can be used. In this example, the mouse analog of the human immunoglobulin portion is used. It is known that among mouse immunoglobulin subtypes, mouse IgG1 displays the lowest A/I ratio (Nimerjahn F and Ravetch, J V, 2005, ibid) of the naturally occurring mouse IgG subtypes. Mice can be injected three times a week for two weeks with 50 nanograms TGF-beta bound mouse IgG1 three days after tumor cells are injected, and tumor burden evaluated compared to that in mice treated with phosphate buffer saline.

C. THERAPEUTIC APPLICATIONS

Provided are methods for using the provided TGF-beta containing complexes, such as the TIGGs, including the AcTIGGs and InTIGGs. Also provided are methods and uses for administration of a therapeutic composition comprising one or more InTIGGs to an individual diagnosed with autoimmune disease. Also provided are methods and uses for the administration of a therapeutic composition comprising one or more AcTIGGs to an individual diagnosed with cancer.

For example, provided are methods for suppressing cells (e.g., inhibiting cell growth, proliferation, survival and/or differentiation) using the provided TIGGs. Among the provided methods are methods for administering the TIGGs to subjects, such as non-human animals and humans, for example for treatment, prevention or amelioration of a disease or condition, such as diseases and conditions associated with inflammation or immunosuppression. Typically, the TGF-beta containing complexes target suppression of particular cells. In one aspect, the targeted cells are immune cells, such as the immune cells that are drawn to the site of the injected protein via the natural chemotactic properties of TGF-beta for these cells, or those that encounter the free product in the lymph or circulatory system, and which possess Fcγ receptors. These immune cells may include B cells, monocytes, PMNs, mast cells, and neutrophils, among others.

For example, the provided AcTIGGs can be used for treatment of diseases, such as cancer, that are associated with immunosuppression, e.g., diseases in which immunosuppression is a major contributing factor to the disease, is a marker for the disease or for poor prognosis of the disease, is a side effect of the disease or produces or increases the severity of a symptom of the disease. Typically, the AcTIGGs activate aspects of the immune system to overcome the inherent immune suppression of the disease being treated.

The provided InTIGGs can be used for treatment of diseases, such as autoimmune disease, associated with immune over-stimulation or inflammation, for example, diseases in which immune over-stimulation or inflammation is a major contributing factor to the disease, is a maker for the disease or for poor prognosis in the disease, is a side effect of the disease, or produces or increases the severity of a symptom of the disease. Typically, the InTIGGs suppress aspects of the immune system to overcome the inherent immune overactivity of the disease being treated.

In addition to targeting cells with a preponderance of either activating or inhibitory FcγRs, the provided TIGG complexes and compositions containing the TIGGs overcome problems and limitations associated with free TGF beta administration, e.g., administration (e.g., injection) of TGF-beta not associated with Ig portions. For example, active TGF-beta can have a short in vivo half-life (2-3 minutes in rats and rabbits) when injected i.v., and can have pleiotropic activity (on a plurality of cells and tissues, such as throughout the body). Pleiotropic activity can have problematic effects, for example, by acting on tissues and/or cell types where activity is not desired.

The provided complexes overcome these limitations. For example, among the provided complexes are those having increased half-lives, compared to TGF-beta not associated with Ig molecules. For example, provided are complexes having half-lives greater than at or about 2 minutes, 3 minutes, 4 minutes, 5 minutes, 1 hour, 2 hours, 3 hours, 5 hours, 10 hours or 24 hours, and having TGF-beta activity, such as substantially the same TGF-beta activity, or greater, compared to wild-type active TGF-beta.

Further, the complexes and compositions can target immune cells specifically, such as cells expressing Fc receptors (e.g., Fc gamma receptors), and in particular can target specific immune cell types that drive autoimmunity or that contribute to immunosuppression (e.g., immunosuppression of tumors), tumor growth and other tumor symptoms.

i. Methods of Using AcTIGGs

Provided are methods for using the AcTIGGs. For example, administration of the provided AcTIGG protein or AcTIGG-encoding nucleic acid molecules can be either for preventative or therapeutic purpose. When provided preventatively, the therapeutic agent is provided in advance of any symptoms. The preventative administration of the therapeutic agent serves to prevent or attenuate any symptoms. When provided therapeutically the therapeutic agent is provided at (or shortly after) the onset of a symptom of the cancer or autoimmune disease. The therapeutic administration of the therapeutic agent serves to attenuate any actual exacerbation of the symptoms. The individual treated may be any mammal. In one aspect, the mammal is a human.

The subject treated by the present methods includes a subject having a tumor susceptible to treatment. Such tumors can be a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. Tumors treated by compounds of the present methods include, but are not limited to: neoplasm of the central nervous system: glioblastoma multiforme, astrocytoma, oligodendroglial tumors, ependymal and choroids plexus tumors, pineal tumors, neuronal tumors, medulloblastoma, schwannoma, meningioma, meningeal sarcoma: neoplasm of the eye: basal cell carcinoma, squamous cell carcinoma, melanoma, rhabdomyosarcoma, retinoblastoma; neoplasm of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors: neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, vermiform appendix and peritoneum, adenocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, non-small cell lung cancer; adenocarcinoma of the uterine corpus, ovarian cancer, gynecologic sarcomas; neoplasms of the breast; neoplasms of the skin: basal cell carcinoma, squamous carcinoma, dermatofibrosarcoma, Merkel cell tumor; malignant melanoma; neoplasms of the bone and soft tissue: osteogenic sarcoma, malignant fibrous histiocytoma, chondrosarcoma, Ewing's sarcoma, primitive neuroectodermal tumor, angiosarcoma; neoplasms of the hematopoietic system: myelodysplastic syndromes, acute myeloid leukemia, chronic myeloid leukemia, acute lymphocytic leukemia, HTLV-1, and T-cell leukemia/lymphoma, chronic lymphocytic leukemia, hairy cell leukemia, Hodgkin's disease, non-Hodgkin's lymphomas, mast cell leukemia; neoplasms of children: acute lymphoblastic leukemia, acute myelocytic leukemias, neuroblastoma, bone tumors, rhabdomyosarcoma, lymphomas, renal and liver tumors.

ii. Methods of Using InTIGGs

Also provided are methods for administration of the InTIGGs. Administration of the provided InTIGG protein or InTIGG-encoding nucleic acid molecules can be either for preventative or therapeutic purpose. When provided preventatively, the therapeutic agent is provided in advance of any symptoms. The preventative administration of the therapeutic agent serves to prevent or attenuate any symptoms. When provided therapeutically the therapeutic agent is provided at (or shortly after) the onset of a symptom of the autoimmune disease. The therapeutic administration of the therapeutic agent serves to attenuate any actual exacerbation of the symptoms. The individual treated may be any mammal. In one aspect, the mammal is a human.

The subject treated by the present methods includes a subject having Addison's Disease, autoimmune hemolytic anemia, autoimmune inner ear disease, autoimmune lymphoproliferative syndrome, autoimmune thrombocytopenic purpura, autoimmune hemolytic anemia, autoimmune hepatitis, autoimmune oophoritis, Behçet's disease, autoimmune bullous pemphigoid, autoimmune cardiomyopathy, Crohn's disease, autoimmune chronic fatigue syndrome, chronic obstructive pulmonary disease (COPD), including chronic bronchitis, emphysema and chronic asthmatic bronchitis, autoimmune dermatomyositis, autoimmune diabetes mellitus type-1, autoimmune epilepsy autoimmune, Kawasaki's disease, autoimmune glomerulonephritis, Grave's disease, Goodpasture's syndrome, Guillain-Barré syndrome, lupus nephritis, multiple sclerosis, myasthenia gravis, autoimmune myocarditis, autoimmune Parkinson diseases, pediatrics autoimmune neuropsychiatry disorders, autoimmune pemphigus/pemphigoid, autoimmune pernicious anemia, autoimmune polyarteritis nodosa, autoimmune polymyositis, autoimmune primary biliary cirrhosis, psoriasis, autoimmune rheumatic fever, rheumatoid arthritis, autoimmune sarcoidosis, scleroderma, Sjogren's syndrome, autoimmune thyroiditis, autoimmune ulcerative colitis, autoimmune uveitis, autoimmune vitiligo, Wegener's granulomatosis, and Wilson's disease.

In one aspect, the autoimmune disease is a T-cell mediated autoimmune disease.

D. PHARMACEUTICAL COMPOSITIONS, DOSING AND ADMINISTRATION

Various routes of administration and dosing regimens can be used for administering a therapeutically effective amount of AcTIGG or InTIGG to a human. The provided therapeutic composition can be administered by any of the conventional routes of administration. Also, the therapeutic composition can be in any of several conventional dosage forms. In one aspect, the therapeutic composition is administered by subcutaneous or intraperitoneal injection.

The AcTIGG or InTIGG may be administered subcutaneously, transdermally, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The AcTIGG or InTIGG may also be administered or co-administered in slow release dosage forms.

The dose at which the AcTIGG or InTIGG may be administered to a human may vary, depending on the particular route of administration and the disease state.

For example, the AcTIGG may be administered at a dose of at least 0.0001 mg, optionally at least 0.001 mg, optionally at least 0.01 mg, optionally at least 0.05 mg, optionally at least 0.1 mg, optionally at least 0.5 mg, or optionally at least 1 mg. In other embodiments, the AcTIGG may be administered at a dose of 0.01-1000 mg, optionally at a dose of 0.1-500 mg, optionally at a dose of 1-200 mg, optionally at a dose of 1-100 mg, optionally at a dose of 1-50 mg, optionally at a dose of 1-20 mg, optionally at a dose of 0.1-5 mg, or optionally at a dose of about 1-5 mg.

For example, the InTIGG may be administered at a dose of at least 0.0001 mg, optionally at least 0.001 mg, optionally at least 0.01 mg, optionally at least 0.05 mg, optionally at least 0.1 mg, optionally at least 0.5 mg, or optionally at least 1 mg. In other embodiments, the InTIGG may be administered at a dose of 0.01-1000 mg, optionally at a dose of 0.1-500 mg, optionally at a dose of 1-200 mg, optionally at a dose of 1-100 mg, optionally at a dose of 1-50 mg, optionally at a dose of 1-20 mg, optionally at a dose of 0.1-5 mg, or optionally at a dose of about 1-5 mg.

In still further embodiments, the AcTIGG may be administered a human at a dose calculated based on the suffer area of the human, e.g., at dose of 0.01-1000 mg/m$^2$, optionally at dose of 0.1-500 mg/m$^2$, optionally at dose of 1-200 mg/m$^2$, optionally at dose of 1-100 mg/m$^2$, optionally at dose of 1-50 mg/m$^2$, optionally at dose of 1-20 mg/m$^2$, optionally at dose of 0.1-5 mg/m$^2$, or optionally at dose of 1-5 mg/m$^2$.

In still further embodiments, the InTIGG may be administered a human at a dose calculated based on the suffer area of the human, e.g., at dose of 0.01-1000 mg/m$^2$, optionally at dose of 0.1-500 mg/m$^2$, optionally at dose of 1-200 mg/m$^2$, optionally at dose of 1-100 mg/m$^2$, optionally at dose of 1-50 mg/m$^2$, optionally at dose of 1-20 mg/m$^2$, optionally at dose of 0.1-5 mg/m$^2$, or optionally at dose of 1-5 mg/m$^2$.

The treatment cycle for AcTIGG or InTIGG may be administered once, or more than once. For example, it can be administered weekly, biweekly, monthly, or on an as-needed basis. In other aspects, it is administered once, twice per day or more times per day. The treatment may be given in conjunction with other therapeutic agents or before or after surgery.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as *Remington: The Science and Practice of Pharmacy* 20 th Ed. (Lippincott, Williams & Wilkins 2003).

It is further understood that the provided polypeptides may be used in the form of pharmaceutically acceptable salts, and that any reference herein to pharmaceutical compositions comprising the polypeptides also refers to said salts. Pharmaceutically-acceptable materials, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Combinations and articles of manufacture, such as kits, comprising the compositions are also provided.

E. GENE THERAPY

Nucleic acid molecules encoding the proteins and complexes provided herein can be used in gene therapy. Thus, also provided are methods for using the provided molecules for gene therapy, and vectors and viruses for gene therapy.

Also provided are recombinant DNA vectors or recombinant viruses containing a nucleic acid encoding both the TGF-beta portion and the immunoglobulin portion of AcTIGG or InTIGG, or fragments or variants thereof.

References describing a variety of viral delivery vectors are known in the art, some of which are cited herein.

Such vectors include, for example, viral vectors (such as adeno-associated viruses (AAV), liposomes and other lipid-containing complexes, and other macromolecular complexes capable of mediating delivery of a polynucleotide to a host cell. As described above and in the cited references, vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., Lupton, S., WO 92/08796, published 29 May 1992; and Lupton, S., WO 94/28143, published 8 Dec. 1994). Such marker genes can provide an added measure of control that can be advantageous in gene therapy contexts. A large variety of such vectors is known in the art and are generally available (see, e.g., the various references cited above).

Additional references describing adenovirus vectors and other viral vectors which could be used in the methods provided herein include the following: Horwitz, M. S., "Adenoviridae and Their Replication," in Fields, B., et al. (eds.) *Virology*, Vol. 2, Raven Press New York, pp. 1679-1721, 1990); Graham, F., et al., pp. 109-128 in *Methods in Molecular Biology*, Vol. 7: *Gene Transfer and Expression Protocols*, Murray, E. (ed.), Humana Press, Clifton, N.J. (1991); Miller, N., et al., *FASEB Journal* 9: 190-199, 1995; Schreier, H, *Pharmaceutica Acta Helvetiae* 68: 145-159, 1994; Schneider and French, *Circulation* 88:1937-1942, 1993; Curiel D. T., et al., *Human Gene Therapy* 3: 147-154, 1992; Graham, F. L., et al., WO 95/00655 (5 Jan. 1995); Falck-Pedersen, E. S., WO 95/16772 (22 Jun. 1995); Denefle, P. et al., WO 95/23867 (8 Sep. 1995); Haddada, H. et al., WO 94/26914 (24 Nov. 1994); Perricaudet, M. et al., WO 95/02697 (26 Jan. 1995); Zhang, W., et al., WO 95/25071 (12 Oct. 1995). A variety of adenovirus plasmids are also available from commercial sources, including, e.g., Microbix Biosystems of Toronto, Ontario (see, e.g., *Microbix Product Information Sheet: Plasmids for Adenovirus Vector Construction*, 1996).

Additional references describing AAV vectors which can be used in the provided methods include the following: Carter, B., *Handbook of Parvoviruses, vol. I*, pp. 169-228, 1990; Berns, *Virology*, pp. 1743-1764 (Raven Press 1990); Carter, B., *Curr. Opin. Biotechnol.*, 3: 533-539, 1992; Muzyczka, N., *Current Topics in Microbiology and Immunology*, 158: 92-129, 1992; Flotte, T. R., et al., *Am. J. Respir. Cell Mol. Biol.* 7:349-356, 1992; Chatterjee et al., *Ann. NY Acad. Sci.*, 770: 79-90, 1995; Flotte, T. R., et al., WO 95/13365 (18 May 1995); Trempe, J. P., et al., WO 95/13392 (18 May 1995); Kotin, R., *Human Gene Therapy*, 5: 793-801, 1994; Flotte, T. R., et al., *Gene Therapy* 2:357-362, 1995; Allen, J. M., WO 96/17947 (13 Jun. 1996); and Du et al., *Gene Therapy* 3: 254-261, 1996.

Additional references describing non-viral vectors which could be used in the provided methods include the following: Ledley, F D, *Human Gene Therapy* 6: 1129-1144, 1995; Miller, N., et al., *FASEB Journal* 9: 190-199, 1995; Chonn, A., et al., *Curr. Opin. in Biotech.* 6: 698-708, 1995; Schofield, J P, et al., *British Med. Bull.* 51: 56-71, 1995; Brigham, K. L., et al., *J. Liposome Res.* 3: 31-49, 1993; Brigham, K. L., WO 91/06309 (16 May 1991); Felgner, P. L., et al., WO 91/17424 (14 Nov. 1991); Solodin et al., *Biochemistry* 34: 13537-13544, 1995; WO 93/19768 (14 Oct. 1993); Debs et al., WO 93/25673; Felgner, P. L., et al., U.S. Pat. No. 5,264,618 (Nov. 23, 1993); Epand, R. M., et al., U.S. Pat. No. 5,283,185 (Feb. 1, 1994); Gebeyehu et al., U.S. Pat. No. 5,334,761 (Aug. 2, 1994); Felgner, P. L., et al., U.S. Pat. No. 5,459,127 (Oct. 17, 1995); Overell, R. W., et al., WO 95/28494 (26 Oct. 1995); Jessee, WO 95/02698 (26 Jan. 1995); Haces and Ciccarone, WO 95/17373 (29 Jun. 1995); Lin et al., WO 96/01840 (25 Jan. 1996).

For purposes of illustrating vector-mediated gene delivery of a polynucleotide encoding one or more monomers of TGF-beta and one or more immunoglobulin heavy and light chains (an "AcTIGG-encoding polynucleotide or nucleic acid" or an "InTIGG-encoding polynucleotide"), an adenovirus vector can be constructed by the rescue recombination technique as described in McGrory W J, et al., *Virology* 163:614-617, 1988. Briefly, the transgene of interest is cloned into a shuttle vector that contains a promoter, polylinker and partial flanking adenovirus sequences from which E1A/E1B genes have been deleted.

Illustrative shuttle vectors include, e.g., plasmid "pAC1" (*Virology* 163:614-617, 1988) (or an analog) which encodes portions of the left end of the human adenovirus 5 genome but lacks the early protein region comprising E1A and E1B sequences that are essential for viral replication; and plasmid "ACCMVPLPA" (*J Biol Chem* 267:25129-25134, 1992) which contains a polylinker, CMV promoter and SV40 polyadenylation signal flanked by partial adenovirus sequences from which the E1A/E1B genes have been deleted. The use of plasmids such as pAC1 or ACCMVPLA can thus facilitate the cloning process.

The shuttle vector can then be co-transfected, along with a plasmid comprising the entire human adenovirus 5 genome (but with a length too large to be encapsidated), into suitable host cells such as human 293 cells. Co-transfection can be conducted by calcium phosphate precipitation or lipofection (see, e.g., *Biotechniques* 15:868-872, 1993).

As an illustrative plasmid for co-transfection, plasmid "JM17" encodes the entire human adenovirus 5 genome plus portions of the vector pBR322 including the gene for ampicillin resistance (4.3 kb) (Giordano, et al. *Nature Medicine* 2: 534-539, 1996). Although JM17 encodes all of the adenovirus proteins necessary to make mature viral particles, it is too large to be encapsidated (40 kb versus 36 kb for wild type).

In a small subset of co-transfected cells, "rescue recombination" occurs between the transgene-containing shuttle vector (such as plasmid pAC1) and the plasmid having the entire adenovirus 5 genome (such as plasmid pJM17) which generates a recombinant genome that contains the transgene of interest in place of the deleted E1A/E1B sequences, and that secondarily loses the additional sequence (such as pBR322 sequences) during recombination, thereby being small enough to be encapsidated (see, e.g., Giordano, et al. *Nature Medicine* 2:534-539, 1996). The CMV driven-galactosidase gene in adenovirus HCMVSP1lacZ (*Nature Medicine* 2: 534-539, 1996) can be used to evaluate the efficiency of gene transfer using X-gal treatment.

A variety of other vectors suitable for in vivo gene therapy can also be readily employed to deliver AcTIGG-encoding transgenes or InTIGG-encoding transgenes in accordance with the provided embodiments. Such other vectors include, by way of illustration, other viral vectors such as adeno-associated virus (AAV) vectors; non-viral protein-based delivery platforms); as well as lipid-based vectors (including, e.g., cationic liposomes and analogous gene delivery complexes. The preparation and use of these and other vectors are described in the art (see, e.g., the references regarding gene delivery vectors cited above).

As described above, in certain aspects, the provided AcTIGG and InTIGG retains its chemotaxis toward immune cells, and thus attracts immune cells to the site of injection and/or site of transgene expression. In other aspects, the transgene may be targeted. For example, cell targeting may be achieved not only by delivery of the transgene into the specific tissue to be treated in the mammal or by subcutaneous injection, for example, but also by use of targeted vector constructs having features that tend to target gene delivery and/or gene expression to particular host cells or host cell types. Such targeted vector constructs would thus include targeted delivery vectors and/or targeted vectors, as described in more detail below and in the published art. Restricting delivery and/or expression can be beneficial as a means of further focusing the potential effects of gene therapy. The potential usefulness of further restricting delivery/expression depends in large part on the type of vector being used and the method and place of introduction of such vector.

Targeted delivery vectors include, for example, vectors (such as viruses, non-viral protein-based vectors and lipid-based vectors) having surface components (such as a member of a ligand-receptor pair, the other half of which is found on a host cell to be targeted) or other features that mediate preferential binding and/or gene delivery to particular host cells or host cell types. As is known in the art, a number of vectors of both viral and non-viral origin have inherent properties facilitating such preferential binding and/or have been modified to effect preferential targeting (see, e.g., Miller, N., et al., *FASEB Journal* 9: 190-199, 1995; Chonn, A., et al., *Curr. Opin. in Biotech.* 6: 698-708, 1995; Schofield, J P, et al., *British Med. Bull.* 51: 56-71, 1995; Schreier, H, *Pharmaceutica Acta Helvetiae* 68: 145-159, 1994; Ledley, F D, *Human Gene Therapy* 6: 1129-1144, 1995; Conary, J. T., et al., WO 95/34647 (21 Dec. 1995); Overell, R. W., et al., WO 95/28494 (26 Oct. 1995); and Truong, V. L. et al., WO 96/00295 (4 Jan. 1996)).

Targeted vectors include vectors (such as viruses, non-viral protein-based vectors and lipid-based vectors) in which delivery results in transgene expression that is relatively limited to particular host cells or host cell types.

Recombinant viral vectors, such as adenoviral vectors, can be plaque purified according to standard methods. By way of illustration, recombinant adenoviral viral vectors can be propagated in human 293 cells (which provide E1A and E1B functions in trans) to titers in the preferred range of about $10^{10}$-$10^{12}$ viral particles/ml.

Propagation and purification techniques have been described for a variety of viral vectors that can be used in conjunction with the provided embodiments. Adenoviral vectors are exemplified herein but other viral vectors such as AAV can also be employed. For adenovirus, cells can be infected at about 80% confluence and harvested 48 hours later. After 3 freeze-thaw cycles the cellular debris can be collected by centrifugation and the virus purified by CsCl gradient ultracentrifugation (double CsCl gradient ultracentrifugation is preferred).

Prior to in vivo injection, the viral stocks can be desalted by gel filtration through Sepharose columns such as G25 Sephadex. The product can then be filtered through a 30 micron filter, thereby reducing the potential for deleterious effects associated with injection of unfiltered virus. The resulting viral stock preferably has a final viral titer that is at least about $10^{10}$-$10^{12}$ viral particles/ml.

Preferably, the recombinant adenovirus is highly purified, and is substantially free of wild-type (potentially replicative) virus. For these reasons, propagation and purification can be conducted to exclude contaminants and wild-type virus by, for example, identifying successful recombinants with PCR using appropriate primers, conducting two rounds of plaque purification, and double CsCl gradient ultracentrifugation.

The means and compositions which are used to deliver the vectors carrying AcTIGG-encoding transgenes or InTIGG-encoding transgenes depend on the particular vector employed as is well known in the art. Typically, however, a vector can be in the form of an injectable preparation containing pharmaceutically acceptable carrier/diluent such as saline, for example.

For viral vectors (such as adenovirus), the final titer of the virus in the injectable preparation is preferably in the range of about $10^7$-$10^{13}$ viral particles which allows for effective gene transfer. Other pharmaceutical carriers, formulations and dosages are described above.

F. TRANSGENIC NON-HUMAN ANIMALS

Also provided are transgenic non-human animals containing the provided nucleic acid constructs, including an expression cassette or vector or a transfected or transformed cell comprising a nucleic acid expressing a TIGG-encoding nucleic acid (e.g., In AcTIGG-encoding nucleic acid or InTIGG-encoding nucleic acid) operably linked to promoter and/or enhancer, and non-human animals for evaluating the in vivo activity provided proteins, complexes, e.g., TIGGs, and compositions. For example, the provided proteins and complexes can be evaluated using a number of well-known autoimmune and cancer animal models. Also provided are methods of making and using these transgenic non-human animals.

The transgenic non-human animals can be, e.g., mice, rats, rabbits, dogs, cats, cows, goats, sheep, pigs, horses, and monkeys, comprising a nucleic acid construct as provided herein. These animals can be used, e.g., as in vivo models for TIGG, AcTIGG or InTIGG expression and activity, e.g., as models to screen for compound that can activate AcTIGG or InTIGG gene activity in vivo.

The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) *J. Immunol. Methods* 231:147-157, describing the production of recombinant proteins in the milk of transgenic dairy animals; Baguisi (1999) *Nat. Biotechnol.* 17:456-461, demonstrating the production of transgenic goats. U.S. Pat. No. 6,211,428 describes making and using transgenic non-human mammals which express in their brains a nucleic acid construct comprising a DNA sequence. U.S. Pat. No. 5,387,742 describes injecting cloned recombinant or synthetic DNA sequences into fertilized mouse eggs, implanting the injected egg s in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

Animal Autoimmune Models

Collagen-induced arthritis is a well-known and widely used animal model of rheumatoid arthritis in mice and rats. Bovine collagens are purified from non-articular (sternal) cartilage or purchased commercially. The collagens are prepared by pepsin digestion and salt fractionation according to established procedures (Williams, R. O., *Methods Mol Med* (2004), 98:207-216). DBA/1J mice (males, Jackson Laboratories, P.O. #877440, R #2532, 5-6 weeks old) are immunized intradermally in two sites at the base of the tail with 200 µg of collagen in CFA. CFA is prepared by grinding with pestle and mortar 100 mg of *Mycobacterium tuberculosis* H37Ra (BD Biosciences, San Jose, Calif.) to produce a fine powder and then suspended in 30 ml of incomplete Freund's adjuvant (BD Biosciences, San Jose, Calif.).

For macroscopic assessment of arthritis, the thickness of each affected hind paw is measured daily with microcalipers and the diameter can be expressed as the average for inflamed hind paws per mouse. Animals can also be scored for clinical signs of arthritis as follows: 0=no visible effects of arthritis; 1=edema and erythema of one digit or joint; 2=edema and erythema of two joints; 3=edema and erythema of more than two joints; 4=severe arthritis of the entire paw and digits, accompanied by ankylosis of the ankle and deformity of the limb. Each limb the mouse can be graded, allowing a maximum score of 12 per mouse. For histological assessment of arthritis, treated and control mice are sacrificed, joints decalcified and paraffin-embedded, and 10 µm sections are stained with haematoxylin and eosin for conventional histology.

Another well-known murine model of rheumatoid arthritis in which the provided compositions can be evaluated is the Streptococcal cell wall arthritis cell wall mouse model. For this model, *Streptococcus pyogenes* T12 organisms are cultured in Todd-Hewitt broth for 24 hours and harvested. Cells are disrupted with glass beads and sonicated. The material is treated with degrading enzymes and further isolated by differential ultracentrifugation as described (Williams, R. O., *Methods Mol Med* (2004), 98:207-216). The resulting 10,000 g supernatant is used. Streptococcal cell wall arthritis is induced by a single i.a. injection of 6 µl containing 25 µg (rhamnose content) in saline into the right knee joint of C57BL/6 female mice. Assessment of the degree of arthritis in the injected knee joint is identical to that described in Example 12.

A widely used and validated mouse model for human Multiple Sclerosis is the Experimental Autoimmune Encephalitis (EAE) model. This model is generated and used using well known methods. In one example, twelve week old NOD mice (Jackson Laboratory, Bar Harbor, Me.) are injected by subcutaneous immunization into the flanks with 200 µl of an emulsion containing 150 µg of MOG peptide 35-55 (MEVG-WYRSPFSRVVHLYRNGK (SEQ ID NO:11)) and 400 µg *Mycobacterium tuberculosis* extract H37 Ra (Difco, Detroit, Mich.) in incomplete Freund's adjuvant. The first signs of disease should appear at days 11-12, peaking at days 16-18. After partial recovery from this initial acute attack, there should be a progressive worsening relapse without full remission. Clinical signs of EAE are assessed according to the following scores: 0=no signs of disease, 1=loss of tone in the tail, 2=hind limb paresis, 3=hind limb paralysis, 4=tetraplegia, 5=moribund.

The ability of InTIGG to ameliorate EAE can be tested in this model, e.g., after initial signs of the disease appear, for example as described in Example 12.

A widely accepted mouse model for Colitis/Chron's disease is the dextran sodium sulfate model. For this model, Colitis is induced in eight week old female Swiss-Webster mice (Charles River Laboratories, Inc., Wilmington, Mass.) by feeding 4% dextran sodium sulfate (30-40 kDa, ICN Biochemicals, Costa Mesa, Calif.) ad libitum for 7 days.

On day 8, animals are returned to drinking plain water and therapy is initiated. This model can be used to evaluate the provided complexes and compositions, for example, as described in Example 13, below.

For example, a test group can be treated with one or more injections of InTIGG subcutaneously or interperatonially, whereas the control group can be injected identically with phosphate-buffered saline. Parameters recorded in the experiments are bodyweight, stool consistency and occurrence of occult or gross rectal blood, as described (Cooper H. S., et al., *Lab Invest* (1993), 69(2):238-249).

The non-obese diabetic (NOD) mouse model shows striking similarities to human type-1 diabetes. NOD mice develop diabetes starting around 30 weeks of age in 80% of females and 20% of males; however, cyclophosphamide accelerates its onset. For example, cyclophosphamide has been shown to produce diabetes synchronously in 40-60% of male NOD mice after a single dose (Harada et al., *Diabetologia* (1984) 27:604-606).

In one example, Cyclophosphamide is administered twice, 14 days apart, at a dose of 200 mg/kg in PBS to 8-10 week old female NOD mice (Taconic Farms, Germantown, Md.). Diabetes is diagnosed by regular urinary glucose analysis and confirmed by blood glucose determination. Mice are considered diabetic when sequential blood glucose measurements are shown to be above or equal to 16.7 mmol/L (300 mg/dl), as determined by Accu-ChekIII glucometer, or any other commercially available glucose monitoring device. Disease progression and severity can also be monitored by the degree of insulinitis after necropsy. The pancreas is excised immediately after animal sacrifice and fixed in 10% buffered formalin, and hematoxylin- and eosin-stained histologic slides prepared. Insulinitis is graded as follows: grade 0=normal islet totally free of any periilet mononuclear cells, grade 1=focal periislet lyphocytic infiltration <25% of islet circumference, grade 2=periislet lymphocytic infiltration >25% of islet circumference, grade 3=mild insulitis, with intraislet infiltration with good retention of islet cell morphology, and grade 4=severe insulitis with significant destruction of beta-islet cells. This model can be used to evaluate effects of treatment with the provided compositions, for example, as described in Example 14, below.

Animal Cancer and Tumor Models

A plurality of well-known animal models for cancer exist and can be used with the provided complexes and proteins, such as TIGGs and particularly AcTIGGs. In one embodiment, the cancer model is the tumor model generated by transplanting B16F10 metastatic melanoma cells, such as via tail vein injection, into mice, as described in the Examples below. Other Animal models of cancer are well known and include various genetically modified animal strains. For example, animal models of cancer include mis-match repair models (MMRs). Hereditary nonpolyposis colon cancer (HNPCC), which is caused by germline mutations in MSH2 and MLH1, genes involved in DNA mismatch repair, accounts for 5-15% of colon cancer cases. Mouse models have been generated carrying null mutations in the MLH1, MSH2 and MSH3 genes. Other animal models for cancer include transgenic models (e.g., B66-Min/+mouse); chemical induction models, e.g., carcinogen (e.g., azoxymethane, 2-dimethylhydrazine, or N-nitrosodimethylamine) treated rats or mice; models of liver metastasis from colon cancer such as that described by Rashidi et al. (2000) *Anticancer Res* 20(2A):715; and cancer cell implantation or inoculation models as described in, for example, Fingert et al. (1987) *Cancer Res* 46(14):3824-9 and Teraoka et al. (1995) *Jpn Cancer Res* 86(5):419-23.

Experimental model systems are available for the study of, for example, ovarian cancer (Hamilton, T C et al. *Semin Oncol* (1984) 11:285-298; Rahman, N A et al. *Mol Cell Endocrinol* (1998) 145:167-174; Beamer, W G et al. *Toxicol Pathol* (1998) 26:704-710), gastric cancer (Thompson, J et al. *Int J Cancer* (2000) 86:863-869; Fodde, R et al. *Cytogenet Cell Genet* (1999) 86:105-111), breast cancer (Li, M et al. *Oncogene* (2000) 19:1010-1019; Green, J E et al. *Oncogene* (2000) 19:1020-1027), melanoma (Satyamoorthy, K et al. *Cancer Metast Rev* (1999) 18:401-405), and prostate cancer (Shirai, T et al. *Mutat Res* (2000) 462:219-226; Bostwick, D G et al. *Prostate* (2000) 43:286-294).

Other animal based models for studying tumorigenesis in vivo are well known in the art (reviewed in *Animal Models of Cancer Predisposition Syndromes*, Hiai, H. and Hino, O. (eds.) 1999, *Progress in Experimental Tumor Research*, Vol. 35; Clarke A R *Carcinogenesis* (2000) 21:435-41) and include, but are not limited to, carcinogen-induced tumors (Rithidech, K et al. *Mutat Res* (1999) 428:33-39; Miller, M L et al. *Environ Mol Mutagen* (2000) 35:319-327), as well as animals bearing mutations in growth regulatory genes, for example, oncogenes (e.g., ras) (Arbeit, J M et al. *Am J Pathol* (1993) 142:1187-1197; Sinn, E et al. *Cell* (1987) 49:465-475; Thorgeirsson, S S et al. *Toxicol Lett* (2000) 112-113:553-555) and tumor suppressor genes (e.g., p53) (Vooijs, M et al. *Oncogene* (1999) 18:5293-5303; Clark A R *Cancer Metast Rev* (1995) 14:125-148; Kumar, T R et al. *J Intern Med* (1995) 238:233-238; Donehower, L A et al. (1992) *Nature* 356215-221).

The following examples are offered to illustrate provided embodiments and are not intended to limit the scope of the invention.

G. EXAMPLES

Example 1

Production of TIGGs

This example describes production of mouse TIGGs. The mouse TIGGs were generated in order to evaluate the in vivo effects of the provided TIGGs in mice, for example, in normal mice and in mouse models of cancer and autoimmune disease models. For use in the animal studies, mouse TIGGs were generated, the Ig portions of which contained mouse IgG molecules or fragments (e.g., Fc regions) thereof. For example, as described in Example 1B, below, a mouse InTIGG was produced for evaluation of the provided InTIGGs on amelioration of autoimmune disease in vivo in a mouse model (such as a model of rheumatoid arthritis).

The Ig portion of the mouse InTIGG contained the mouse analog of the human immunoglobulin contained in one of the provided human InTIGGs. It is known that mouse IgG2a displays the highest A/I ratio among the naturally occurring mouse IgG subtypes (Nimmerjahn F and Ravetch, J V, 2005, ibid). Similarly, as also described in Example 1B, below, a mouse AcTIGG was produced for use in evaluation of the effects of the provided AcTIGGs on tumor growth and metastases in vivo in mouse models. The Ig portion of the mouse AcTIGG contained the mouse analog (IgG1) of the human immunoglobulin contained in one of the provided human AcTIGGs. It is known that mouse IgG1 displays the lowest A/I ratio of the naturally occurring mouse IgG subtypes (Nimerjahn F and Ravetch, J V, 2005, ibid).

A. Optimization TGF-Beta Binding to IgG

This example describes the optimization of conditions for generating the mouse TIGG complexes for administration in mice to evaluate in vivo effects of the provided TIGGs. 10 μL 1 mg/mL rat total IgG (Sigma-Aldrich St. Louis, Mo.) first was bound to Nunc Immunosorb plates in 0.1M NaCO$_3$, pH 9.6 overnight at 4° C. The plates were washed with TBST and blocked with 3.5% BSA in TBST for 2 hrs at 37° C. Four different samples containing TGF-beta (Leinco Technologies, St. Louis, Mo.; 10 ng per 100 μl volume) then were prepared, to evaluate the binding of TGF-beta to IgG with and without salt and with and without glycerol. A control sample also was prepared, containing no TGF-beta.

Accordingly, 100 μL volumes of each of the following five samples was added to a well of the blocked ELISA plate: (1) PBS alone (no TGF-beta—negative control); (2) 0.1M Tris pH 7.4 (0 mM NaCl); (3) PBS (0.15 mM NaCl); (4) 10% glycerol in 0.1M Tris pH 7.4 (decreased hydrophobicity (0 mM NaCl)); and (5) 10% glycerol in PBS (increased hydrophobicity (0.15 mM NaCl). The samples were incubated on the plates for 18 hours at 4° C. After washing with TBST, the remaining TGF-beta (bound to IgG) was assayed using eBioscience Human/Mouse TGF-1 ELISA Ready-Set-Go! Kit (EBioscience). Resulting net absorbance units are listed in Table 3, below.

TABLE 3

Binding of TGF-beta to total IgG under varying conditions

| Sample | Binding condition | Net Absorbance (450) |
|---|---|---|
| 1 | Negative control (no TGF-beta added - PBS alone): | 0 |
| 2 | TGF-beta/Tris: | 1.02 |
| 3 | TGF-beta/PBS | 0.18 |
| 4 | TGF-beta/Tris/Glycerol | 0.70 |
| 5 | TGF-beta/PBS/Glycerol | 0 |

The results, shown in Table 3, revealed that binding of TGF-beta to IgG was improved in a low-salt environment (Tris, 0 M NaCl) compared to a polarizing environment (PBS, 0.15 mM NaCl). The presence of glycerol decreased binding in both environments.

Following the study described above, additional optimization studies were carried out to evaluate binding of TGF-beta to soluble IgG at different salt concentrations, pHs, and temperatures. For these studies, TGF-beta (Peprotech, Rocky Hill, N.J.) was diluted to 20 µg/mL in PBS and total mouse IgG (Sigma-Aldrich) was diluted to 1 mg/mL in PBS. The diluted TGF-beta and IgG were combined, and incubated for five minutes, with the following buffer and temperature conditions (Table 4) for samples 1-4:

TABLE 4

Combining TGF-beta and IgG

| | Sample 1 (TGF-β only control) | Sample 2 | Sample 3 | Sample 4 |
|---|---|---|---|---|
| TGF-beta | 20 ng | 20 ng | 20 ng | 20 ng |
| IgG | 0 (1 µL PBS) | 1 µg | 1 µg | 1 µg |
| Equal volume (2 µL) buffer | PBS | PBS | PBS | 0.5 × PBS (0.075 mM NaCl) w/ NaOH to pH11 |
| Incubation at temperature | RT | RT | 42° C. | RT |

*** RT = room temperature (approximately 25° C.)

After incubation for five minutes, a 2× volume (4 µL) of 1 M Tris, pH 8 was added to each sample in Table 4. Each sample then was added to a Sepharose G-50 spin column that had been equilibrated with 1% BSA in PBS (to prevent non-specific binding). Bound material was eluted from the column and the presence of TGF-beta in the eluates evaluated by ELISA. For the ELISA, the eluates were bound to a 96 well plate in $NaCO_3$, pH 9.6, for 2 hours at 37° C. Following washes with TBST, the plates were blocked as described above. An anti-TGF-beta antibody then was added, followed by washing with TBST and developing using the eBioscience kit referenced above. Table 5, below, sets forth the resulting net absorbance units.

TABLE 5

Net absorbance values
(TGF-beta ELISA from binding study of Table 4)

| Sample | Binding condition | Net Absorbance (450) |
|---|---|---|
| 1 | TGF-beta only control, RT | 0 |
| 2 | PBS, RT | 0.1926 |
| 3 | PBS 42° C. | 0.1166 |
| 4 | 0.5× PBS pH 11, RT | 0.5585 |

B. Production of AcTigg and InTigg

Based on the optimization studies in Example 1A, mouse AcTIGG and InTIGG were produced. Transforming growth factor-beta 1 was purchased from Peprotech (Rock Hill, N.J.) as a lyophilized solid. Mouse IgG1 (for mouse AcTigg) and Mouse IgG2a (for mouse I-TIGG) were purchased as 1 mg/ml solutions in PBS from eBioscience (San Diego, Calif.). Just before use, TGF-beta was resuspended in 4 mM HCl to a final concentration of 50 µg/ml. For production of AcTIGG and InTIGG, the TGF-beta solution was then added to the IgG1 and IgG2a solutions, respectively, at a molar ratio of 1:10 TGF-beta to IgG, at room temperature. After 5 minutes, the solution was diluted to a final concentration of 500 ng/ml TGF-beta in PBS and the pH adjusted to 7.4. The solution was incubated at 4° C. for 18 hrs.

For analysis of AcTIGG and InTIGG, TGF-beta-bound mIgG1 and mIgG2a, respectively, from above were run over a Sephadex G-50 column (⅙₀th column volume), by gravity flow, that had been equilibrated in PBS/1% BSA. Fractions were analyzed by ELISA, as described in Example 1A above, to assess the presence of TGF-beta.

The results revealed that approximately 40-50% of TGF-beta eluted as a broad peak just after the void volume, representing the IgG-bound TGF-beta fraction. The remaining TGF-beta eluted in a broad peak just before the total column volume, representing unbound TGF-beta.

Example 2

Production of Human AcTIGG and Human InTIGG

In one example, human InTIGG is produced as follows: Total human gamma globulin (available commercially as human "IVIG") is resuspended to a final concentration of 10 mg/ml, for example, in PBS or water. Transforming growth factor-beta is resuspended in 4 mM hydrochloric acid to a final concentration of 100 ng/ml. The TGF-beta solution is added to the IVIG solution at a molar concentration of at least 10:1 IgG to TGF-beta and mixed. To this mixture, an equal volume of PBS (titrated to pH 11 with sodium hydroxide) is added, mixed, and incubated at room temperature for 5 minutes. This solution is then adjusted to pH 7.4 and purified by chromatography.

In one example, human AcTIGG is produced as follows: Human IgG4 is resuspended to a final concentration of 10 mg/ml, for example, in PBS or water. Transforming growth factor-beta is resuspended in 4 mM hydrochloric acid to a final concentration of 100 ng/ml. The TGF-beta solution is added to the IgG4 solution at a molar concentration of at least 10:1 IgG to TGF-beta and mixed. To this mixture, an equal volume of PBS (titrated to pH 11 with sodium hydroxide) is added, mixed, and incubated at room temperature for 5 minutes. This solution is then adjusted to pH 7.4 and purified by chromatography.

Example 3

Purification of AcTigg and InTigg

For purification of the mouse AcTigg produced in example, 1B, one third volume of 32% PEG (MW 8000) in water or PBS was added to the neutralized TIGG reaction mixture (following adjustment to pH 7.4 in Example 1B), giving a final concentration of 8% PEG. The mixture was incubated for 1 hour at 4° C., centrifuged at 12 kg for 30 minutes, and the supernatant discarded. The pellet was washed with cold (4° C.) 8% PEG, centrifuged an additional 10 minutes at the same speed, and the pellet retained.

In other another example, TIGG (e.g., human or mouse TIGG as produced in Examples 1 and 2) is purified by column purification, as follows. The TIGG (AcTigg or InTigg (1 ml, less than 15 mg/ml)) is added to a Superdex 200 HR 10/30 (Vt: 24 ml), 1.0 ml/min (76 cm/h) equilibrated with 0.05 M sodium phosphate, 0.15 M NaCl, pH 7.0. Absorbance is monitored at 280 nm and fractions assayed for TGF-beta by Elisa. The first peak after the void volume is collected and retained.

Example 4

Assessing the Purity and Integrity of TIGG

An apoptosis assay, using mink lung epithelial cells (ATCC® Number CCL-64), was performed to assess the purity and integrity of the mouse AcTigg, produced in Example 1B and purified by PEG-precipitation in Example 3. For this assay, CCL-64 cells, grown in minimal essential media supplemented with 5% fetal bovine serum were aliquoted into 96-well tissue culture wells at about $1 \times 10^4$ cells per well and allowed to acclimate at 37° C., 5% CO2] overnight.

Before incubation with these cells, the PEG-precipitated AcTigg of Example 3, above was resuspended in PBS and divided into two aliquots. One aliquot ("Intact") was analyzed as is; the other aliquot ("Treated") was first incubated with acid to dissociate the Tigg into free TGF-beta and immunoglobulin by adding 1N HCl (1:25 final volume) and incubating at room temperature, 30 minutes, followed by neutralization with 1N NaOH.

The Intact and Treated samples then were analyzed by incubation with the cells in the same procedure as follows. Samples were added to CCL-64 cells at various concentrations in triplicate and incubated for 24 hours in a humidified 5% CO2 incubator at 37° C. Cells in "Control" wells were incubated under the same conditions with PBS alone. The In Vitro Toxicology Assay Kit, XTT based (Sigma Aldrich, St. Louis, Mo.), was utilized to monitor cell viability according to the manufacturer's instructions. Briefly, the XTT stock solution was reconstituted and added to each well at an amount equal to 20% of the culture medium volume. The cultures were incubated at 37° C. for an additional 4 hours with occasional gentle mixing. Absorbance was measured at 450 nm, with 690 nm as background absorbance.

The results are presented in Table 6, below. The table lists cell viability ($OD_{450}$ relative to $OD_{450}$ in Control wells (cells incubated with PBS alone)) vs. AcTigg concentration (pg/ml) for each sample. The results show higher viability of cells incubated with Intact samples, compared to "Treated" wells, indicating that the PEG-precipitated AcTigg prepared in Example 3 was relatively devoid of free TGF-beta, contained intact AcTigg complex (which did not binding the TGF-beta receptors on the cells), and was dissociated into free TGF-beta and immunoglobulin upon treatment with acid (Treated samples); these data confirm the purity and integrity of the AcTigg preparation.

TABLE 6

Intact and Acid-Dissociated (Treated) AcTigg Treatment of Mink Lung Epithelial Cells, Monitored for Cell Viability

| AcTigg Concentration (pg/mL) | Cell Viability ($OD_{450}$/Control $OD_{450}$) | |
|---|---|---|
| | Intact AcTigg | Dissociated (Treated) AcTigg |
| 0 | 1 | 1 |
| 0.25 | 0.965 | 0.621 |
| 2.5 | 0.924 | 0.645 |
| 25 | 0.897 | 0.651 |
| 250 | 0.817 | 0.651 |
| 2500 | 0.678 | 0.616 |

Example 5

Assessing the Effect of AcTigg and InTigg in Mouse Macrophages in Cell Culture

In order to assess the effect of AcTIGG and InTIGG on macrophages in cell culture, peritoneal cells are obtained by peritoneal lavage of untreated mice. The macrophages are enriched using MS columns on MiniMACS Separator (Miltenyi Biotec) by depletion with anti-CD19 and anti-CD5 microbeads (Miltenyi Biotec) per the manufacturer's instructions. The resulting cell populations are >95% CD5−, CD19−, and CD11b+. The cells are resuspended in RPMI 1640 with 5% FBS, dispensed to standard 24- or 48-well cell culture plates with the AcTigg, InTigg, or PBS control for 24 hours, followed by activation by 24 h culture with 0.1 mg/ml LPS (*Escherichia coli* 011B, Sigma-Aldrich, St. Louis, Mo.).

After 24 h of treatment with LPS, the cell cultures are assayed for the levels of M1 related cytokines TNF-alpha and IFN-γ, and M2 related cytokines MCP-1 and IL-10, compared to untreated, activated macrophages. Assays are performed using commercial kits from BD Pharmingen or R&D systems.

Example 6

Assessing the Effect of AcTigg and InTigg in Human Macrophages in Cell Culture

In order to assess the effect of AcTIGG and InTIGG on human macrophages in cell culture, human monocyte-derived macrophages are isolated and cultured using standard techniques ("Basic Cell Culture Protocols," Helgason, C D and Miller, C L, *Methods in Molecular Biology*, Volume 290, Humana Press, 2005).

The cells are resuspended in RPMI 1640 with 5% FBS, dispensed to standard 24- or 48-well cell culture plates with the AcTigg, InTigg, or PBS control for 24 hours, followed by activation by 24 h culture with 0.1 mg/ml LPS (*Escherichia coli* 011B).

After 24 h of treatment with LPS, the cell cultures are assayed for the levels of M1 related cytokines TNF-alpha and IFN-γ, and M2 related cytokines MCP-1 and IL-10, compared to untreated, activated macrophages. Assays are performed using commercial kits from BD Pharmingen or R&D systems.

Example 7

Assessing the Effect of AcTigg and InTigg in Macrophages in Mice

In order to evaluate the in vivo effects of AcTIGG and InTIGG on macrophages, two groups of C57Bl/6 mice (female, 8-10 weeks old) are injected ip 3 times per week for two weeks, with one group receiving PBS (control) injections, the other receiving test material (50 ng per injection of either AcTigg or InTigg). Two days after the last injection, peritoneal macrophages are isolated from the animals, and are purified, cultured activated, and analyzed for levels of activating and inhibitory cytokines as described in Example 3 above.

Example 8

Assessing Chemotactic Properties of InTigg and AcTigg

To evaluate chemotactic properties of the InTIGG and AcTIGG on various cell types, monocytes, lymphocytes and neutrophils are prepared by the method of Adams, et al. (Adams, D. H., et al., *J. Immunol* (1991) 147(2):609-612). Cell migration is assessed in a 48-well microchemotaxis chamber (Richards K. L., et al., *Immunol Commun* (1984) 13:49). One polyvinylpyrrolidone-free, polycarbonate membrane is used to separate the two main compartments. The pore sized to be used for neutrophil chemotaxis is 2 μM, and 8 μM is used for lymphocytes and monocytes. A known number of cells is added to the upper chambers, and varying concentrations of AcTigg, InTigg, recombinant TGF-beta, or PBS are added to the lower chambers. Chambers are incubated at 37° C. for 90 minutes. The non-migrating cells are removed from the upper surface of the membrane by careful wiping of the membrane, then the membrane is fixed in methanol and stained with Diff-Quik (Hamilton Thorne Biosciences, Beverly, Mass.). The cells migrating to the underside of the membrane are counted under a microscope and the number compared to the total number of cells added to the upper chamber. The degree of chemotaxis can be compared to recombinant TGF-beta and PBS, and its specificity demonstrated by inhibition of chemotaxis with a commercial anti-TGF-beta antibody (eBioscience, San Diego, Calif.).

Example 9

In Vivo Activity of AcTigg

Anti-Tumor Activity in Murine Syngeneic Tumor Model

This example describes a study that was carried out to demonstrate the in vivo anti-tumor effects of AcTIGG. For the tumor model, two groups of four C57Bl/6 mice were injected via tail vein with $10^5$ B 16F10 metastatic melanoma tumor cells. After three days, one group was treated with PBS and the other treated with 50 ng/animal AcTigg. The AcTIGG and PBS control were administered via intraperoteneal injection, three times per week for 2 weeks, starting 3 days after tumor injection. At day 18 after tumor injection, the mice were sacrificed, their lungs removed, and evaluated by visualization of individual dark stained regions of the lungs, which were melanoma tumor metastases. The areas of dark staining were counted visually. Table 7, below, indicates the number of tumors (number of metastases in the lung) counted in PBS treated mice vs AcTigg treated mice. The results demonstrated that treatment of the mice with AcTIGG decreased tumor burden compared to control treatment (PBS alone).

TABLE 7

Reduced tumor number (day 18 after tumor injection of tumor cells) after AcTIGG treatment in the B16 lung metastasis model

| Treatment | Number of Tumors (average; n = 4) | Standard Deviation |
|---|---|---|
| PBS | 147 | 24 |
| AcTIGG | 95 | 22 | p = 0.08

Example 10

In Vivo Activity of InTigg: Amelioration of Autoimmune Symptoms in a Murine Model of Rheumatoid Arthritis Using the Collagen-Induced Arthritis (CIA) Mouse Model This example describes a study that was carried out to demonstrate the in vivo effects of InTIGG on autoimmune disease. Collagen-induced arthritis, a well-known and widely used animal model of rheumatoid arthritis in mice and rats, was used in this study. 10 mg bovine Type II collagen (Chondrex, Inc., Redmond, Wash., Cat. 20021, lot 080099) was dissolved in 2.5 ml 0.01 M acetic acid. The collagen was placed on a stirrer at 4-8° C. to prepare a 4 mg/ml solution. For inducing arthritis, DBA/1J mice (males, Jackson Laboratories, P.O. #877440, R #2532, 5-6 weeks old) were immunized intradermally in two sites at the base of the tail with 200 μg of collagen in Complete Freund's adjuvant (CFA). CFA was prepared by grinding, with pestle and mortar, 100 mg of *Mycobacterium tuberculosis* H37Ra (BD Biosciences, San Jose, Calif.) to produce a fine powder, followed by suspension in 30 ml of incomplete Freund's adjuvant (BD Biosciences, San Jose, Calif.).

For macroscopic assessment of arthritis, the thickness of each affected hind paw was measured daily with microcalipers and the diameter can be expressed as the average for inflamed hind paws per mouse Animals were also scored for clinical signs of arthritis as follows: 0=no visible effects of arthritis; 1=edema and erythema of one digit or joint; 2=edema and erythema of two joints; 3=edema and erythema of more than two joints; 4=severe arthritis of the entire paw and digits, accompanied by ankylosis of the ankle and deformity of the limb. Each limb the mouse was graded, with a maximum score of 12 per mouse.

The ability of InTIGG to ameliorate disease was tested three days after arthritis had commenced (based on observance of paw swelling; here day 21). A group of diseased mice was randomly split into two groups of four animals each. The test group was treated with 50 ngs of InTIGG and the control group was injected identically with phosphate-buffered saline (PBS). Both InTIGG and PBS were administered interperatonially, three times per week for two weeks. Efficacy of InTIGG treatment was assessed daily from day −1 through day 4 and days 6, 7, 8, and 10, by comparing clinical scores of the InTIGG treated and control treated animal groups. The results, presented in Table 8, below, demonstrated that treatment with InTIGG reduced articular swelling compared to control (PBS) treatment alone.

TABLE 8

Reduced articular swelling after InTIGG-treatment in the Collagen Induced Arthritis model (n = 4)

| | Average Clinical Score (n = 4) | | | | | | | | | | | | |
|---|---|---|---|---|---|---|---|---|---|---|---|---|---|
| | Day Number | | | | | | | | | | | | |
| Treatment | −1 | 0 | 1 | 2 | 3 | 4 | 5 | 6 | 7 | 8 | 9 | 10 | 11 |
| PBS | 0.5 | 2.5 | 3.3 | 5 | 5.5 | 5.8 | N/D | 8.5 | 8.3 | 8.5 | N/D | 8.5 | N/D |
| InTIGG | 0 | 2.5 | 3.5 | 3.75 | N/D | 5 | N/D | N/D | 6 | N/D | 6.25 | N/D | 5.5 |

* N/D = not done (scores were not taken on this day for this group)

Example 11

In vivo Activity Test of InTigg

Amelioration of Autoimmune Symptoms in a Murine Model of Rheumatoid Arthritis Using the Streptococcal Cell Wall Arthritis (SCW) Mouse Model

*Streptococcus pyogenes* T12 organisms are cultured in Todd-Hewitt broth for 24 hours and harvested. Cells are disrupted with glass beads and sonicated. The material is treated with degrading enzymes and further isolated by differential ultracentrifugation as described (Williams, R. O., *Methods Mol Med* (2004), 98:207-216). The resulting 10,000 g supernatant is used. Streptococcal cell wall arthritis is induced by a single i.a. injection of 6 µl containing 25 µg (rhamnose content) in saline into the right knee joint of C57BL/6 female mice. Assessment of the degree of arthritis in the injected knee joint is identical to that described in Example 12.

The ability of InTIGG to ameliorate disease is tested in either early arthritis (2 weeks after disease onset) or late arthritis (6-8 weeks after disease onset). A group of diseased mice is randomly split into two groups, the test group is treated with one or more injections of InTIGG subcutaneously or interperatonially, whereas the control group is injected identically with phosphate-buffered saline. Both macroscopic and histologic assessment of disease are done blinded. Efficacy of InTIGG treatment is determined by its ability to reduce disease scores versus the PBS treated group.

Example 12

In Vivo Activity Test of InTigg

Amelioration of Autoimmune Symptoms in a Murine Model of Multiple Sclerosis Using the Experimental Autoimmune Encephalomyelitis (EAE) Mouse Model Ten to twelve week old NOD mice (Jackson Laboratory, Bar Harbor, Me.) are injected by subcutaneous immunization into the flanks with 200 µl of an emulsion containing 150 µg of MOG peptide 35-55 (MEVGWYRSPFSRVVHLYRNGK (SEQ ID NO:11)) and 400 µg *Mycobacterium tuberculosis* extract H37 Ra (Difco, Detroit, Mich.) in incomplete Freund's adjuvant. The first signs of disease should appear at days 11-12, peaking at days 16-18. After partial recovery from this initial acute attack, there should be a progressive worsening relapse without full remission. Clinical signs of EAE are assessed according to the following scores: 0=no signs of disease, 1=loss of tone in the tail, 2=hind limb paresis, 3=hind limb paralysis, 4=tetraplegia, 5=moribund.

The ability of InTIGG to ameliorate EAE is tested after initial signs of the disease appear. A group of diseased mice is randomly split into two groups, the test group is treated with one or more injections of InTIGG subcutaneously or interperatonially, whereas the control group is injected identically with phosphate-buffered saline. Clinical signs of EAE are assessed according to the following scores: 0=no signs of disease, 1=loss of tone in the tail, 2=hind limb paresis, 3=hind limb paralysis, 4=tetraplegia, 5=moribund. Animals are assessed in a blinded fashion, and the efficacy of InTIGG is determined in its ability to reduce the disease scores of treated animals versus the controls.

Example 13

In Vivo Activity Test of InTigg: Amelioration of Autoimmune Symptoms in a Murine Model of Colitis/Crohn's Disease Using the Dextran Sodium Sulfate Mouse Model Colitis is induced in eight week old female Swiss-Webster mice (Charles River Laboratories, Inc., Wilmington, Mass.) by feeding 4% dextran sodium sulfate (30-40 kDa, ICN Biochemicals, Costa Mesa, Calif.) ad libitum for 7 days. On day 8, animals are returned to drinking plain water and therapy is initiated.

A group of diseased mice is randomly split into two groups, the test group is treated with one or more injections of InTIGG subcutaneously or interperatonially, whereas the control group is injected identically with phosphate-buffered saline. Parameters recorded in the experiments are bodyweight, stool consistency and occurrence of occult or gross rectal blood, as described (Cooper H. S., et al., *Lab Invest* (1993), 69(2):238-249).

The ability of InTIGG to ameliorate colitis is tested during the course of the testing period. Animals are assessed in a blinded fashion, and the efficacy of InTIGG is determined in its ability to lessen the disease scores of treated animals versus the controls.

Example 14

In Vivo Activity Test of InTigg: Amelioration of Autoimmune Symptoms in a Murine Model of Type-1 Diabetes Mellitus Using the NOD Mouse The non-obese diabetic (NOD) mouse model shows striking similarities to human type-1 diabetes. NOD mice develop diabetes starting around 30 weeks of age in 80% of females and 20% of males; however, cyclophosphamide accelerates its onset. For example, cyclophosphamide has been shown to produce diabetes synchronously in 40-60% of male NOD mice after a single dose (Harada et al., *Diabetologia* (1984) 27:604-606).

Cyclophosphamide is administered twice, 14 days apart, at a dose of 200 mg/kg in PBS to 8-10 week old female NOD mice (Taconic Farms, Germantown, Md.). Diabetes is diagnosed by regular urinary glucose analysis and confirmed by blood glucose determination. Mice are considered diabetic when sequential blood glucose measurements are shown to be above or equal to 16.7 mmol/L (300 mg/dl), as determined by Accu-ChekIII glucometer, or any other commercially available glucose monitoring device. Disease progression and severity can also be monitored by the degree of insulinitis after necropsy. The pancreas is excised immediately after animal sacrifice and fixed in 10% buffered formalin, and hematoxylin- and eosin-stained histologic slides prepared. Insulinitis is graded as follows: grade 0=normal islet totally free of any periilet mononuclear cells, grade 1=focal periislet lyphocytic infiltration <25% of islet circumference, grade 2=periislet lymphocytic infiltration >25% of islet circumference, grade 3=mild insulitis, with intraislet infiltration with good retention of islet cell morphology, and grade 4=severe insulitis with significant destruction of beta-islet cells.

The ability of InTIGG to ameliorate diabetes is tested after the onset of diabetes. A group of diseased mice is randomly split into two groups, the test group is treated with one or more injections of InTIGG subcutaneously or interperatonially, whereas the control group is injected identically with phosphate-buffered saline. Animals are assessed by blood glucose measurement, and the efficacy of InTIGG is determined in its ability to lessen the concentration of blood glucose of treated animals versus the controls. InTIGG may also be tested as to its ability to lessen insulinitis.

LISTING OF SEQUENCES

SEQ ID NO: 1
(coding sequence of human TGF-beta1)
gccctggacaccaactattgcttcagctccacggagaagaactgctgcgt
gcggcagctgtacattgacttccgcaaggacctcggctggaagtggatcc
acgagcccaagggctaccatgccaacttctgcctcggccctgccctac
atttggagcctggacacgcagtacagcaaggtcctggccctgtacaacca
gcataacccgggcgcctcggcggcgccgtgctgcgtgccgcaggcgctgg
agccgctgccatcgtgtactacgtgggccgcaagcccaaggtggagcag
ctgtccaacatgatcgtgcgctcctgcaagtgcagctga SEQ ID NO: 2
(coding sequence of Fc region of human IgG1)
gcaagcttca agggcccatc ggtcttcccc ctggcaccct
cctccaagag cacctctggg ggcacagcgg ccctgggctg
cctggtcaag gactacttcc ccgaaccggt gacggtgtcg
tggaactcag gcgccctgac cagcggcgtg cacaccttcc
cggctgtcct acagtcctca ggactctact ccctcagcag
cgtggtgacc gtgccctcca gcagcttggg cacccagacc
tacatctgca acgtgaatca caagcccagc aacaccaagg
tggacaagaa agttgagccc aaatcttgtg acaaaactca
cacatgccca ccgtgcccag cacctgaact cctggggggga
ccgtcagtct tcctcttccc cccaaaaccc aaggacaccc
tcatgatctc ccggacccct gaggtcacat gcgtggtggt
ggacgtgagc cacgaagacc ctgaggtcaa gttcaactgg
tacgtggacg gcgtggaggt gcataatgcc aagacaaagc
cgcgggagga gcagtacaac agcacgtacc gtgtggtcag
cgtcctcacc gtcctgcacc aggactggct gaatggcaag
gagtacaagt gcaaggtctc caacaaagcc ctcccagccc
ccatcgagaa aaccatctcc aaagccaaag ggcagccccg
agaaccacag gtgtacaccc tgcccccatc ccgggatgag
ctgaccaaga accaggtcag cctgacctgc ctggtcaaag
gcttctatcc cagcgacatc gccgtggagt gggagagcaa
tgggcagccg gagaacaact acaagaccac gcctcccgtg
ctggactccg acggctcctt cttcctctac agcaagctca
ccgtggacaa gagcaggtgg cagcagggga acgtcttctc
atgctccgtg atgcatgagg ctctgcacaa ccactacacg
cagaagagcc tctccctgtc tccgggtaaa SEQ ID NO: 3
(coding region of Fc region of human IgG2)
gcaagcttca agggcccatc ggtcttcccc ctggcgccct
gctccaggag cacctccgag agcacagcgg ccctgggctg
cctggtcaag gactacttcc ccgaaccggt gacggtgtcg
tggaactcag gcgctctgac cagcggcgtg cacaccttcc
cagctgtcct acagtcctca ggactctact ccctcagcag
cgtggtgacc gtgccctcca gcaacttcgg cacccagacc
tacacctgca acgtagatca caagcccagc aacaccaagg
tggacaagac agttgagcgc aaatgttgtg tcgagtgccc
accgtgccca gcaccacctg tggcaggacc gtcagtcttc
ctcttccccc caaaacccaa ggacaccctc atgatctccc
ggacccctga ggtcacgtgg gtggtggtgg acgtgagcca
cgaagacccc gaggtccagt tcaactggta cgtggacggc
gtggaggtgc ataatgccaa gacaaagcca cgggaggagc
agttcaacag cacgttctgt gtggtcagcg tcctcaccgt
tgtgcaccag gactggctga acggcaagga gtacaagtgc
aaggtctcca acaaaggcct cccagccccc atcgagaaaa
ccatctccaa aaccaaaggg cagccccgag aaccacaggt
gtacaccctg cccccatccc gggaggagat gaccaagaac
caggtcagcc tgacctgcct ggtcaaaggc ttctacccca
gcgacatcgc cgtggagtgg gagagcaatg gcagccgga
gaacaactac aagaccacac tcccatgct ggactccgac
ggctccttct tcctctacag caagctcacc gtggacaaga
gcaggtggca gcaggggaac gtcttctcat gctccgtgat
gcatgaggct ctgcacaacc actacacgca agagcctc
tccctgtctc cgggtaaa SEQ ID NO: 4
(coding region of Fc region of human IgG3)
atcacaagcc cagcaacacc aaggtggaca agagagttga
gctcaaaacc ccacttggtg acacaactca cacatgccca
ccgtgcccag cacctgaact cctgggggga ccgtcagtct
tcctcttccc cccaaaaccc aaggacaccc tcatgatctc
ccggacccct gaggtcacat gcgtggtggt ggacgtgagc
cacgaagacc ctgaggtcaa gttcaactgg tacgtggatg
gcgtggaggt gcataatgcc aagacaaagc cgcgggagga
gcagtacaac agcacgtacc gtgtggtcag cgtcctcacc
gtcctgcacc aggactggct gaatggcaag gagtacaagt
gcaaggtctc caacaaagcc ctcccagccc ccatcgagaa
aaccatctcc aaagccaaag ggcagccccg agaaccacag
gtgtacaccc tgcccccatc ccgggatgag ctgaccaaga
accaggtcag cctgacctgc ctggtcaaag gcttctatcc
cagcgacatc gccgtggagt gggagagcaa tgggcagccg
gagaacaact acaagaccac gcctcccgtg ctggactccg
acggctcctt cttcctctac agcaagctca ccgtggacaa
gagcaggtgg cagcagggga acgtcttctc atgctccgtg
atgcatgagg ctctgcacaa ccactacacg cagaagagcc
tctccctgtc tccgggtaaa tgagtgcgac ggc SEQ ID NO: 5
(coding region of Fc region of human IgG4)
gcaagcttca agggcccatc ggtcttcccc ctggtgccct
gctccaggag cacctccgag agcacagccg ccctgggctg
cctggtcaag gactacttcc ccgaaccggt gacggtgtcg
tggaactcat gcgccctgac cagcggcgtg cacaccttcc
cggctgtcct acagtcctca ggactctact ccctcagcag
cgtggtgacc gtgccctcca gcagcttggg cacgaagacc
tacacctgca acgtagatca caagcccagc aacaccaagg
tggacaagag agttgagtcc aaatatggtc ccccatgccc
atcatgccca gcacctgagt tcctgggggg accatcagtc
ttcctgttcc ccccaaaacc caaggacact ctcatgatct
cccggacccc tgaggtcacg tgcgtggtgg tggacgtgag
ccaggaagac cccgaggtcc agttcaactg gtacgtggat
ggcgtggagg tgcataatgc caagacaaag ccgcgggagg
agcagttcaa cagcacgtac cgtgtggtca gggtcctcac
cgtcctgcac caggactggc tgaacggtaa ggagtacaag
tgcaaggtct ccaacaaagg cctcccgtcc tccatcgaga
aaaccatctc caaagccaaa gggcagcccc gagagccaca
ggtgtacacc ctgcccccat cccaggagga gatgaccaag
aaccaggtca gcctgacctg cctggtcaaa ggcttctacc
ccagcgacat cgccgtggag tgggagagca atgggcagcc
ggaggacaac tacaagacca cgcctcccgt gctggactcc
gacggctcct tcttcctcta cagcaggcta accgtggaca
agagcaggtg gcaggagggg aatgtcttct catgctccgt
gatgcatgag gctctgcaca accactacac acagaagagc
ctctccctgt ctccgggtaa a SEQ ID NO: 6
(the amino acid sequence encoded
by SEQ ID NO: 1)
A L D T N Y C F S S T E K N C C V
R Q L Y I D F R K D L G W K W I H
E P K G Y H A N F C L G P C P Y I
W S L D T Q Y S K V L A L Y N Q H
N P G A S A A P C C V P Q A L E P
L P I V Y Y V G R K P K V E Q L S
N M I V R S C K C S SEQ ID NO: 7
(the amino acid sequence encoded
by SEQ ID NO: 2)
ASFKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK SEQ ID NO: 8
(the amino acid sequence encoded
by SEQ ID NO: 3)
ASFKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTWVVVDVSHEDP
EVQFNWYVDGVEVHNAKTKPREEQFNSTFCVVSVLTVVHQDWLNGKEYKC
KVSNKGLPAPIEKTISKTKGQPREPQVYTLPPSREEMTKNQVSLTCLVKG
FYPSDIAVEWESNGQPENNYKTTPPMLDSDGSFFLYSKLTVDKSRWQQGN
VFSCSVMHEALHNHYTQKSLSLSPGK SEQ ID NO: 9
(the amino acid sequence encoded
by SEQ ID NO: 4)
HKPSNTKVDKRVELKTPLGDTTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 10
(the amino acid sequence encoded
by SEQ ID NO: 5)
ASFKGPSVFPLVPCSRSTSESTAALGCLVKDYFPEPVTVSWNSCALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVRVLTVLHQDWLNGKEYK
CKVSNKGLPSSIEKTISKAKGQPREPQVYTLPPSQEEMTKNQVSLTCLVK
GFYPSDIAVEWESNGQPEDNYKTTPPVLDSDGSFFLYSRLTVDKSRWQEG
NVFSCSVMHEALHNHYTQKSLSLSPGK

The invention claimed is:

1. An isolated Transforming Growth Factor-beta-bound IgG (TIGG), comprising:
an immunoglobulin (Ig) portion and a transforming growth factor-beta portion, wherein:
the TGF-beta portion contains a TGF-beta protein comprising the amino acid sequence of a polypeptide that has (i) at least 95% sequence identity to SEQ ID NO: 6 and (ii) at least substantially the same binding affinity for a mammalian TGF-beta type II receptor as a polypeptide of SEQ ID NO: 6;
the Ig portion contains an Ig protein with an Fc region, which has at least 95% sequence identity to the sequence of amino acids set forth in SEQ ID NO: 7, SEQ ID NO: 8, SEQ ID NO: 9 or SEQ ID NO: 10 and binds to an Fc gamma receptor; and
the Ig protein and TGF-beta protein are associated via a non-covalent bond between the constant region of the Ig protein and the TGF-beta protein.

2. The TIGG of claim 1 that is an activating TIGG (Ac-TIGG), wherein the Ig portion contains a higher binding affinity for inhibitory Fc gamma receptors compared to activating Fc gamma receptors.

3. The TIGG of claim 1, wherein the Ig portion contains a human IgG4 or Fc portion thereof.

4. The TIGG of claim 1 that is an inhibitory TIGG (In-TIGG), wherein the Ig portion contains a higher binding affinity for activating Fc gamma receptors compared to inhibitory Fc gamma receptors.

5. The TIGG of claim 4, wherein the Ig portion contains any one or more of a human IgG1 or Fc portion thereof, human IgG2 or Fc portion thereof, and a human IgG3 or Fc portion thereof.

6. The TIGG of claim 1, wherein the TGF-beta protein comprises a dimer of TGF-beta protein monomers, wherein the dimer, when not associated with the TIGG, has at least substantially the same TGF-beta activity as a wild-type TGF-beta 1 dimer.

7. The TIGG of claim 6, wherein the dimer is a homodimer, wherein each monomer has at least 95% sequence identity to SEQ ID NO: 6.

8. The TIGG of claim 1, wherein the TIGG is a purified TIGG.

9. A pharmaceutical composition comprising an isolated Transforming Growth Factor-beta-bound IgG (TIGG) complex, containing an immunoglobulin (Ig) portion and a transforming growth factor-beta portion, admixed with a pharmaceutically acceptable carrier, wherein:
the TGF-beta portion contains a TGF-beta protein comprising the amino acid sequence of a polypeptide that has (i) at least 95% sequence identity to SEQ ID NO: 6 and (ii) at least substantially the same binding affinity for a mammalian TGF-beta type II receptor as a polypeptide of SEQ ID NO: 6;
the Ig portion contains an IgG protein or functional portion thereof, which binds to an Fc gamma receptor; and the Ig protein or functional portion thereof and TGF-beta protein are associated via a non-covalent bond between the constant region of the Ig protein and the TGF-beta protein.

10. The pharmaceutical composition of claim 9, wherein the IgG protein contains at least at or about 95% sequence identity to the sequence of amino acids set forth in SEQ ID NO: 7, SEQ ID NO: 8, SEQ ID NO: 9 or SEQ ID NO: 10.

11. The pharmaceutical composition of claim 9, wherein the TIGG complex comprises a plurality of TIGG complexes, wherein:
the TGF-beta portion of each of the TIGG complexes contains a TGF-beta protein having at least 95% sequence identity to SEQ ID NO: 6.

12. An isolated Transforming Growth Factor-beta-bound IgG (TIGG), comprising:
an immunoglobulin portion and a transforming growth factor-beta portion, wherein:
the TGF-beta portion contains a dimer of two TGF-beta monomers, wherein at least one of the monomers has at least 95% sequence identity to SEQ ID NO: 6 and the dimer, when not associated with the TIGG, has at least substantially the same TGF-beta activity as a wild-type TGF-beta 1 dimer;
the Ig portion contains an Ig protein with an Fc region, which has at least 95% sequence identity to the sequence of amino acids set forth in SEQ ID NO: 7, SEQ ID NO: 8, SEQ ID NO: 9 or SEQ ID NO: 10 and binds to an Fc gamma receptor; and
the Ig protein and TGF-beta protein are associated via a non-covalent bond between the constant region of the Ig protein and the TGF-beta protein.

13. The TIGG of claim 12, wherein the dimer is a homodimer, wherein each of the two monomers contains at least 95% identity to SEQ ID NO: 6.

14. The TIGG of claim 12 that is an activating TIGG (AcTIGG), wherein the Ig portion contains a higher binding affinity for inhibitory Fc gamma receptors compared to activating Fc gamma receptors.

15. The TIGG of claim 12 that is an inhibitory TIGG (InTIGG), wherein the Ig portion contains a higher binding affinity for activating Fc gamma receptors compared to inhibitory Fc gamma receptors.

16. A pharmaceutical composition comprising the isolated Transforming Growth Factor-beta-bound IgG (TIGG) of claim 12, admixed with a pharmaceutically acceptable carrier.

17. The TIGG of claim 1, wherein the TGF-beta protein comprises at least 99% identity to SEQ ID NO: 6.

18. An isolated Transforming Growth Factor-beta-bound IgG (TIGG), comprising:
an immunoglobulin portion and a transforming growth factor-beta portion, wherein:
the TGF-beta portion contains a TGF-beta protein having at least 99% sequence identity to SEQ ID NO: 6;
the Ig portion contains an Ig protein with an Fc region, which has at least 95% sequence identity to the sequence of amino acids set forth in SEQ ID NO: 7, SEQ ID NO: 8, SEQ ID NO: 9 or SEQ ID NO: 10 and binds to an Fc gamma receptor; and
the Ig protein and TGF-beta protein are associated via a non-covalent bond between the constant region of the Ig protein and the TGF-beta protein.

19. The TIGG of claim 18, wherein the TGF-beta protein comprises SEQ ID NO: 6.

20. The TIGG of claim 18, wherein the Fc region comprises at least 99% sequence identity to the sequence of amino acids set forth in SEQ ID NO: 7, SEQ ID NO: 8, SEQ ID NO: 9 or SEQ ID NO: 10.

21. The TIGG of claim 18, wherein the Fc region comprises SEQ ID NO: 7, SEQ ID NO: 8, SEQ ID NO: 9 or SEQ ID NO: 10.

22. The TIGG of claim 18, wherein the TGF-beta protein comprises SEQ ID NO: 6 and the Fc region comprises SEQ ID NO: 7, SEQ ID NO: 8, SEQ ID NO: 9 or SEQ ID NO: 10.

* * * * *